United States Patent [19]

King et al.

[11] Patent Number: 5,225,600
[45] Date of Patent: * Jul. 6, 1993

[54] AMINES CATALYSIS USING GROUP VIB METAL-CONTAINING CONDENSATION CATALYSTS

[75] Inventors: Stephen W. King, Scott Depot; Arthur R. Doumaux, Jr., Charleston; David J. Schreck, Cross Lanes, all of W. Va.

[73] Assignee: Union Carbide Chemicals & Plastics Technology Corporation, Danbury, Conn.

[*] Notice: The portion of the term of this patent subsequent to Aug. 26, 2009 has been disclaimed.

[21] Appl. No.: 934,901

[22] Filed: Aug. 26, 1992

Related U.S. Application Data

[63] Continuation of Ser. No. 742,731, Aug. 6, 1991, abandoned, which is a continuation of Ser. No. 390,708, Aug. 8, 1989, abandoned.

[51] Int. Cl.⁵ .................. C07C 209/16; C07C 209/22
[52] U.S. Cl. .................... 564/480; 544/359; 544/401; 544/402; 502/308; 502/309; 564/470; 564/479; 564/503; 564/505; 564/506; 564/507; 564/508; 564/511; 564/512
[58] Field of Search ............... 564/480, 470, 479, 503, 564/505, 506, 507, 508, 511, 512; 544/359, 401, 402; 502/308, 309

[56] References Cited

U.S. PATENT DOCUMENTS

| | | | |
|---|---|---|---|
| 1,875,746 | 9/1932 | Martin et al. | 564/480 |
| 2,073,671 | 4/1931 | Andrews | 260/127 |
| 2,389,500 | 11/1945 | Goshorn | 260/585 |
| 2,467,205 | 4/1949 | Gresham et al. | 260/268 |
| 2,529,923 | 11/1950 | Dickey et al. | 564/480 |
| 3,128,311 | 4/1964 | Shirley et al. | 564/480 |
| 4,036,881 | 7/1977 | Brennan et al. | 260/583 P |
| 4,044,053 | 8/1977 | Brennan et al. | 260/583 P |
| 4,206,150 | 6/1980 | Slaugh | 564/480 |
| 4,301,036 | 11/1981 | Childress et al. | 252/458 |
| 4,314,083 | 2/1982 | Ford et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,362,886 | 12/1982 | Ford et al. | 564/479 |
| 4,394,524 | 7/1983 | Ford et al. | 564/479 |
| 4,399,308 | 8/1983 | Ford et al. | 564/479 |
| 4,448,997 | 5/1984 | Brennan | 564/479 |
| 4,463,193 | 7/1984 | Johnson et al. | 564/479 |
| 4,503,253 | 3/1985 | Ford et al. | 564/479 |
| 4,521,600 | 6/1985 | Wells et al. | 544/352 |
| 4,524,143 | 6/1985 | Vanderpool | 502/208 |
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,552,961 | 11/1985 | Herdle | 544/402 |
| 4,555,582 | 11/1985 | Vanderpool | 564/479 |
| 4,560,798 | 12/1985 | Ford et al. | 564/503 |
| 4,578,517 | 3/1986 | Johnson et al. | 564/479 |

(List continued on next page.)

FOREIGN PATENT DOCUMENTS

| | | |
|---|---|---|
| 0312253 | 10/1988 | European Pat. Off. . |
| 0290960 | 11/1988 | European Pat. Off. . |
| 375355 | 6/1990 | European Pat. Off. . |
| 78945 | 5/1985 | Japan . |
| 236752 | 10/1986 | Japan . |
| 236753 | 10/1986 | Japan . |
| 6323744 | 1/1988 | Japan . |
| 303964 | 12/1988 | Japan . |
| 211246 | 8/1990 | Japan . |
| 2147896 | 10/1984 | United Kingdom . |
| 9003963 | 4/1990 | World Int. Prop. O. . |

Primary Examiner—Richard L. Raymond
Assistant Examiner—Scott C. Rand
Attorney, Agent, or Firm—R. M. Allen

[57] ABSTRACT

This invention relates to a process for making amines by condensing an amino compound in the presence of a Group VIB metal-containing condensation catalyst. This invention also relates to an alkyleneamines producers composition rich in triethylenetetramine (TETA), tetraethylenepentamine (TEPA) and pentaethylenehexamine (PEHA).

35 Claims, No Drawings

U.S. PATENT DOCUMENTS

| | | | |
|---|---|---|---|
| 4,578,518 | 3/1986 | Vanderpool et al. | 564/479 |
| 4,578,519 | 3/1986 | Larken et al. | 564/479 |
| 4,584,405 | 4/1986 | Vanderpool | 564/479 |
| 4,584,406 | 4/1986 | Vanderpool et al. | 564/479 |
| 4,588,842 | 5/1986 | Vanderpool | 564/479 |
| 4,605,770 | 8/1986 | Ford et al. | 564/479 |
| 4,609,761 | 9/1986 | Watts, Jr. et al. | 564/479 |
| 4,612,397 | 9/1986 | Renken | 564/479 |
| 4,617,418 | 10/1986 | Ford et al. | 564/479 |
| 4,625,030 | 11/1986 | Best | 564/480 |
| 4,647,701 | 3/1987 | Gibson | 564/480 |
| 4,683,335 | 7/1987 | Knifton et al. | 564/480 |
| 4,698,427 | 10/1987 | Vanderpool | 544/404 |
| 4,720,588 | 1/1988 | Turcotte et al. | 564/479 |
| 4,774,218 | 9/1988 | Shimasaki et al. | 502/202 |
| 4,806,517 | 2/1989 | Vanderpool et al. | 502/208 |
| 4,833,248 | 5/1989 | Shimasaki et al. | 546/184 |
| 4,841,061 | 6/1989 | Shimasaki et al. | 546/184 |
| 4,922,024 | 5/1990 | Bowman et al. | 564/480 |

AMINES CATALYSIS USING GROUP VIB METAL-CONTAINING CONDENSATION CATALYSTS

This application is a continuation of prior U.S. application Ser. No. 07/742,731 Filing Date Aug. 6, 1991, now abandoned, which is a continuation of application Ser. No. 07/390,708 Aug. 8, 1989, now abandoned.

RELATED APPLICATIONS

U.S. patent application Ser. No. 136,615, filed Dec. 22, 1987, commonly assigned.

The following are related, commonly assigned applications, filed on an even date herewith: U.S. patent application Ser. No. 390,829, U.S. patent application Ser. No. 390,709; U.S. patent application Ser. No. 390,714; U.S. patent application Ser. No. 309,828; and U.S. patent application Ser. No 390,706; all incorporated herein by reference.

BRIEF SUMMARY OF THE INVENTION

1. Technical Field

This invention relates to a process for making amines by condensing an amino compound in the presence of a Group VIB metal-containing condensation catalyst.

This invention also relates to an alkyleneamines producers composition rich in higher polyalkylene polyamines such as triethylenetetramine (TETA), tetraethylenepentamine (TEPA) and pentaethylenehexamine (PEHA).

2. Background of the Invention

There is a substantial body of literature directed to the use of various acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self-condensation of ethylenediamine (EDA) under vapor phase conditions, to initially produce ethyleneamines, but after recycle, eventually generates piperazine through multistep condensation reactions, followed by deamination, recommends "dehydration catalysts" which are thereafter characterized as "silica gel, titania gel, alumina, thoria, boron phosphate, aluminum phosphate, and the like."

U.S. Pat. No. 2,073,671 describes the condensation catalyst in the following terms:

". . . a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid, primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 describes the "catalytic deamination of alkylene polyamines" by reacting diethylenetriamine (DETA) vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

U.S. Pat. Nos. 4,540,822, 4,584,406 and 4,588,842 depict the use of Group IVB metal oxides as supports for phosphorus catalysts used to effect the condensation of amino compounds with alkanolamines.

U.S. Pat. No. 4,683,335 describes the use of tungstophosphoric acid, molybdophosphoric acid or mixtures deposited on titania as catalysts for the condensation of amines and alkanolamines to make polyalkylenepolyamines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to MEA in the feed. The only specific metal sulfates disclosed in the patents are antimony sulfate, beryllium sulfate, iron sulfate and aluminum sulfate.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed. Each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine. Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Patent Applications 0 069 322, 0 111 928 and 0 158 319; East German Patent No. 206,896; Japanese Patent Publication No. 51-141895; and French Patent No. 1,381,243. The evolution of the art to the use of the acid catalyzed condensation reaction to generate acyclic alkyleneamines, particularly acyclic polyalkylenepolyamines, as the predominant products stemmed from the initial disclosure in U.S. Pat. No. 4,036,881, though earlier patent literature fairly well characterized such an effect without labeling it so, see U.S. Pat. No. 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524 and U.S. Pat. No. 4,463,193 for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing acid catalysts for making alkyleneamines is set forth in Table 1 below.

TABLE 1

| CITATION | CATALYST TYPE | REACTANTS |
|---|---|---|
| U.S. Pat. No. 2,467,205 | Silica gel, titania gel, alumina, thoria, aluminum phosphate. Preferred catalyst is basic aluminum phosphate. | Vapor phase condensation of EDA over a fixed bed of the catalyst, multipass process shifts from polyethylenepolyamines with the first few cycles. |
| U.S. Pat. No. 4,036,881 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. Pat. No. 4,044,053 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous acids and phosphoric acids wherein said alkyl groups have from 1 to about 8 carbon atoms and said aryl groups have from 6 to about 20 carbon atoms, alkali metal monosalts of phosphoric acid and mixtures of the above. | Alkanepolyols and alkyleneamine in liquid phase reaction. |
| U.S. Pat. No. 4,314,083 | Salt of a nitrogen or sulfur containing substance or the corresponding acid. | Alkanolamine and an alkyleneamine in liquid phase reaction. |
| U.S. Pat. No. 4,316,840 | Metal nitrates and sulfates including zirconium sulfate. | Reforming linear polyamines. |
| U.S. Pat. No. 4,316,841 | Phosphate, preferably boron phosphate. | Reforming linear polyamines. |
| U.S. Pat. No. 4,324,917 | Phosphorous-containing cation exchange resin. | Alkanolamine and an alkyleneamine in liquid phase reaction. |
| U.S. Pat. No. 4,362,886 | Arsenic, antimony or bismuth containing compounds. Antimony sulfate specifically disclosed. | Alkanolamine and an alkyleneamine in liquid phase reaction. |
| U.S. Pat. No. 4,399,308 | Lewis acid halide. | Alkanolamine and an alkyleneamine in liquid phase reaction. |
| U.S. Pat. No. 4,394,524 | Phosphorus-containing substance or salt of a sulfur-containing substance, or the corresponding acid. | Ammonia, alkanolamine and an alkyleneamine in liquid phase reaction. |
| U.S. Pat. No. 4,448,997 | Reacts alumina with phosphoric acid, adds ammonium hydroxide. | EDA with MEA. |

TABLE 1-continued

| CITATION | CATALYST TYPE | REACTANTS |
|---|---|---|
| U.S. Pat. No. 4,463,193 | Group IIIB metal acid phosphate. | Ammonia, alkanolamine and an alkyleneamine. |
| U.S. Pat. No. 4,503,253 | Supported phosphoric acid. | Ammonia, alkanolamine and an alkyleneamine. |
| U.S. Pat. No. 4,521,600 | Select hydrogen phosphates and pyrophosphates. | Alkanolamine and an alkyleneamine. |
| U.S. Pat. No. 4,524,143 | Phosphorus impregnated onto zirconium silicate support. | Alkanolamine and an alkyleneamine. |
| U.S. Pat. No. 4,540,822 | Phosphorus compound deposited on a Group IVB metal oxide support. | Alkanolamine and an alkyleneamine, regenerates the catalyst with $O_2$-containing gas. |
| U.S. Pat. No. 4,547,591 | Silica-alumina alone or in combination with an acidic phosphorus cocatalyst. | An ethyleneamine and an alkanolamine; ethyleneamines; or ammonia and an alkanolamine. |
| U.S. Pat. No. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. Pat. No. 4,552,961 | Phosphorus amide compound. | Alkyleneamine and alkanolamine and/or alkylene glycol. |
| U.S. Pat. No. 4,555,582 | Phosphorus chemically bonded to a zirconium silicate support. | MEA and EDA. |
| U.S. Pat. No. 4,560,798 | Rare earth metal or strontium acid phosphate. | MEA. |
| U.S. Pat. No. 4,578,517 | Group IIIB metal acid phosphate. | Ammonia or p-/s-amine and alkanolamine. |
| U.S. Pat. No. 4,578,518 | Thermally activated, calcined, pelleted titania containing titanium triphosphate. ". . . the titania that was used was . . . anatase." (Col. 9, lines 18–19). | MEA and EDA. |
| U.S. Pat. No. 4,578,519 | Thermally activated, calcined, pelleted titania with chemically bonded phosphorus derived from polyphosphoric acid. | MEA and EDA with optional recycle of DETA. |
| U.S. Pat. No. 4,584,405 | Activated carbon, optionally treated to incorporate phosphorus. Activated carbon may be washed with strong mineral acid to remove impurities followed by water wash. Optional treatment follows. | MEA and EDA. |
| U.S. Pat. No. 4,584,406 | Pelleted Group IVB metal oxide with chemically bonded phosphorus derived from phosphoryl chloride or bromide. | MEA and EDA. |
| U.S. Pat. No. 4,588,842 | Thermally activated pelleted Group IVB metal oxide with chemically bonded phosphorus. | MEA and EDA. |
| U.S. Pat. No. 4,605,770 | Group IIA or IIIB metal acid phosphate. | Alkanolamine and an alkyleneamine "in liquid phase". |
| U.S. Pat. No. 4,609,761 | Thermally activated pelleted titania with chemically bonded phosphorus. | MEA and EDA. |
| U.S. Pat. No. 4,612,397 | Thermally activated pelleted titania with chemically bonded phosphorus. | MEA and EDA. |
| U.S. Pat. No. 4,617,418 | Acid catalysts, mentions "beryllium sulfate". | Ammonia, alkanolamine and an alkyleneamine "under vapor phase conditions". |
| Japanese Patent Application #1983-185,871, Publication #1985-78,945 | Variety of phosphorus and metal phosphates including Group IVB phosphates. | Ammonia, alkanolamine and ethyleneamine, with ammonia/alkanolamine molar ratio greater than 11. |
| U.S. Pat. No. 4,683,335 | Tungstophosphoric acid, molybdophosphoric acid or mixtures deposited on titania. Examples 2-7 characterize titania surface areas of 51, 60 and 120 $m^2/gm$. | Claims reaction of MEA and EDA, but discloses self-condensation reaction of EDA and DETA. |
| Japanese Patent Application #1985-078,391, Publication #1986-236,752 | Group IVB metal oxide with bonded phosphorus. | Ammonia and MEA. |

TABLE 1-continued

| CITATION | CATALYST TYPE | REACTANTS |
| --- | --- | --- |
| Japanese Patent Application #1985-078,392, Publication #1986-236,753 | Group IVB metal oxide with bonded phosphorus. | Ammonia and MEA. |
| U.S. Pat. No. 4,698,427 | Titania having phosphorus thermally chemically bonded to the surface thereof in the form of phosphate bonds. | Diethanolamine and/or hydroxyethyldiethylene-triamine in EDA. |
| U.S. Pat. No. 4,806,517 | Pelleted Group IVB metal oxide with phosphorus thermally chemically bonded to the surface thereof. | MEA and EDA. |

The market demand for higher polyalkylene polyamines such as TETA, TEPA and PEHA has been progressively increasing in recent years. These higher polyalkylene polyamines are desirable co-products with DETA. It would be desirable to satisfy the existing demand from a cost standpoint by modifying slightly the commercial processes directed to the manufacture of DETA from the reaction of MEA and EDA or other suitable starting raw materials such as DETA and AEEA, to the production of TETA, TEPA and PEHA as major products.

It would be desirable to have continuously produced compositions, generated by the reaction of MEA and EDA or other suitable starting raw materials such as DETA and AEEA over a fixed bed of a condensation catalyst under commercial conditions, that are rich in TETA, TEPA and PEHA, and that are not disproporationately high in PIP and other cyclics.

It would be very beneficial to have a process which increases one's ability to generate the manufacture of desirable higher polyalkylene polyamine products such as TETA, TEPA and PEHA without generating large amounts of cyclic alkylenepolyamine products. In addition, it would also be desirable to have a process with raw material flexibility which provides the potential to control congener distribution, linear to cyclic selectivity and linear to branched selectivity of the higher polyalkylene polyamines products. As used herein, congener distribution refers to polyalkylene polyamines containing the same number of nitrogen atoms but not necessarily having the same molecular weight or structure.

The above features are provided by this invention.

SUMMARY OF THE INVENTION

This invention relates in general to a process of making amines which comprises condensing an amino compound in the presence of a Group VIB metal-containing condensation catalyst. The Group VIB metal-containing condensation catalysts used herein contain sufficient residual bound hydroxyl groups or other groupings which renders catalyst formation possible by loss of water or its chemical equivalent such as ammonium hydroxide.

More particularly, this invention relates to a process of making amines by the (i) intramolecular condensation of an amino compound to an amine having a lower molecular weight or (ii) the intermolecular condensation of an amino compound with one or more of another amino compound or a compound containing an alcoholic hydroxyl group using certain Group VIB metal-containing substances as the condensation catalyst. A preferred process involves the manufacture of alkyleneamines, most desirably higher polyalkylene polyamines, by such condensation reactions utilizing one or more oxides of tungsten as the condensation catalyst.

The invention further relates to a continuously generated alkyleneamines producers composition comprising, based on 100 percent of the weight of the composition and exclusive of any water and/or ammonia present, a) greater than about 3.0 weight percent of the combination of TETA and TEPA,
b) greater than about 0.1 weight percent of TEPA,
c) greater than about 3.0 weight percent of TETA,
d) less than about 90.0 weight percent of DETA and/or EDA,
e) less than about 90.0 weight percent of MEA and/or AEEA,
f) less than about 12.5 weight percent of the combination of PIP and AEP,
g) less than about 15.0 weight percent of other polyalkylene polyamines,
h) a TETA+TAEA to PIP+AEP+PEEDA+DAEP+DPE weight ratio of greater than about 0.5,
i) a TEPA+AETAEA to PIP+AEP+PEEDA+DAEP+DPE+AEPEEDA+iAEPEEDA+AEDAEP+AEDPE+BPEA weight ratio of greater than about 0.5,
j) a TETA to TAEA weight ratio of greater than about 4.0, and
k) a TEPA to AETAEA weight ratio of greater than about 1.0.

As used herein, the term "amino compound" embraces ammonia and any compound containing nitrogen to which is bonded an active hydrogen. Also, for purposes of this invention, the term "oxide" embraces oxides, hydroxides and/or mixtures thereof.

For purposes of this invention, the chemical elements are identified in accordance with the Periodic Table of the Elements, CAS version, Handbook of Chemistry and Physics, 67th Ed., 1986-87, inside cover. Also, for purposes of this invention, Group IIIB metal oxides embraces the lanthanides and actinides.

DETAILED DESCRIPTION

The higher polyalkylene polyamines such as TETA, TEPA and PEHA are very useful commercial products for a variety of applications including fuel oil additives, corrosion inhibitors, fabric softeners, fungicides and others. As indicated above, there is lacking a commercial process for the manufacture of enhanced quantities of TETA, TEPA and PEHA especially as significant products of reaction. There is thus a need for the ability to commercially generate larger production quantities of TETA, TEPA and PEHA and that is the direction of this invention. The process of this invention provides for the reaction of MEA and DETA or other suitable starting raw materials such as EDA and AEEA to produce in a continuous manner a reaction product mixture, termed herein an "alkyleneamines producers composition", in which TETA, TEPA and PEHA are principal products of the reaction.

The process of this invention is distinctive insofar as it achieves the generation of high concentrations of TETA, TEPA and PEHA in a manner which can be suitably employed in a commercial process, particularly a continuous process, for the manufacture of alkyleneamines. In particular, the process of this invention allows the production of TETA, TEPA and PEHA in relatively high yields without generating large amounts of cyclic polyalkylene polyamine products. The process this invention provides starting raw material flexibility thereby allowing the potential to control congener distribution, linear to cyclic selectivity and linear to branched selectivity of the higher polyalkylene polyamine products.

As indicated above, this invention relates to a process of making amines which comprises condensing an amino compound in the presence of a Group VIB metal-containing condensation catalyst.

As also indicated above, this invention relates to a continuously generated alkyleneamines producers composition comprising, based on 100 percent of the weight of the composition and exclusive of any water and/or ammonia present, a) greater than about 3.0 weight percent of the combination of TETA and TEPA,
b) greater than about 0.1 weight percent of TEPA,
c) greater than about 3.0 weight percent of TETA,
d) less than about 90.0 weight percent of DETA and/or EDA,
e) less than about 90.0 weight percent of MEA and/or AEEA,
f) less than about 12.5 weight percent of the combination of PIP and AEP,
g) less than about 15.0 weight percent of other polyalkylene polyamines,
h) a TETA+TAEA to PIP+AEP+PEEDA+DAEP+DPE weight ratio of greater than about 0.5,
i) a TEPA+AETAEA to PIP+AEP+PEEDA+DAEP+DPE+AEPEEDA+iAEPEEDA+AEDAEP+AEDPE+BPEA weight ratio of greater than about 0.5,
j) a TETA to TAEA weight ratio of greater than about 4.0, and
k) a TEPA to AETAEA weight ratio of greater than about 1.0.

The alkyleneamines producers composition of this invention can be subjected to conventional separations techniques for recovering the individual components of the composition. Such techniques are well known in the art and include, for example, distillation.

This invention contemplates the catalyzed condensation by (i) intramolecular condensation of an amino compound to an amine having a lower molecular weight, and (ii) intermolecular condensation of an amino compound with one or more of another amino compound or a compound containing an alcohol hydroxyl group to an amine having a lower, same or higher molecular weight than the reactants, in the presence of a Group VIB metal-containing condensation catalyst.

While not wishing to be bound to any particular theory, it is believed that those Group VIB metal-containing substances encompassed within the scope of this invention possessing ionic character and/or ion exchange capacity exhibit desired catalytic activity and provide desired product selectivity. While the reaction mixture may initially include one or more Group VIB metal-containing substances other than Group VIB metal-containing substances possessing ionic character and/or ion exchange capacity, it is believed to be desirable that such Group VIB metal-containing substances possessing ionic character and/or ion exchange capacity be formed in situ in order to provide desired catalytic activity and product selectivity. In such instances, the catalyst preparation conditions or reaction conditions should allow for the formation of Group VIB metal-containing substances possessing ionic character and/or ion exchange capacity. Mixtures of Group VIB metal-containing substances possessing ionic character and/or ion exchange capacity with Group VIB metal-containing substances having other than ionic character and/or ion exchange capacity are believed to exhibit desired catalytic activity and provide desired product selectivity.

In accordance with this invention, Group VIB metal-containing substances can be utilized as condensation catalysts in amines processes. Suitable Group VIB metal-containing substances which are useful as condensation catalysts herein include, for example, one or more oxides of tungsten, chromium, molybdenum or mixtures thereof. A tungsten-containing substance such as one or more oxides of tungsten or tungsten metal impregnated onto a support are preferred condensation catalysts for use in this invention.

The Group VIB metal-containing condensation catalysts can be prepared by conventional methods known in the art.

The level of activity of the Group VIB metal-containing condensation catalyst of the invention is that level which of itself makes the catalyst at least as active in the condensation of amines as, for example, is phosphoric acid on an equivalent basis. Preferably, supported Group VIB metal-containing condensation catalysts should have a surface area greater than about 70 $m^2/gm$ to as high as about 260 $m^2/gm$ or greater depending upon which metal oxide described below that is employed. In the case of Group VIB metal-containing substances in association with titanium oxides, the surface area should be greater than about 140 $m^2/gm$ to as high as about 260 $m^2/gm$, more preferably, greater than about 160 $m^2/gm$ to as high as about 260 $m^2/gm$, determined according to the single point $N_2$ method. In the case of Group VIB metal-containing substances in association with zirconia oxides, the surface area should be greater than about 70 $m^2/gm$ to as high as about 150 $m^2/gm$, more preferably, greater than about 90 $m^2/gm$ to as high as about 135 $m^2/gm$, determined according to the single point $N_2$ method. It is appreciated that the metal oxides described below which can be used in association with the Group VIB metal-containing condensation catalyst and the performance moderators described below can affect the surface area of the Group VIB metal-containing condensation catalyst. While surface areas described above may be preferred, for purposes of this invention, the surface area of the Group VIB metal-containing condensation catalyst should be sufficient to contribute to product selectivity, catalytic activity and/or mechanical or dimensional strength of the catalyst.

The Group VIB metal-containing condenation catalysts useful in this invention can be associated with one or more metal oxides. Preferred metal oxides are amphoteric or slightly acidic or slightly basic. Illustrative of such metal oxides which may be utilized in association with the Group VIB metal-containing condensation catalyst include, for example, one or more of the following: Group IA metal oxides, Group IIA metal oxides, Group IIIB metal oxides (including lanthanides and actinides), Group VB metal oxides, other Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and Group IVB metal oxides or mixtures thereof. Preferred metal oxides which may be utilized in association with the Group VIB metal-containg condensation catalyst include, for example, one or more oxides of beryllium, scandium, yttrium, terbium, dysprosium, holmium, erbium, thulium, ytterbium, lutetium, titanium, zirconium, hafnium, vanadium, niobium, tantalum, tungsten, iron, cobalt, zinc, silver, aluminum, gallium, indium, silicon, germanium, tin, lead, arsenic, antimony and bismuth.

Group IVA and IVB metal oxides such as silica, titanium dioxide and zirconium dioxide are preferred for use in this invention. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, other Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum, and other Group VIB metals such as chromium, molybdenum and tungsten. The virtue of these metal oxides is that they demonstrate higher mechanical strength than the Group VIB metal-containing substance per se and can contribute to product selectivity and catalytic activity.

Illustrative of mixed metal oxides which may be used in association with the Group VIB metal-containing condensation catalyst include, for example, $TiO_2$—$SiO_2$, $TiO_2$—$Al_2O_3$O, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$V_2O_5$, $TiO_2$—$Cr_2O_3$, $TiO_2$—$ThO_2$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $ZrO_2$—$Al_2O_3$, $ZrO_2$—$SnO$, $ZrO_2$—$PbO$, $ZrO_2$—$Nb_2O_5$, $ZrO_2$—$Ta_2O_5$, $ZrO_2$—$Cr_2O_3$, $ZrO_2$—$MoO_3$, $ZrO_2$—$WO_3$, $ZrO_2$—$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Mn_2O_3$, $TiO_2$—$SiO_2$—$Co_3O_4$, $TiO_2$—$SiO_2$—$NiO$, $TiO_2$—$SiO_2$—$PbO$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_2$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxide catalysts embraced within the scope of this invention are disclosed by Tanabe et al., Bulletin of the Chemical Society of Japan, Vol. 47(5), pp. 1064–1066 (1974).

The metal oxides described herein which can be used in association with the Group VIB metal-containing condensation catalyst may contribute to product selectivity and/or catalytic activity of the reaction and/or stability of the catalyst. The catalyst structure can comprise from about 0 to about 90 percent or greater by weight of the metal oxide, preferably from about 0 to about 75 percent by weight of the metal oxide, and more preferably from about 0 to about 50 percent by weight of the metal oxide, the remainder being the weight of the Group VIB metal-containing condensation catalyst. For mixed metal oxides containing titania, higher concentrations of titania can provide very desirable product selectivities including acyclic to cyclic selectivities and linear to branched selectivities of higher polyalkylene polyamine products. As discussed hereinafter, the Group VIB metal-containing condensation catalyst of this invention may also contain support(s), binding agent(s) or other additives to stabilize or otherwise help in the manufacture of the catalyst.

Though the Group VIB metal-containing condensation catalyst of the invention provides sufficient activity to effect the condensation reaction, certain combinations of reactants and/or product formation may be benefited by treating the catalyst with a catalyst moderator, hereinafter termed "performance moderator." Catalyst moderators are widely used to control the performance of catalysts in areas of selectivity to certain products and the repression of a catalyst's proclivity to generate a broad range of reaction products. A range of suitable materials may impact the Group VIB metal-containing condensation catalysts of this invention in the variety of reaction products. The performance moderator may be any material which impacts the Group VIB metal-containing condensation catalyst's selection of reaction products or which changes the proportion of any one or more of the reaction products which the Group VIB metal-containing condensation catalyst generates at comparable processing conditions. In addition to contributing to product selectivity, the performance moderator may be any material which contributes to catalytic activity and/or catalyst stability (mechanical or dimensional strength).

An illustrative performance moderator is a mineral acid or a compound derived from a mineral acid. Suitable for use as performance moderators are one or more phosphoric acid or a salt of phosphoric acid, hydrogen fluoride, hydrofluoric acid or a fluoride salt, sulfuric acid or a salt of sulfuric acid, and the like. The moderator may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate, sodium phosphate and the like. Other illustrative performance moderators include the metal oxides described above which can be used in association with the Group VIB metal-containing condensation catalyst and also metallic phosphates and polyphosphates which may or may not have a cyclic structure and which may or may not have a condensed structure.

The metallic phosphates and polyphosphates are preferred performance moderators for use in this invention. The metallic phosphate and polyphosphate performance moderators may or may not have a cyclic structure and may or may not have a condensed structure. Suitable metallic phosphates having a cyclic structure or an acyclic structure are disclosed in U.S. patent application Ser. No. 390,706, filed on an even date herewith and incorporated herein by reference. Suitable metallic polyphosphates having a condensed structure are disclosed in U.S. patent application Ser. No. 390,709, filed on an even date herewith and incorporated herein by reference.

Suitable metallic phosphate and polyphosphate performance moderators can include, for example, metallic orthophosphates ($PO_4^{-3}$), metallic pyrophosphates ($P_2O_7^{-4}$), metallic polyphosphates (including tripolyphosphates ($P_3O_{10}^{-5}$), tetrapolyphosphates ($P_4O_{13}^{-6}$), pentapolyphosphates ($P_5O_{16}^{-7}$) and higher polyphosphates), metallic metaphosphates (including trimetaphosphates ($P_3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido- and imidophosphates of the above may also be used as performance moderators in accordance with this invention. Suitable metals which can be incorporated into the metallic phosphate and polyphosphate performance moderators include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals and mixtures thereof.

Illustrative of metallic orthophosphate performance moderators which may be utilized in this invention include, for example, $NaH_2PO_4$, $KH_2PO_4$, $RbH_2PO_4$, $LiH_2PO_4$, $MgHPO_4$, $CaHPO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, $Ca(H_2PO_4)_2$, $La(H_2PO_4)_3$ and the like. Illustrative of metallic pyrophosphate performance moderators which may be utilized in this invention include, for example, $Na_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $NrP_2O_7$, $Na_6Fe_2(P_2O_7)_3$, $Na_8Fe_4(P_2O_7)_5$, $Na_6Cu(P_2O_7)_2$, $Na_{32}Cu_{14}(P_2O_7)_{15}$, $Na_4Cu_{18}(P_2O_7)_5$, $Na_2(NH_4)_2P_2O_7$, $Ca(NH_4)_2P_2O_7$, $MgH_2P_2O_7$, $Mg(NH_4)_2P_2O_7$ and the like. Illustrative of metallic polyphosphate performance moderators which may be utilized in this invention include, for example, $NaSr_2P_3O_{10}$, $NaCa_2P_3O_{10}$, $NaNi_2P_3O_{10}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_2P_3O_{10}$, $NaMgH_2P_3O_{10}$ and the like. Illustrative of metallic metaphosphate performance moderators which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Ni(P_3O_9)_2$, $Na_4Co(P_3O_9)_2$, $Na_4Cd(P_3O_9)_2$ and the like. Illustrative of metallic ultraphosphate performance moderators which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. The preferred metallic phosphate and polyphosphate performance moderators for use in this invention include Group IA metal metaphosphates, Group IA metal dihydrogen orthophosphates and Group IA metal dihydrogen pyrophosphates, more preferably, $Na_3P_3O_9$, $NaH_2PO_4$ and $Na_2H_2P_2O_7$. Other suitable metallic phosphate and polyphosphate performance moderators which are embraced within the scope of this invention are disclosed by Van Wazer, J. R., Phosphorus and Its Compounds, Vol. 1, Interscience Publishers, Inc., New York (1958).

The metal oxides described hereinabove which can be used in association with the Group VIB metal-containiing condensation catalyst can also be used as performance moderators in accordance with this invention. The metal oxides can contribute to product selectivity, catalytic activity and/or catalyst stability (mechanical strength).

A variety of conventional phosphorus-containing substances may be suitable for use as performance moderators in this invention. The conventional substances should be capable of functioning as a performance moderator. Illustrative of conventional phosphorus-containing substances may include, for example, those disclosed in U.S. Pat. No. 4,036,881, U.S. Pat. No. 4,806,517, U.S. Pat. No. 4,617,418, U.S. Pat. No. 4,720,588, U.S. Pat. No. 4,394,524, U.S. Pat. No. 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253, U.S. Pat. No. 4,560,798 and U.S. Pat. No. 4,578,517.

Suitable conventional phosphorus-containing substances which may be employed as performance moderators in this invention include acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

The amount of the performance moderator of the mineral acid type used with the Group VIB metal-containing condensation catalyst of the invention is not narrowly critical. Generally, the amount does not exceed 25 weight percent of the weight of the catalyst. As a rule, it is desirable to use at least 0.01 weight percent of the weight of the catalyst. Preferably, the amount of performance moderator, when used, will range from about 0.2 to about 10 weight percent of the weight of the catalyst. Most preferably, the amount of performance moderator, when used, will range from about 0.5 to about 5 weight percent of the weight of the catalyst.

The amount of performance moderator other than the mineral acid type used with the Group VIB metal-containing condensation catalyst is not narrowly critical. Generally, the amount does not exceed 90 weight percent of the weight of the catalyst. The amount of performance moderator can range from about 0 to about 90 or greater weight percent of the weight of the catalyst, preferably from about 0 to about 75 weight percent of the weight of the catalyst, and more preferably from about 0 to about 50 weight percent of the weight of the catalyst. Most preferably, the amount of performance moderator, when used, will range from about 0.5 to about 25 weight percent of the weight of the catalyst.

This invention also embraces the use of vicinal di(hetero)alkylene organometalates in the preparation of amines. Suitable vicinal di(hetero)-alkylene organometalates are disclosed in U.S. patent application Ser. No. 390,828, filed on an even date herewith and incorporated herein by reference.

The performance moderator can be provided to the Group VIB metal-containing condensation catalyst by conventional procedures known in the art. For example, the performance moderator can be provided to the catalyst by impregnating particles or monolithic structures comprising the Group VIB metal-containing condensation catalyst with liquid comprising the performance moderator. This is a well known procedure in the art for incorporating additives to a solid support material. The Group VIB metal-containing condensation catalyst of the invention may be utilized as solid powders or as fused, bonded or compressed solid pellets, or larger structures in association with the one or more metal oxides, or as coated, fused, bonded or compressed solid pellets, or larger structures, composited with one or more support materials, in association with one or more metal oxides. These solid structures may be treated with the performance moderator by mixing a liquid body of the performance moderator with the solid structure. For example, the Group VIB metal-containing condensation catalyst solids may be slurried in the performance moderator, drained, washed and suctioned to remove excess performance moderator, and then dried with heat to remove any volatiles accompanying the performance moderator. The drying temperature chosen will depend on the nature of the volatiles to be removed. Usually, the time/temperature for effecting drying will be below the conditions for effecting dehydration to remove bound water from the metal oxide in association with the Group VIB metal-containing condensation catalyst. Normally the drying temperature will be greater than about 120° C. and below about 600° C. depending on the thermal stability of the catalyst. The drying time will generally go down as the drying temperature rises and vice versus, and may extend from 5 seconds to about 24 hours.

Alternatively, the performance moderator can be provided to the catalyst at the time of preparing the Group VIB metal-containing condensation catalyst in association with one or more metal oxides. For example, one or more metal oxides may be condensed from their respective hydrolyzable monomers to the desired oxides to form oxide powders which can thereafter be blended and compressed with the Group VIB metal-containing substance to form pellets and larger structures of the metal oxide-containing condensation catalyst of this invention. The one or more metal oxides which can be used in association with the Group VIB metal-containing condensation catalyst in accordance with this invention can be provided from metal salts which can be heated to form the metal oxide. It is appreciated that the performance moderator can be incorporated into the molecular bonding configuration of the metal oxide-containing condensation catalyst by conventional procedures known in the art.

The Group VIB metal-containing condensation catalysts in association with one or more metal oxides prior to the optional treatment of the performance moderator may be prepared in a wide variety of ways. For example, one or more metal oxides may be provided as a partial condensate on a support, such as a silica or alpha, beta or gamma alumina, silicon carbide, and the like, and then condensed by heating to effect polymerization to the desired oxide form. The metal oxide(s) may be condensed from hydrolyzable monomers to the desired oxide, indeed, to form an oxide powder which can thereafter be compressed in the presence of a Group VIB metal-containing substance to form pellets and larger structures of the metal oxide-containing condensation catalyst of the invention. A blend of the powder and Group VIB metal-containing substance can be made into a shapeable paste which can be extruded and cut into pellets according to conventional procedures. The extrudate may thereafter be fired to cure the Group VIB metal-containing substance and fix the structure. The cut extrudate may be blended with a support material such as those characterized above, and the blend fired to fuse the metal oxide-containing catalyst to the support.

In a preferred embodiment of this invention, a high surface area silica or titania can be slurried with an aqueous solution of ammonium metatungstate, extruded, and calcined at a temperature of about 400° C.

A preferred catalyst structure comprises one or more oxides of tungsten or tungsten metal in association with a Group IVA or IVB metal oxide having a surface area of at least a 140 $m^2/gm$ which may or may not be bonded to a support material. The term "support," as used herein and in the claims, means a solid structure which does not adversely affect the catalytic properties of the catalyst and is at least as stable as the catalyst to the reaction medium. The support can function as an amine condensation catalyst independent of the Group VIB metal-containing substance, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the metal oxide(s) and Group VIB metal-containing substance. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the catalytic Group VIB metal-containing substance and/or metal oxide by virtue of a binding medium.

The support may constitute a separate phase in the process of extruding the catalytic structure. In this embodiment, the support forming material, preferably as a paste is blended with a paste of the Group VIB metal-containing substance and one or more metal oxides or a partial condensate thereof. The paste may comprise the oxide forms of the support and the Group VIB metal-containing substance, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide-containing condensation catalyst.

The use of supports for the Group VIB metal-containing condensation catalyst provides a number of significant advantages. It has been determined that some of the Group VIB metal-containing substances are not as stable in the amines reaction media when utilized over an extended period of time. When the reaction is effected as a batch reaction, this matter is not a problem. However, when the reaction is effected with the Group VIB metal-containing condensation catalyst as part of a fixed bed in a tubular reactor, the preferred procedure for carrying out the invention, it is desirable to have the catalyst be more stable. When the catalyst is combined with the support, the catalyst has greater stability for the reaction medium, and therefore, it is better able to be used in a fixed bed of a continuous reactor. The supported catalysts suffer from none of the leaching problems that the catalyst per se may have or the problems that are associated with the prior art catalysts, such as acidic phosphorus compounds on silica.

The reactants used in the condensation process of the invention may be ammonia or organic compound containing -NH- and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the process of the invention, include by way of example:

Ammonia

MEA—monoethanolamine
EDA—ethylenediamine
MeEDA—methylethylenediamine
EtEDA—ethylethylenediamine
AEEA—N-(2-aminoethyl)ethanolamine
HEP—N-(2 hydroxyethyl)piperazine
DETA—diethylenetriamine
AEP—N-(2-aminoethyl)piperazine
TAEA—trisaminoethylamine
TETA—triethylenetetramine
TEPA—tetraethylenepentamine
PEHA—pentaethylenehexamine TETA Isomers TAEA—trisaminoethylamine
TETA—triethylenetetramine
DPE—dipiperazinoethane
DAEP—diaminoethylpiperazine
PEEDA—piperazinoethylethylenediamine TEPA Isomers AETAEA—aminoethyltrisaminoethylamine
TEPA—tetraethylenepentamine
AEDPE—aminoethyldipiperazinoethane
AEPEEDA—aminoethylpiperazinoethylethylenediamine
AEPEEDA—isoaminoethylpiperazinoethylethylenediamine
AEDAEP—aminoethyldiaminoethylpiperazine
BPEA—bispiperazinoethylamine The foregoing also can represent the products of the reaction. For example, ammonia and MEA are frequently employed to produce EDA along with a variety of other amines, most of which are set forth above.

Glycol compounds can also be employed in the preparation of amines in accordance with this invention. For purposes of this invention, glycol compounds embrace diols and polyols. Illustrative of suitable qlycol compounds include alkylene glycols such as ethylene glycol, propylene glycol, 1,3-propane diol or mixtures thereof.

The process may be effected in the liquid or vapor or supercritical liquid states or mixtures thereof though the actual reaction is believed to occur on the catalyst's solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig.

The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the catalyst. The preferred process effects the reaction in a continuous manner over a fixed bed of the Group VIB metal-containing condensation catalyst in a tubular reactor. However, the reaction may be carried out by slurrying the catalyst in the reactants or in a batch mode in an autoclave. An inert such as nitrogen, methane and the like can be used in the reaction process.

The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
| --- | --- | --- |
| Ammonia | Methanol | Monomethylamine |
|  |  | Dimethylamine |
|  |  | Trimethylamine |
| Ammonia | MEA | EDA, DETA, AEEA, |
|  |  | TETA, TEPA, PIP |
| Ammonia | AEEA | DETA, PIP |
| MEA, Ammonia | EDA | EDA, AEEA, HEP, |
|  |  | DETA, AEP, TETA, |
|  |  | TEPA, PEHA, |
|  |  | TETA Isomers: |
|  |  | TAEA, TETA, DAEP, |
|  |  | PEEDA, DPE |
|  |  | TEPA, TEPA Isomers: |

| REACTANT | REACTANT | PRODUCTS |
|---|---|---|
| MEA | EDA | AETAEA, AEPEEDA, AEDAEP, AEDPE, BPEA AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| DETA | AEEA | TEPA Isomers, AEP |
| EDA | EDA | DETA, TETA AND TEPA Isomers |

The process of the invention provides the ability to generate the manufacture of desirable higher polyalkylene polyamine products such as TETA, TEPA and PEHA without generating large amounts of cyclic alkylenepolyamine products such as PIP, AEP and HEP. The alkyleneamines producers composition of this invention has a TETA+TAEA to PIP+AEP+-PEEDA+DAEP+DPE weight ratio of greater than about 0.5 and a TETA to TAEA weight ratio of greater than about 4.0. The process of this invention provides the potential to control congener distribution, linear to cyclic selectivity and linear to branched selectivity of the higher polyalkylene polyamines.

It is appreciated that the Group VIB metal-containing condensation catalysts of this invention may also be useful in the production of alkylamines, for example, an alcohol and at least one of ammonia, a primary amine, a secondary amine or a tertiary amine may be contacted in the presence of a Group VIB metal-containing condensation catalyst under conditions effective to produce alkylamines.

This invention is further illustrated by certain of the following examples:

EXAMPLES

In the examples set forth in the tables below, the catalyst of choice was placed in a tubular reactor having an outside diameter of 1 inch and an overall length of 30 inches. The catalyst portion of the reactor comprised a length of 24 inches, accommodating 150 cubic centimeters of catalyst. The reactor was made of 316 stainless steel. As used in the tables below, acyclic (N4)/cyclic (<=N4) refers to the weight ratio of TETA+TAEA to PIP+AEP+PEEDA+DAEP+DPE. The catalysts employed are identified as follows:

| Designation | Composition | Physical Properties |
|---|---|---|
| A | $TiO_2$ (anatase/$(NH_4)_6H_6W_{12}O_{40}$ (15 wt. % W). | Particle size: 1/16 inch cylindrical extrudates; $TiO_2$ surface area: 200 $m^2$/gm. |
| B | $TiO_2$ (anatase)/$SiO_2$/$(NH_4)_6H_6W_{12}O_{40}$ (15 wt. % W); $TiO_2/SiO_2$ wt. ratio = 88/12. | Particle size: 1/16 inch cylindrical extrudates; $TiO_2$—$SiO_2$ surface area: 175 $m^2$/gm. |
| C | $ZrO_2/SiO_2/(NH_4)_6H_6W_{12}O_{40}$ (15 wt. % W). | Particle size: 1/16 inch cylindrical extrudates; $ZrO_2$—$SiO_2$ surface area: 127 $m^2$/gm. |
| D | $TiO_2$ (anatase)/$SiO_2$/$(NH_4)_6H_6W_{12}O_{40}$ (7.5 wt. % W); $TiO_2/SiO_2$ wt. ratio = 88/12. | Particle size: 1/16 inch cylindrical extrudates; $TiO_2$—$SiO_2$ surface area: 175 $m^2$/gm. |
| E | $TiO_2$ (anatase)/$SiO_2$/$(NH_4)_6H_6W_{12}O_{40}$ (15 wt. % W)/ $La_2O_3$ (1 wt. % La); $TiO_2/SiO_2$ wt. ratio = 88/12. | Particle size: 1/16 inch cylindrical extrudates; $TiO_2$—$SiO_2$ surface area: 175 $m^2$/gm. |
| F | $TiO_2$ (anatase)/$SiO_2$/$(NH_4)_6H_6W_{12}O_{40}$ (7.5 wt. % W)/ $La_2O_3$ (0.5 wt. % La); $TiO_2/SiO_2$ wt. ratio = 88/12. | Particle size: 1/16 inch cylindrical extrudates; $TiO_2$—$SiO_2$ surface area: 175 $m^2$/gm. |
| G | $ZrO_2/SiO_2/(NH_4)_6H_6W_{12}O_{40}$ (15 wt. % W)/$La_2O_3$ (1.0 wt. % La). | Particle size: 1/16 inch cylindrical extrudates; $ZrO_2$—$SiO_2$ surface area: 127 $m^2$/gm. |
| H | $TiO_2$ (anatase)/$SiO_2/WO_3$ (3.0 wt. % $WO_3$). | Particle size: 1/16 inch cylindrical extrudates; Catalyst surface area: 234 $m^2$/gm. |
| I | $TiO_2$ (anatase)/$SiO_2/WO_3/$ $(NH_4)_6H_6W_{12}O_{40}$ (7.5 wt. % W) | Particle size: 1/16 inch cylindrical extrudates; $TiO_2$—$SiO_2$—$WO_3$ surface area: 234 $m^2$/gm. |
| J | $TiO_2$ (anatase)/$SiO_2/$ $SiO_2.12\ WO_3.$ $26\ H_2O$ (7.5 wt. % W). | Particle size: 1/16 inch cylindrical extrudates; $TiO_2$—$SiO_2$ surface area: 175 $m^2$/gm. |
| K | $TiO_2$ (anatase)/$SiO_2/Al_2O_3/$ $(NH_4)_6H_6W_{12}O_{40}$ (7.5 wt. % W). | Particle size: 1/16 inch cylindrical extrudates; $TiO_2$—$SiO_2$—$Al_2O_3$ surface area: 175 $m^2$/gm. |
| L | $TiO_2$(anatase)/$Al_2O_3/SiO_2/$ $(NH_4)_6H_6W_{12}O_{40}$ (7.5 wt. % W). | Particle size: 1/16 inch cylindrical extrudates; $TiO_2$—$Al_2O_3$—$SiO_2$ surface area: 175 $m^2$/gm. |
| M | $TiO_2$ (anatase)/$SiO_2/$ $(NH_4)_6H_6W_{12}O_{40}$ (7.5 wt. % W); $TiO_2/SiO_2$ wt. ratio = 70/30. | Particle size: 1/16 inch cylindrical extrudates; $TiO_2$—$SiO_2$ surface area: 195 $m^2$/gm. |
| N | $TiO_2$ (anatase). | Particle size: 1/16 inch cylindrical extrudates; Catalyst surface area: 200 $m^2$/gm. |
| O | $TiO_2$ (anatase)/$SiO_2$; $TiO_2/SiO_2$ wt. ratio = 70/30. | Particle size: 1/16 inch cylindrical extrudates; Catalyst surface area: 195 $m^2$/gm. |
| P | $TiO_2$ (anatase)/$SiO_2$; $TiO_2/SiO_2$ wt. ratio = 88/12. | Particle size: 1/16 inch cylindrical extrudates; Catalyst surface area: 175 $m^2$/gm. |
| Q | $ZrO_2/SiO_2.$ | Particle size: 1/16 inch cylindrical extrudates; Catalyst surface area: 127 $m^2$/gm. |

-continued

| Designation | Composition | Physical Properties |
|---|---|---|
| R | $\gamma$-$Al_2O_3$/$(NH_4)_6H_6W_{12}O_{40}$ (7.5 wt % W). | Particle size: 1/16 inch cylindrical extrudates; $\gamma$-$Al_2O_3$ surface area: 105 $m^2$/gm. |
| S | $TiO_2$ (anatase)/$SiO_2$/ $(NH_4)_6H_6W_{12}O_{40}$ (7.5 wt. % W); $TiO_2$/$SiO_2$ wt. ratio = 70/30. | Particle size: 1/16 inch cylindrical extrudates; $TiO_2$—$SiO_2$ surface area: 195 $m^2$/gm. |
| T | $TiO_2$ (anatase)/$SiO_2$/$WO_3$ (7 wt. % $WO_3$). | Particle size: 1/16 inch cylindrical extrudates; Catalyst surface area: 224 $m^2$/gm. |
| U | $TiO_2$ (anatase)/$SiO_2$/ $(NH_4)_6H_6W_{12}O_{40}$ (7.5 wt. % W)/ $B_2O_3$ (1.0 wt. % B). | Particle size: 1/16 inch cylindrical extrudates; $TiO_2$—$SiO_2$ surface area: 195 $m^2$/gm. |
| V | $TiO_2$ (anatase)/$SiO_2$/ $(NH_4)_6H_6W_{12}O_{40}$ (7.5 wt. % W)/ ZnO (1.0 wt. % Zn); $TiO_2$/$SiO_2$ wt. ratio = 70/30. | Particle size: 1/16 inch cylindrical extrudates; $TiO_2$—$SiO_2$ surface area: 195 $m^2$/gm. |
| W | $TiO_2$ (anatase)/$SiO_2$/ $(NH_4)_6H_6W_{12}O_{40}$ (7.5 wt. % W)/ $ThO_2$ (1.0 wt. % Th); $TiO_2$/$SiO_2$ wt. ratio = 70/30. | Particle size: 1/16 inch cylindrical extrudates; $TiO_2$—$SiO_2$ surface area: 195 $m^2$/gm. |
| X | $TiO_2$ (anatase)/$SiO_2$/ $(NH_4)_6H_6W_{12}O_{40}$ (7.5 wt. % W/ $NH_4F$—HF (1.0 wt. % F); $TiO_2$/$SiO_2$ wt. ratio = 70/30. | Particle size: 1/16 inch cylindrical extrudates; $TiO_2$—$SiO_2$ surface area: 195 $m^2$/gm. |
| Y | $TiO_2$ (anatase)/$SiO_2$/ $(NH_4)_6H_6W_{12}O_{40}$ (7.5 wt. % W)/ $CeO_2$ (1.0 wt. % Ce); $TiO_2$/$SiO_2$ wt. ratio = 70/30. | Particle size: 1/16 inch cylindrical extrudates; $TiO_2$—$SiO_2$ surface area: 195 $m^2$/gm. |
| Z | $TiO_2$ (anatase)/$WO_3$ (10 wt. % $WO_3$). | Particle size: 1/16 inch cylindrical extrudates; Catalyst surface area: 253 $m^2$/gm. |
| AA | $SiO_2$/$WO_3$ (10 wt. % $WO_3$). | Particle size: 1/16 inch cylindrical extrudates; Catalyst surface area: 144 $m^2$/gm. |
| BB | $TiO_2$ (anatase)/$SiO_2$; $TiO_2$/$SiO_2$ wt. ratio = 40/60 | Particle size: 1/16 inch cylindrical extrudates; Catalyst surface area: 201 $m^2$/gm. |

For each run the tubular reaction system was brought up to the designated conditions. The ammonia feed was established first, then the DETA-MEA feed. After a sufficient line out period, a two hour timed run was conducted, then the experiment was run overnight and sampled. The temperature was changed and the above procedure repeated.

The catalysts employed in the examples hereinafter were prepared as follows:

Catalyst A Preparation: Ammonium metatungstate (12.14 grams) was dissolved in water (60 grams) and an aliquot sufficient to wet the $TiO_2$ support (140 grams) was used. After wetting, the catalyst was calcined at a temperature of 350° C. for a period of 1 hour. The impregnation and calcination steps were repeated twice more to give the catalyst.

Catalyst B Preparation: Ammonium metatungstate (12.14 grams) was dissolved in water (48 grams) and an aliquot sufficient to wet the $TiO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst C Preparation: Ammonium metatungstate (12.14 grams) was dissolved in water (48 grams) and an aliquot sufficient to wet the $ZrO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst D Preparation: Ammonium metatungstate (6.07 grams) was dissolved in water (45 grams) and an aliquot sufficient to wet the $TiO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst E Preparation: Ammonium metatungstate (12.14 grams) and lanthanum nitrate (5.0 grams) were dissolved in water (45 grams) and an aliquot sufficient to wet the $TiO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst F Preparation: Ammonium metatungstate (6.07 grams) and lanthanum nitrate (2.5 grams) were dissolved in water (45 grams) and an aliquot sufficient to wet the $TiO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst G Preparation: Ammonium metatungstate (12.14 grams) and lanthanum nitrate (5.0 grams) were dissolved in water (45 grams) and an aliquot sufficient to wet the $ZrO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst H Preparation: Obtained from Norton Company, Akron, Ohio.

Catalyst I Preparation: Ammonium metatungstate (6.07 grams) was dissolved in water (35 grams) and an aliquot sufficient to wet the $TiO_2$/$SiO_2$/$WO_3$ support (55 grams) was used. After wetting, the catalyst was calcined at a temperature of 350° C. for a period of 1 hour. The impregnation and calcination steps were repeated twice more to give the catalyst.

Catalyst J Preparation: Silicotungstic acid (6.8 grams) was dissolved in water (40 grams) and an aliquot sufficient to wet the $TiO_2$/$SiO_2$ support (55 grams) was used. After wetting, the catalyst was calcined at a temperature of 350° C. for a period of 1 hour. The impregnation and calcination steps were repeated twice more to give the catalyst.

Catalyst K Preparation: Ammonium metatunqstate (6.07 grams) was dissolved in water (40 grams) and an aliquot sufficient to wet the $TiO_2$/$SiO_2$/$Al_2O_3$ support (55 grams) was used. After wetting, the catalyst was calcined at a temperature of 350° C. for a period of 1 hour. The impregnation and calcination steps were repeated twice more to give the catalyst.

Catalyst L Preparation: Ammonium metatungstate (6.07 grams) was dissolved in water (40 grams) and an aliquot sufficient to wet the TiO2/Al2O3/SiO2 support was used. After wetting, the catalyst was calcined at a temperature of 350° C. for a period of 1 hour. The impregnation and calcination steps were repeated twice more to give the catalyst.

Catalyst M Preparation: Ammonium metatungstate (6.07 grams) was dissolved in water (40 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst N Preparation: Obtained from LaRoche Chemical Company, Cleveland, Ohio.

Catalyst O Preparation: Obtained from Norton Company, Akron, Ohio.

Catalyst P Preparation: Obtained from Norton Company, Akron, Ohio.

Catalyst Q Preparation: Obtained from Norton Company, Akron, Ohio.

Catalyst R Preparation: Ammonium metatungstate (11.42 grams) was dissolved in water (45 grams) and an aliquot sufficient to wet the γ-Al2O3 support (52 grams) was used. After wetting, the catalyst was calcined at a temperature of 350° C. for a period of 1 hour. The impregnation and calcination steps were repeated twice more to give the catalyst.

Catalyst S Preparation: Ammonium metatungstate (6.07 grams) was dissolved in water (40 grams) and an aliquot sufficient to wet the TiO2/SiO2—support (55 grams) was used. After wetting, the catalyst was calcined at a temperature of 350° C. for a period of 1 hour. The impregnation and calcination steps were repeated twice more to give the catalyst.

Catalyst T Preparation: Obtained from Norton Company, Akron, Ohio.

Catalyst U Preparation: Ammonium metatungstate (6.07 grams) and boric acid (3.14 grams) were dissolved in water (30 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst V Preparation: Ammonium metatungstate (6.07 grams) and zinc nitrate (1.6 grams) were dissolved in water (30 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst W Preparation: Ammonium metatungstate (6.07 grams) and thorium nitrate (1.31 grams) were dissolved in water (35 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst X Preparation: Ammonium metatungstate (6.07 grams) and ammonium bifluoride (0.82 grams) were dissolved in water (35 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst Y Preparation: Ammonium metatungstate (6.07 grams) and cerium nitrate (1.71 grams) were dissolved in water (35 grams) and an aliquot sufficient to wet the TiO2/SiO2 support (55 grams) was used. After wetting, the catalyst was calcined at a temperature of 350° C. for a period of 1 hour. The impregnation and calcination steps were repeated twice more to give the catalyst.

Catalyst Z Preparation: Obtained from Norton Company, Akron, Ohio.

Catalyst AA Preparation: Obtained from Norton Company, Akron, Ohio.

Catalyst BB Preparation: Obtained from Norton Company, Akron, Ohio.

TABLE I

| Example No. | 1 | 2 | 3 | 4 | 5 | 6 | 7 | 8 | 9 | 10 | 11 |
|---|---|---|---|---|---|---|---|---|---|---|---|
| Catalyst Type | A | A | A | A | A | A | A | A | A | A | A |
| Catalyst weight, gm | 89.3 | 89.3 | 89.3 | 89.3 | 89.3 | 89.3 | 89.3 | 89.3 | 89.3 | 89.3 | 89.3 |
| Pressure, psig | 600 | 600 | 600 | 600 | 600 | 600 | 600 | 600 | 600 | 600 | 600 |
| Temperature, °C. | 270.4 | 271 | 280.8 | 260.7 | 270.6 | 260 | 280 | 251.2 | 260.9 | 246 | 256 |
| Time on organics, hrs. | 6 | 25 | 30 | 49 | 54 | 75 | 98 | 122 | 126 | 146 | 150 |
| Duration of run, hrs. | 2 | 2 | 2 | 2 | 2 | 2 | 2 | 2 | 2 | 2 | 2 |
| MEA SV, gmol/hr/kgcat | 2.58 | 3.38 | 3.44 | 3.51 | 3.60 | 3.57 | 3.24 | 3.36 | 3.38 | 3.39 | 3.40 |
| DETA/MEA mole ratio | 0.99 | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 7.581 | 5.561 | 8.937 | 2.704 | 3.955 | 2.560 | 6.744 | 1.365 | 2.123 | 1.102 | 1.555 |
| MEA | 5.649 | 4.652 | 1.477 | 12.445 | 6.771 | 14.307 | 1.922 | 20.539 | 13.637 | 23.785 | 17.583 |
| PIP | 2.611 | 2.188 | 3.634 | 1.038 | 1.673 | 1.040 | 2.760 | 0.505 | 0.844 | 0.316 | 0.605 |
| DETA | 20.830 | 22.594 | 17.418 | 33.381 | 27.328 | 37.933 | 21.040 | 44.901 | 35.026 | 47.146 | 40.284 |
| AEEA | 0.277 | 0.720 | 0.119 | 1.862 | 1.082 | 2.151 | 0.214 | 2.495 | 2.047 | 2.268 | 2.300 |
| AEP | 4.086 | 3.847 | 6.035 | 1.539 | 2.846 | 1.511 | 4.978 | 0.671 | 1.240 | 0.438 | 0.841 |
| HEP | 0.000 | 0.000 | 0.000 | 0.000 | 0.000 | 0.000 | 0.000 | 0.000 | 0.000 | 0.000 | 0.000 |
| TAEA | 0.417 | 1.005 | 0.410 | 1.722 | 1.235 | 1.843 | 0.687 | 1.801 | 1.866 | 1.600 | 1.913 |
| 1-TETA | 6.468 | 10.968 | 6.099 | 13.376 | 11.500 | 13.551 | 8.038 | 12.034 | 13.031 | 10.358 | 13.283 |
| DAEP | 0.214 | 2.647 | 3.666 | 0.817 | 1.651 | 0.668 | 3.053 | 0.199 | 0.603 | 0.134 | 0.303 |
| PEEDA | 1.910 | 2.007 | 3.593 | 0.689 | 1.305 | 0.551 | 2.822 | 0.149 | 0.453 | 0.084 | 0.234 |
| DPE | 0.511 | 0.786 | 0.396 | 0.496 | 0.519 | 0.388 | 0.407 | 0.158 | 0.444 | 0.132 | 0.278 |
| AE-TAEA | 1.200 | 2.252 | 1.072 | 2.980 | 2.621 | 3.187 | 1.564 | 2.189 | 3.092 | 1.688 | 2.780 |
| 1-TEPA | 4.021 | 8.850 | 3.847 | 8.247 | 8.806 | 7.806 | 6.952 | 4.035 | 7.515 | 3.427 | 5.980 |
| AE-DAEP | 2.544 | 2.479 | 3.363 | 0.847 | 1.622 | 0.596 | 2.586 | 0.217 | 0.561 | 0.186 | 0.310 |
| AE-PEEDA | 1.209 | 1.148 | 1.857 | 0.301 | 0.275 | 0.127 | 0.657 | 0.082 | 0.144 | 0.229 | 0.085 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.400 | 0.546 | 0.786 | 0.214 | 0.327 | 0.203 | 0.511 | 0.072 | 0.356 | 0.213 | 0.271 |
| BPEA | 0.426 | 0.441 | 0.406 | 0.579 | 0.417 | 0.504 | 0.538 | 0.049 | 0.256 | 0.087 | 0.212 |
| Others | 28.967 | 19.631 | 26.356 | 9.863 | 15.860 | 3.864 | 21.819 | 3.947 | 10.343 | 2.978 | 6.374 |
| MEA Conversion, % | 84.58 | 87.85 | 96.06 | 66.71 | 81.58 | 61.26 | 94.72 | 44.71 | 63.52 | 35.97 | 53.12 |

TABLE I-continued

| Example No. | 1 | 2 | 3 | 4 | 5 | 6 | 7 | 8 | 9 | 10 | 11 |
|---|---|---|---|---|---|---|---|---|---|---|---|
| DETA Conversion, % | 68.31 | 65.04 | 72.53 | 47.07 | 55.94 | 39.12 | 65.80 | 28.35 | 44.46 | 24.76 | 36.33 |
| Acyclic(N4), % | 72.31 | 68.75 | 45.95 | 88.28 | 78.55 | 90.54 | 58.13 | 96.46 | 90.84 | 97.14 | 94.89 |
| Acyclic(N5), % | 53.27 | 70.63 | 43.41 | 85.24 | 81.21 | 88.47 | 66.48 | 93.63 | 88.94 | 87.72 | 90.87 |
| $\Sigma(N5)/\Sigma(N4)$, weight ratio | 1.02 | 0.90 | 0.80 | 0.77 | 0.86 | 0.73 | 0.85 | 0.46 | 0.72 | 0.47 | 0.60 |
| Acyclic(N4)/cyclic ($<=$N4), weight ratio | 0.73 | 1.04 | 0.37 | 3.29 | 1.59 | 3.70 | 0.62 | 8.20 | 4.15 | 10.80 | 6.71 |

TABLE II

| Example No. | 12 | 13 | 14 | 15 | 16 | 17 | 18 | 19 |
|---|---|---|---|---|---|---|---|---|
| Catalyst Type | B | B | B | B | B | B | B | B |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 3.68 | 3.83 | 3.55 | 3.76 | 3.33 | 3.79 | 3.95 | 3.85 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.576 | 2.613 | 3.978 | 3.156 | 5.524 | 6.509 | 0.996 | 1.499 |
| MEA | 17.638 | 11.313 | 5.763 | 9.706 | 3.516 | 3.037 | 24.706 | 19.664 |
| PIP | 0.661 | 1.130 | 1.710 | 1.360 | 2.341 | 2.601 | 0.354 | 0.600 |
| DETA | 39.776 | 31.481 | 24.483 | 30.274 | 23.630 | 21.989 | 47.915 | 42.143 |
| AEEA | 2.240 | 1.704 | 1.039 | 1.469 | 0.510 | 0.312 | 1.910 | 2.051 |
| AEP | 0.977 | 1.950 | 3.062 | 2.204 | 4.152 | 4.514 | 0.487 | 0.818 |
| HEP | 0.000 | 0.000 | 0.000 | 0.000 | 0.000 | 0.000 | 0.000 | 0.000 |
| TAEA | 1.670 | 1.413 | 1.130 | 1.389 | 0.831 | 0.617 | 1.418 | 1.634 |
| 1-TETA | 13.251 | 13.353 | 12.483 | 13.317 | 11.047 | 9.109 | 9.280 | 11.618 |
| DAEP | 0.478 | 1.311 | 2.314 | 1.454 | 2.807 | 3.039 | 0.151 | 0.330 |
| PEEDA | 0.351 | 0.887 | 1.565 | 0.988 | 2.444 | 2.697 | 0.112 | 0.237 |
| DPE | 0.312 | 0.494 | 0.685 | 0.566 | 0.162 | 0.218 | 0.143 | 0.272 |
| AE-TAEA | 2.637 | 2.967 | 2.606 | 2.999 | 0.260 | 0.286 | 1.553 | 2.328 |
| 1-TEPA | 6.180 | 8.339 | 9.381 | 8.829 | 8.372 | 6.929 | 2.536 | 4.917 |
| AE-DAEP | 0.385 | 1.116 | 1.890 | 1.178 | 2.735 | 0.320 | 0.103 | 0.269 |
| AE-PEEDA | 0.094 | 0.460 | 0.627 | 0.505 | 0.663 | 0.684 | 0.051 | 0.063 |
| iAE-PEEDA | 0.000 | 0.000 | 0.000 | 0.000 | 0.000 | 0.000 | 0.000 | 0.000 |
| AE-DPE | 0.203 | 0.336 | 0.071 | 0.097 | 0.053 | 0.192 | 0.186 | 0.135 |
| BPEA | 0.099 | 0.280 | 0.687 | 0.358 | 0.583 | 0.477 | 0.063 | 0.072 |
| Others | 6.086 | 11.972 | 16.987 | 14.062 | 19.743 | 24.147 | 2.010 | 4.512 |
| MEA Conversion, % | 52.70 | 69.92 | 84.56 | 74.53 | 90.51 | 91.63 | 31.61 | 45.99 |
| DETA Conversion, % | 36.77 | 50.39 | 61.12 | 52.92 | 62.23 | 64.10 | 21.37 | 31.38 |
| Acyclic(N4), % | 92.89 | 84.57 | 74.88 | 83.01 | 68.69 | 62.02 | 96.33 | 94.03 |
| Acyclic(N5), % | 91.85 | 83.74 | 78.54 | 84.68 | 68.15 | 81.17 | 91.02 | 93.05 |
| $\Sigma(N5)/\Sigma(N4)$, weight ratio | 0.59 | 0.77 | 0.84 | 0.78 | 0.73 | 0.56 | 0.40 | 0.55 |
| Acyclic(N4)/cyclic ($<=$N4), weight ratio | 5.36 | 2.55 | 1.45 | 2.23 | 0.99 | 0.74 | 8.56 | 5.86 |

TABLE III

| Example No. | 20 | 21 | 22 | 23 | 24 | 25 | 26 | 27 |
|---|---|---|---|---|---|---|---|---|
| Catalyst Type | C | C | C | C | C | C | C | C |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 4.13 | 4.06 | 3.61 | 3.95 | 3.59 | 3.73 | 3.92 | 3.85 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.549 | 2.657 | 3.816 | 2.918 | 4.945 | 5.969 | 0.647 | 1.041 |
| MEA | 26.153 | 22.877 | 17.520 | 20.205 | 16.087 | 14.680 | 30.721 | 27.460 |
| PIP | 1.065 | 1.698 | 3.017 | 2.402 | 3.952 | 4.620 | 0.575 | 0.919 |
| DETA | 45.023 | 38.851 | 29.155 | 34.030 | 27.311 | 23.227 | 52.572 | 47.799 |
| AEEA | 1.218 | 0.982 | 0.837 | 1.081 | 0.676 | 0.509 | 1.117 | 1.247 |
| AEP | 1.053 | 1.832 | 3.443 | 2.575 | 4.691 | 5.337 | 0.059 | 0.880 |
| HEP | 0.000 | 0.000 | 0.000 | 0.000 | 0.000 | 0.000 | 0.000 | 0.000 |
| TAEA | 0.900 | 0.792 | 0.594 | 0.766 | 0.491 | 0.319 | 0.738 | 0.840 |
| 1-TETA | 5.944 | 6.306 | 6.128 | 6.849 | 5.723 | 4.369 | 4.214 | 5.237 |
| DAEP | 0.360 | 0.709 | 1.430 | 1.052 | 2.070 | 2.354 | 0.120 | 0.254 |
| PEEDA | 0.397 | 0.866 | 2.099 | 1.325 | 2.733 | 3.018 | 0.131 | 0.289 |
| DPE | 0.253 | 0.301 | 0.310 | 0.288 | 0.386 | 0.613 | 0.086 | 0.156 |
| AE-TAEA | 0.991 | 0.999 | 0.917 | 1.079 | 0.819 | 0.226 | 0.604 | 0.915 |
| 1-TEPA | 4.013 | 4.927 | 5.460 | 5.824 | 4.414 | 3.018 | 2.018 | 2.952 |

TABLE III-continued

| Example No. | 20 | 21 | 22 | 23 | 24 | 25 | 26 | 27 |
|---|---|---|---|---|---|---|---|---|
| AE-DAEP | 0.401 | 0.835 | 1.545 | 1.161 | 2.224 | 2.681 | 0.112 | 0.278 |
| AE-PEEDA | 0.400 | 0.554 | 0.512 | 0.489 | 0.511 | 0.542 | 0.121 | 0.220 |
| iAE-PEEDA | 0.000 | 0.000 | 0.000 | 0.000 | 0.000 | 0.000 | 0.000 | 0.000 |
| AE-DPE | 0.324 | 0.318 | 0.392 | 0.318 | 0.632 | 0.239 | 0.000 | 0.089 |
| BPEA | 0.176 | 0.309 | 0.369 | 0.281 | 0.202 | 0.202 | 0.054 | 0.073 |
| Others | 7.341 | 11.517 | 13.927 | 12.910 | 15.843 | 20.589 | 2.521 | 3.702 |
| MEA Conversion, % | 30.67 | 40.03 | 52.14 | 46.63 | 57.49 | 60.93 | 15.90 | 24.03 |
| DETA Conversion, % | 29.24 | 39.62 | 52.78 | 46.72 | 57.22 | 63.35 | 14.68 | 21.60 |
| Acyclic(N4), % | 87.11 | 79.08 | 63.63 | 74.06 | 54.49 | 43.92 | 93.59 | 89.67 |
| Acyclic(N5), % | 79.35 | 74.60 | 69.34 | 75.42 | 59.44 | 46.96 | 90.10 | 85.38 |
| Σ(N5)/Σ(N4), weight ratio | 0.80 | 0.88 | 0.87 | 0.89 | 0.77 | 0.64 | 0.55 | 0.66 |
| Acyclic(N4)/cyclic (<=N4), weight ratio | 2.19 | 1.31 | 0.65 | 0.99 | 0.44 | 0.29 | 5.08 | 2.43 |

TABLE IV

| Example No. | 28 | 29 | 30 | 31 | 32 | 33 | 34 | 35 | 36 | 37 |
|---|---|---|---|---|---|---|---|---|---|---|
| Catalyst Type | D | D | D | D | D | D | D | D | D | D |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.9 | 259.9 | 270 | 265 | 275 | 280.7 | 245.4 | 255.6 | 250.7 | 249.7 |
| Time on organics, hrs. | 23 | 27 | 48 | 53 | 71 | 96 | 119 | 143 | 4 | 22.5 |
| Duration of run, hrs. | 2 | 2 | 2 | 2 | 2 | 2 | 2 | 2 | 2 | 2 |
| MEA SV, gmol/hr/kgcat | 3.91 | 3.98 | 3.24 | 3.97 | 3.68 | 3.71 | 3.62 | 3.79 | 51.6 | 4.70 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| *Crude product composition, wt. %* | | | | | | | | | | |
| EDA | 0.813 | 1.260 | 2.398 | 1.598 | 2.314 | 2.549 | 0.484 | 0.749 | 1.094 | 0.827 |
| MEA | 21.532 | 15.622 | 10.867 | 13.317 | 7.792 | 5.589 | 27.925 | 23.876 | 20.059 | 23.108 |
| PIP | 0.251 | 0.421 | 0.882 | 0.590 | 0.731 | 0.778 | 0.097 | 0.183 | 0.327 | 0.225 |
| DETA | 47.006 | 39.567 | 32.817 | 35.817 | 32.340 | 29.857 | 52.926 | 48.757 | 43.271 | 47.311 |
| AEEA | 2.748 | 2.642 | 1.046 | 2.119 | 1.372 | 1.018 | 1.990 | 2.368 | 2.409 | 2.483 |
| AEP | 0.401 | 0.686 | 1.551 | 0.829 | 1.174 | 1.246 | 0.252 | 0.319 | 0.548 | 0.347 |
| HEP | 0.000 | 0.000 | 0.000 | 0.000 | 0.000 | 0.000 | 0.000 | 0.000 | 0.000 | 0.000 |
| TAEA | 1.801 | 1.987 | 1.375 | 1.958 | 2.017 | 1.874 | 1.232 | 1.615 | 1.501 | 1.592 |
| l-TETA | 12.031 | 14.750 | 10.951 | 12.866 | 14.396 | 13.387 | 6.891 | 9.157 | 11.936 | 10.715 |
| DAEP | 0.111 | 0.253 | 1.051 | 0.455 | 0.782 | 0.853 | 0.046 | 0.075 | 0.225 | 0.098 |
| PEEDA | 0.080 | 0.230 | 0.708 | 0.335 | 0.543 | -0.599 | 0.043 | 0.066 | 0.181 | 0.076 |
| DPE | 0.112 | 0.173 | 0.437 | 0.453 | 0.539 | 0.630 | 0.067 | 0.139 | 0.174 | 0.137 |
| AE-TAEA | 1.968 | 2.920 | 2.711 | 3.016 | 4.316 | 4.170 | 0.874 | 1.511 | 2.199 | 1.958 |
| l-TEPA | 4.549 | 6.175 | 7.240 | 6.904 | 8.891 | 9.110 | 1.270 | 2.338 | 4.246 | 3.296 |
| AE-DAEP | 0.057 | 0.500 | 1.079 | 0.522 | 0.775 | 0.951 | 0.060 | 0.082 | 0.326 | 0.147 |
| AE-PEEDA | 0.000 | 0.477 | 0.256 | 0.215 | 0.250 | 0.299 | 0.000 | 0.000 | 0.181 | 0.127 |
| iAE-PEEDA | 0.000 | 0.000 | 0.000 | 0.000 | 0.000 | 0.000 | 0.000 | 0.000 | 0.000 | 0.000 |
| AE-DPE | 0.058 | 0.314 | 0.301 | 0.358 | 0.368 | 0.496 | 0.053 | 0.099 | 0.286 | 0.112 |
| BPEA | 0.185 | 0.182 | 0.313 | 0.582 | 0.348 | 0.444 | 0.056 | 0.141 | 0.107 | 0.050 |
| Others | 2.088 | 7.250 | 12.439 | 11.787 | 13.042 | 15.672 | 1.167 | 1.829 | 5.810 | 3.174 |
| MEA Conversion, % | 42.08 | 58.67 | 69.47 | 64.44 | 79.13 | 84.73 | 23.07 | 33.43 | 45.87 | 37.58 |
| DETA Conversion, % | 25.04 | 37.95 | 45.35 | 43.31 | 48.67 | 51.65 | 13.57 | 19.42 | 30.78 | 24.24 |
| Acyclic(N4), % | 97.84 | 96.21 | 84.86 | 92.25 | 89.78 | 87.99 | 98.09 | 97.46 | 95.84 | 97.51 |
| Acyclic(N5), % | 95.56 | 86.04 | 83.61 | 85.52 | 88.33 | 85.83 | 92.64 | 92.25 | 87.72 | 92.30 |
| Σ(N5)/Σ(N4), weight ratio | 0.48 | 0.60 | 0.81 | 0.72 | 0.81 | 0.89 | 0.27 | 0.37 | 0.52 | 0.45 |
| Acyclic(N4)/cyclic (<=N4), weight ratio | 14.43 | 9.47 | 2.66 | 5.56 | 4.35 | 3.71 | 16.01 | 13.75 | 9.21 | 13.89 |

| Example No. | 38 | 39 | 40 | 41 | 42 | 43 | 44 | 45 | 46 | 47 |
|---|---|---|---|---|---|---|---|---|---|---|
| Catalyst Type | D | D | D | D | D | D | D | D | D | D |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 260 | 255.5 | 265.5 | 260.5 | 270.1 | 250.6 | 250 | 265.2 | 275.2 | 270.3 |
| Time on organics, hrs. | 28 | 46.5 | 52 | 71.5 | 76 | 95.5 | 118 | 145 | 148 | 170 |
| Duration of run, hrs. | 2 | 2 | 2 | 2 | 2 | 2 | 2 | 2 | 2 | 2 |
| MEA SV, gmol/hr/kgcat | 5.01 | 4.40 | 4.64 | 4.92 | 4.88 | 4.87 | 4.45 | 4.02 | 3.87 | 3.87 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| *Crude product composition, wt. %* | | | | | | | | | | |
| EDA | 1.292 | 1.045 | 1.658 | 1.287 | 1.756 | 0.653 | 0.658 | 1.445 | 2.153 | 1.729 |
| MEA | 16.448 | 21.025 | 15.267 | 18.822 | 12.662 | 24.836 | 24.781 | 17.208 | 11.166 | 13.488 |
| PIP | 0.399 | 0.287 | 0.516 | 0.337 | 0.537 | 0.161 | 0.156 | 0.414 | 0.698 | 0.492 |
| DETA | 39.380 | 43.930 | 37.874 | 42.302 | 36.372 | 48.917 | 49.188 | 40.090 | 34.966 | 37.519 |
| AEEA | 2.393 | 2.382 | 2.051 | 2.263 | 1.834 | 2.123 | 2.116 | 1.781 | 1.886 | 1.571 |
| AEP | 0.583 | 0.411 | 0.711 | 0.476 | 0.801 | 0.303 | 0.298 | 0.559 | 0.957 | 0.762 |
| HEP | 0.000 | 0.000 | 0.000 | 0.000 | 0.000 | 0.000 | 0.000 | 0.000 | 0.000 | 0.000 |
| TAEA | 1.770 | 1.662 | 1.767 | 1.798 | 1.909 | 1.483 | 1.480 | 1.667 | 1.789 | 1.659 |
| l-TETA | 13.854 | 11.854 | 12.904 | 12.705 | 13.617 | 9.174 | 9.069 | 11.193 | 12.877 | 11.276 |
| DAEP | 0.249 | 0.137 | 0.361 | 0.199 | 0.443 | 0.094 | 0.073 | 0.298 | 0.501 | 0.557 |
| PEEDA | 0.183 | 0.102 | 0.256 | 0.143 | 0.304 | 0.067 | 0.057 | 0.210 | 0.366 | 0.360 |

TABLE IV-continued

| | | | | | | | | | | |
|---|---|---|---|---|---|---|---|---|---|---|
| DPE | 0.205 | 0.156 | 0.410 | 0.181 | 0.122 | 0.066 | 0.128 | 0.100 | 0.135 | 0.412 |
| AE-TAEA | 3.040 | 2.393 | 3.401 | 2.775 | 3.772 | 1.512 | 1.451 | 2.977 | 3.693 | 3.182 |
| 1-TEPA | 5.724 | 4.313 | 6.650 | 4.894 | 6.982 | 2.416 | 2.266 | 5.519 | 7.108 | 5.762 |
| AE-DAEP | 0.392 | 0.289 | 0.446 | 0.324 | 0.477 | 0.105 | 0.070 | 0.367 | 0.112 | 0.680 |
| AE-PEEDA | 0.182 | 0.086 | 0.178 | 0.101 | 0.174 | 0.062 | 0.029 | 0.122 | 0.140 | 0.117 |
| iAE-PEEDA | 0.000 | 0.000 | 0.000 | 0.000 | 0.000 | 0.000 | 0.000 | 0.000 | 0.000 | 0.000 |
| AE-DPE | 0.279 | 0.133 | 0.078 | 0.141 | 0.077 | 0.044 | 0.046 | 0.058 | 0.278 | 0.193 |
| BPEA | 0.278 | 0.178 | 0.626 | 0.192 | 0.706 | 0.129 | 0.129 | 0.572 | 0.680 | 0.209 |
| Others | 7.869 | 5.310 | 8.286 | 5.602 | 9.166 | 2.965 | 2.416 | 7.580 | 9.685 | 10.183 |
| MEA Conversion, % | 55.95 | 43.59 | 58.83 | 49.17 | 65.41 | 32.04 | 31.64 | 52.56 | 68.72 | 62.38 |
| DETA Conversion, % | 37.48 | 30.13 | 39.45 | 32.28 | 41.11 | 20.65 | 19.56 | 34.48 | 41.95 | 37.97 |
| Acyclic(N4), % | 96.06 | 97.15 | 93.45 | 96.51 | 94.69 | 97.89 | 97.60 | 95.47 | 93.59 | 90.67 |
| Acyclic(N5), % | 88.54 | 90.71 | 88.30 | 90.98 | 88.22 | 92.00 | 93.08 | 88.34 | 89.91 | 88.16 |
| $\Sigma(N5)/\Sigma(N4)$, weight ratio | 0.60 | 0.53 | 0.72 | 0.56 | 0.74 | 0.39 | 0.36 | 0.71 | 0.76 | 0.71 |
| Acyclic(N4)/cyclic ($\leq$=N4), weight ratio | 9.63 | 12.34 | 6.50 | 10.84 | 7.02 | 15.35 | 14.76 | 8.11 | 5.51 | 5.00 |

| Example No. | 48 | 49 | 50 | 51 | 52 | 53 | 54 | 55 | 56 |
|---|---|---|---|---|---|---|---|---|---|
| Catalyst Type | D | D | D | D | D | D | D | D | D |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 280.7 | 250.7 | 265.7 | 259.9 | 270 | 250.4 | 265.5 | 250 | 250 |
| Time on organics, hrs. | 172 | 191 | 196 | 216 | 220 | 239 | 244 | 262 | 286 |
| Duration of run, hrs. | 2 | 2 | 2 | 2 | 2 | 2 | 2 | 2 | 2 |
| MEA SV, gmol/hr/kgcat | 3.95 | 4.44 | 4.42 | 4.32 | 4.52 | 4.32 | 4.59 | 4.28 | 3.96 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 2.487 | 0.562 | 1.308 | 0.998 | 1.594 | 0.620 | 1.133 | 0.494 | 0.560 |
| MEA | 8.016 | 26.365 | 19.043 | 21.551 | 14.399 | 26.157 | 17.426 | 24.474 | 23.986 |
| PIP | 0.837 | 0.141 | 0.371 | 0.259 | 0.462 | 0.139 | 0.304 | 0.127 | 0.146 |
| DETA | 31.719 | 51.019 | 41.915 | 45.886 | 37.620 | 49.403 | 39.117 | 47.899 | 48.509 |
| AEEA | 1.511 | 2.181 | 2.319 | 2.375 | 1.945 | 2.052 | 2.033 | 1.815 | 1.816 |
| AEP | 1.224 | 0.289 | 0.484 | 0.404 | 0.668 | 0.283 | 0.454 | 0.283 | 0.038 |
| HEP | 0.000 | 0.000 | 0.000 | 0.000 | 0.000 | 0.000 | 0.000 | 0.000 | 0.000 |
| TAEA | 1.853 | 1.399 | 1.786 | 1.788 | 1.875 | 1.377 | 1.723 | 1.389 | 1.454 |
| 1-TETA | 13.608 | 8.273 | 11.292 | 10.921 | 12.338 | 7.973 | 10.608 | 7.992 | 8.498 |
| DAEP | 0.762 | 0.078 | 0.234 | 0.143 | 0.335 | 0.095 | 0.209 | 0.102 | 0.104 |
| PEEDA | 0.533 | 0.051 | 0.168 | 0.103 | 0.259 | 0.072 | 0.149 | 0.071 | 0.079 |
| DPE | 0.509 | 0.144 | 0.321 | 0.215 | 0.438 | 0.171 | 0.354 | 0.160 | 0.170 |
| AE-TAEA | 4.179 | 1.285 | 2.934 | 2.270 | 3.574 | 1.424 | 2.823 | 1.514 | 1.614 |
| 1-TEPA | 8.123 | 2.016 | 4.826 | 3.679 | 6.077 | 2.067 | 4.493 | 2.110 | 2.426 |
| AE-DAEP | 0.938 | 0.067 | 0.268 | 0.108 | 0.461 | 0.171 | 0.264 | 0.267 | 0.166 |
| AE-PEEDA | 0.201 | 0.060 | 0.086 | 0.066 | 0.101 | 0.061 | 0.134 | 0.107 | 0.000 |
| iAE-PEEDA | 0.000 | 0.000 | 0.000 | 0.000 | 0.000 | 0.000 | 0.000 | 0.000 | 0.000 |
| AE-DPE | 0.098 | 0.084 | 0.239 | 0.087 | 0.138 | 0.112 | 0.246 | 0.120 | 0.053 |
| BPEA | 0.850 | 0.042 | 0.137 | 0.075 | 0.193 | 0.046 | 0.175 | 0.053 | 0.056 |
| Others | 12.032 | 2.444 | 6.821 | 4.133 | 9.534 | 2.987 | 7.006 | 3.146 | 3.176 |
| MEA Conversion, % | 77.91 | 28.64 | 48.59 | 41.59 | 60.59 | 28.29 | 49.91 | 30.83 | 33.03 |
| DETA Conversion, % | 48.20 | 18.14 | 32.92 | 26.27 | 38.96 | 19.71 | 33.35 | 19.75 | 19.71 |
| Acyclic(N4), % | 89.54 | 97.24 | 94.75 | 96.48 | 93.21 | 96.49 | 94.53 | 96.56 | 96.56 |
| Acyclic(N5), % | 85.48 | 92.81 | 91.37 | 94.61 | 91.34 | 89.90 | 89.90 | 86.86 | 93.58 |
| $\Sigma(N5)/\Sigma(N4)$, weight ratio | 0.83 | 0.35 | 0.61 | 0.47 | 0.69 | 0.40 | 0.62 | 0.42 | 0.41 |
| Acyclic(N4)/cyclic ($\leq$=N4), weight ratio | 3.99 | 13.72 | 8.28 | 11.28 | 6.56 | 12.25 | 8.37 | 12.60 | 12.29 |
| | 4.60 | 17.25 | 10.39 | 13.95 | 8.23 | 15.79 | 11.03 | 16.06 | 15.57 |

TABLE V

| Example No. | 57 | 58 | 59 | 60 | 61 | 62 | 63 | 64 | 65 |
|---|---|---|---|---|---|---|---|---|---|
| Catalyst Type | E | E | E | E | E | E | E | E | E |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 3.05 | 3.45 | 3.71 | 3.37 | 3.66 | 4.11 | 3.75 | 3.37 | 3.61 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.701 | 1.330 | 2.175 | 2.857 | 3.642 | 1.575 | 0.790 | 2.998 | 4.045 |
| MEA | 16.452 | 20.045 | 13.804 | 10.226 | 7.809 | 18.066 | 25.597 | 9.273 | 6.909 |
| PIP | 0.640 | 0.536 | 0.952 | 1.209 | 1.520 | 0.606 | 0.260 | 1.165 | 1.515 |
| DETA | 35.879 | 42.232 | 35.213 | 31.459 | 28.823 | 40.057 | 48.800 | 31.599 | 29.253 |
| AEEA | 1.848 | 2.310 | 2.025 | 1.615 | 1.216 | 2.188 | 2.179 | 1.469 | 1.067 |
| AEP | 0.845 | 0.661 | 1.314 | 1.822 | 2.394 | 0.806 | 0.375 | 1.797 | 2.395 |
| HEP | 0.000 | 0.000 | 0.000 | 0.000 | 0.000 | 0.000 | 0.000 | 0.000 | 0.000 |
| TAEA | 1.322 | 1.559 | 1.518 | 1.409 | 1.216 | 1.638 | 1.501 | 1.434 | 1.240 |
| 1-TETA | 11.392 | 12.975 | 14.107 | 14.075 | 13.354 | 13.401 | 10.153 | 13.748 | 13.019 |

TABLE V-continued

| Example No. | 57 | 58 | 59 | 60 | 61 | 62 | 63 | 64 | 65 |
|---|---|---|---|---|---|---|---|---|---|
| DAEP | 0.426 | 0.224 | 0.652 | 1.052 | 1.477 | 0.312 | 0.097 | 1.047 | 1.571 |
| PEEDA | 0.338 | 0.171 | 0.491 | 0.777 | 1.119 | 0.227 | 0.067 | 0.783 | 1.163 |
| DPE | 0.378 | 0.162 | 0.370 | 0.148 | 0.166 | 0.178 | 0.103 | 0.153 | 0.172 |
| AE-TAEA | 2.369 | 2.370 | 3.157 | 3.316 | 3.106 | 2.829 | 1.535 | 3.212 | 3.251 |
| 1-TEPA | 5.829 | 5.299 | 8.163 | 9.154 | 9.766 | 5.998 | 2.509 | 8.811 | 9.487 |
| AE-DAEP | 0.502 | 0.250 | 0.590 | 0.924 | 1.403 | 0.326 | 0.060 | 0.968 | 1.481 |
| AE-PEEDA | 0.347 | 0.087 | 0.124 | 0.292 | 0.486 | 0.090 | 0.044 | 0.282 | 0.455 |
| iAE-PEEDA | 0.000 | 0.000 | 0.000 | 0.000 | 0.000 | 0.000 | 0.000 | 0.000 | 0.000 |
| AE-DPE | 0.232 | 0.275 | 0.287 | 0.246 | 0.088 | 0.181 | 0.082 | 0.038 | 0.044 |
| BPEA | 0.378 | 0.316 | 0.172 | 0.212 | 0.728 | 0.108 | 0.026 | 0.237 | 0.689 |
| Others | 6.553 | 3.689 | 8.018 | 10.689 | 12.800 | 5.245 | 2.365 | 11.008 | 12.985 |
| MEA Conversion, % | 52.34 | 45.74 | 62.87 | 72.31 | 78.98 | 51.01 | 30.96 | 74.50 | 81.34 |
| DETA Conversion, % | 38.38 | 32.23 | 43.85 | 49.50 | 54.02 | 35.61 | 21.97 | 48.49 | 53.19 |
| Acyclic(N4), % | 91.74 | 96.30 | 91.16 | 88.66 | 84.05 | 95.43 | 97.74 | 88.44 | 83.06 |
| Acyclic(N5), % | 84.87 | 89.18 | 90.60 | 88.15 | 82.62 | 92.58 | 94.97 | 88.74 | 82.66 |
| Σ(N5)/Σ(N4), weight ratio | 0.69 | 0.56 | 0.72 | 0.80 | 0.89 | 0.60 | 0.35 | 0.78 | 0.89 |
| Acyclic(N4)/cyclic (<=N4), weight ratio | 4.83 | 8.27 | 4.13 | 3.09 | 2.18 | 7.05 | 12.88 | 3.06 | 2.09 |

TABLE VI

| Example No. | 66 | 67 | 68 | 69 | 70 | 71 | 72 | 73 | 74 |
|---|---|---|---|---|---|---|---|---|---|
| Catalyst Type | F | F | F | F | F | F | F | F | F |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.68 | 3.89 | 3.54 | 3.97 | 4.37 | 3.98 | 3.57 | 3.82 |
| DETA/MEA mole ratio | 0.99 | 0.99 | 0.99 | 0.99 | 0.99 | 0.99 | 0.99 | 0.99 | 0.99 |
| NH₃/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.087 | 0.784 | 1.159 | 1.518 | 1.787 | 0.898 | 0.427 | 1.694 | 2.168 |
| MEA | 18.000 | 23.201 | 17.032 | 13.812 | 11.331 | 21.539 | 28.009 | 12.798 | 9.998 |
| PIP | 0.304 | 0.215 | 0.374 | 0.499 | 0.603 | 0.261 | 0.099 | 0.550 | 0.705 |
| DETA | 38.387 | 48.461 | 41.116 | 37.786 | 35.688 | 46.385 | 52.406 | 37.936 | 35.454 |
| AEEA | 1.924 | 2.613 | 2.539 | 2.224 | 1.893 | 2.489 | 2.034 | 2.026 | 1.642 |
| AEP | 0.449 | 0.342 | 0.517 | 0.696 | 0.879 | 0.393 | 0.244 | 0.797 | 1.019 |
| HEP | 0.000 | 0.000 | 0.000 | 0.000 | 0.000 | 0.000 | 0.000 | 0.000 | 0.000 |
| TAEA | 1.318 | 1.639 | 1.852 | 1.906 | 1.859 | 1.711 | 1.190 | 1.917 | 1.886 |
| 1-TETA | 10.672 | 10.861 | 13.747 | 14.589 | 13.661 | 10.892 | 7.078 | 13.335 | 13.840 |
| DAEP | 0.198 | 0.087 | 0.200 | 0.337 | 0.533 | 0.121 | 0.037 | 0.403 | 0.653 |
| PEEDA | 0.174 | 0.066 | 0.178 | 0.212 | 0.342 | 0.087 | 0.032 | 0.284 | 0.424 |
| DPE | 0.179 | 0.118 | 0.179 | 0.221 | 0.417 | 0.120 | 0.055 | 0.352 | 0.139 |
| AE-TAEA | 2.140 | 1.768 | 3.096 | 3.996 | 4.461 | 2.295 | 1.015 | 3.949 | 4.557 |
| 1-TEPA | 4.234 | 2.982 | 5.888 | 7.317 | 8.157 | 3.420 | 1.361 | 7.182 | 8.348 |
| AE-DAEP | 0.296 | 0.057 | 0.409 | 0.400 | 0.522 | 0.133 | 0.088 | 0.409 | 0.588 |
| AE-PEEDA | 0.088 | 0.000 | 0.334 | 0.106 | 0.146 | 0.036 | 0.000 | 0.096 | 0.134 |
| iAE-PEEDA | 0.000 | 0.000 | 0.000 | 0.000 | 0.000 | 0.000 | 0.000 | 0.000 | 0.000 |
| AE-DPE | 0.160 | 0.104 | 0.269 | 0.268 | 0.263 | 0.116 | 0.063 | 0.216 | 0.185 |
| BPEA | 0.267 | 0.172 | 0.142 | 0.179 | 0.194 | 0.048 | 0.026 | 0.155 | 0.204 |
| Others | 4.394 | 1.773 | 5.061 | 7.143 | 9.034 | 3.187 | 1.556 | 7.761 | 10.098 |
| MEA Conversion, % | 45.31 | 36.86 | 54.05 | 62.75 | 69.21 | 40.96 | 23.12 | 65.04 | 72.98 |
| DETA Conversion, % | 30.85 | 21.83 | 34.25 | 39.59 | 42.51 | 24.63 | 14.72 | 38.57 | 43.21 |
| Acyclic(N4), % | 95.59 | 97.86 | 96.54 | 95.52 | 92.30 | 97.45 | 98.50 | 93.60 | 92.81 |
| Acyclic(N5), % | 88.69 | 93.42 | 88.59 | 92.21 | 91.80 | 94.45 | 93.00 | 92.68 | 92.06 |
| Σ(N5)/Σ(N4), weight ratio | 0.57 | 0.39 | 0.62 | 0.71 | 0.81 | 0.46 | 0.30 | 0.73 | 0.82 |
| Acyclic(N4)/cyclic (<=N4), weight ratio | 9.17 | 15.04 | 10.75 | 8.38 | 5.58 | 12.79 | 17.59 | 6.38 | 5.34 |

TABLE VII

| Example No. | 75 | 76 | 77 | 78 | 79 | 80 | 81 | 82 | 83 |
|---|---|---|---|---|---|---|---|---|---|
| Catalyst Type | G | G | G | G | G | G | G | G | G |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 248.2 | 249.8 | 259.9 | 264.9 | 269.9 | 254.8 | 244.8 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.53 | 3.71 | 3.46 | 3.59 | 3.87 | 2.57 | 2.86 | 3.23 |
| DETA/MEA mole ratio | 0.99 | 0.99 | 0.99 | 0.99 | 0.99 | 0.99 | 0.99 | 0.99 | 0.99 |
| NH₃/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.256 | 0.898 | 1.478 | 1.884 | 2.373 | 1.036 | 0.465 | 1.816 | 2.297 |
| MEA | 25.808 | 27.657 | 23.849 | 20.875 | 18.992 | 27.163 | 30.642 | 19.820 | 18.074 |

TABLE VII-continued

| Example No. | 75 | 76 | 77 | 78 | 79 | 80 | 81 | 82 | 83 |
|---|---|---|---|---|---|---|---|---|---|
| PIP | 0.741 | 0.635 | 1.097 | 1.449 | 1.776 | 0.782 | 0.318 | 1.333 | 1.650 |
| DETA | 46.166 | 50.830 | 44.501 | 41.541 | 37.635 | 48.978 | 54.604 | 40.543 | 39.246 |
| AEEA | 1.262 | 1.412 | 1.399 | 1.264 | 1.114 | 1.392 | 1.370 | 1.307 | 1.228 |
| AEP | 0.698 | 0.614 | 1.115 | 1.609 | 2.034 | 0.761 | 0.370 | 1.447 | 1.897 |
| HEP | 0.000 | 0.000 | 0.000 | 0.000 | 0.000 | 0.000 | 0.000 | 0.000 | 0.000 |
| TAEA | 1.061 | 1.182 | 1.300 | 1.247 | 1.133 | 1.126 | 0.903 | 1.223 | 1.288 |
| 1-TETA | 6.765 | 6.611 | 7.971 | 8.544 | 8.553 | 6.512 | 4.641 | 8.127 | 8.926 |
| DAEP | 0.208 | 0.157 | 0.077 | 0.663 | 0.883 | 0.231 | 0.068 | 0.527 | 0.791 |
| PEEDA | 0.205 | 0.143 | 0.366 | 0.645 | 0.886 | 0.213 | 0.055 | 0.541 | 0.782 |
| DPE | 0.113 | 0.071 | 0.219 | 0.258 | 0.341 | 0.119 | 0.033 | 0.233 | 0.284 |
| AE-TAEA | 1.055 | 1.082 | 1.616 | 1.535 | 1.657 | 1.234 | 0.646 | 1.783 | 1.929 |
| 1-TEPA | 2.631 | 2.675 | 4.495 | 5.280 | 5.850 | 2.897 | 0.093 | 4.793 | 5.840 |
| AE-DAEP | 0.282 | 0.121 | 0.395 | 0.609 | 0.911 | 0.196 | 0.144 | 0.532 | 0.763 |
| AE-PEEDA | 0.292 | 0.151 | 0.092 | 0.119 | 0.165 | 0.038 | 0.053 | 0.122 | 0.135 |
| iAE-PEEDA | 0.000 | 0.000 | 0.000 | 0.000 | 0.000 | 0.000 | 0.000 | 0.000 | 0.000 |
| AE-DPE | 0.145 | 0.056 | 0.248 | 0.182 | 0.222 | 0.075 | 0.051 | 0.226 | 0.172 |
| BPEA | 0.092 | 0.102 | 0.103 | 0.126 | 0.256 | 0.045 | 0.017 | 0.125 | 0.148 |
| Others | 4.080 | 2.114 | 6.330 | 7.633 | 9.871 | 3.590 | 2.398 | 7.053 | 7.859 |
| MEA Conversion, % | 27.62 | 25.05 | 36.44 | 44.22 | 49.24 | 26.50 | 16.41 | 44.75 | 50.95 |
| DETA Conversion, % | 23.25 | 18.34 | 29.70 | 34.20 | 40.37 | 21.43 | 11.69 | 33.00 | 36.86 |
| Acyclic(N4), % | 93.68 | 95.43 | 93.13 | 86.19 | 82.11 | 93.10 | 97.23 | 87.77 | 84.60 |
| Acyclic(N5), % | 81.93 | 89.70 | 87.91 | 86.79 | 82.82 | 92.02 | 73.46 | 86.72 | 86.42 |
| $\Sigma(N5)/\Sigma(N4)$, weight ratio | 0.53 | 0.51 | 0.69 | 0.69 | 0.76 | 0.54 | 0.17 | 0.71 | 0.74 |
| Acyclic(N4)/cyclic ($<=$N4), weight ratio | 3.97 | 4.80 | 3.20 | 2.11 | 1.63 | 3.62 | 6.55 | 2.28 | 1.88 |

TABLE VIII

| Example No. | 84 | 85 | 86 | 87 | 88 | 89 | 90 | 91 | 92 | 93 |
|---|---|---|---|---|---|---|---|---|---|---|
| Catalyst Type | H | H | H | H | H | H | H | H | H | H |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.34 | 5.65 | 6.24 | 6.38 | 8.47 | 6.90 | 6.07 | 5.74 | 6.46 | 5.51 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.699 | 0.991 | 0.581 | 0.845 | 0.904 | 1.637 | 0.332 | 0.557 | 0.575 | 0.259 |
| MEA | 30.881 | 26.979 | 30.239 | 25.449 | 23.586 | 17.207 | 30.424 | 27.661 | 28.796 | 31.430 |
| PIP | 0.175 | 0.376 | 0.190 | 0.382 | 0.461 | 0.971 | 0.111 | 0.252 | 0.248 | 0.099 |
| DETA | 54.402 | 53.966 | 56.223 | 52.550 | 52.679 | 47.929 | 58.899 | 56.255 | 55.809 | 58.323 |
| AEEA | 2.275 | 3.020 | 2.563 | 2.952 | 3.082 | 2.508 | 2.232 | 2.891 | 2.746 | 2.097 |
| AEP | 0.295 | 0.411 | 0.323 | 0.398 | 0.511 | 0.939 | 0.287 | 0.368 | 0.336 | 0.287 |
| HEP | 0.000 | 0.000 | 0.000 | 0.000 | 0.000 | 0.000 | 0.000 | 0.000 | 0.000 | 0.000 |
| TAEA | 0.544 | 0.915 | 0.601 | 0.901 | 1.106 | 1.536 | 0.566 | 0.803 | 0.731 | 0.444 |
| 1-TETA | 3.185 | 5.582 | 3.529 | 5.218 | 6.542 | 9.101 | 3.328 | 4.694 | 4.368 | 2.706 |
| DAEP | 0.103 | 0.030 | 0.056 | 0.111 | 0.131 | 0.332 | 0.046 | 0.086 | 0.060 | 0.023 |
| PEEDA | 0.033 | 0.040 | 0.046 | 0.025 | 0.026 | 0.319 | 0.036 | 0.039 | 0.032 | 0.026 |
| DPE | 0.079 | 0.078 | 0.059 | 0.071 | 0.094 | 0.191 | 0.047 | 0.059 | 0.058 | 0.000 |
| AE-TAEA | 0.120 | 0.479 | 0.160 | 0.566 | 0.782 | 1.819 | 0.164 | 0.345 | 0.340 | 0.110 |
| 1-TEPA | 0.223 | 1.046 | 0.335 | 1.448 | 1.933 | 4.344 | 0.305 | 0.748 | 0.777 | 0.175 |
| AE-DAEP | 0.054 | 0.000 | 0.000 | 0.035 | 0.058 | 0.101 | 0.000 | 0.000 | 0.000 | 0.000 |
| AE-PEEDA | 0.000 | 0.043 | 0.000 | 0.307 | 0.000 | 0.047 | 0.062 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.085 | 0.000 | 0.053 | 0.000 | 0.000 | 0.108 | 0.000 | 0.000 | 0.000 | 0.098 |
| BPEA | 0.000 | 0.060 | 0.000 | 0.078 | 0.052 | 0.141 | 0.000 | 0.000 | 0.000 | 0.000 |
| Others | 1.439 | 1.936 | 1.433 | 2.104 | 2.736 | 5.251 | 1.312 | 1.757 | 1.538 | 0.936 |
| MEA Conversion, % | 13.32 | 26.12 | 16.89 | 28.40 | 35.09 | 53.51 | 17.91 | 24.54 | 21.17 | 13.94 |
| DETA Conversion, % | 9.48 | 12.39 | 8.40 | 12.35 | 14.06 | 23.24 | 5.79 | 9.02 | 9.43 | 5.33 |
| Acyclic(N4), % | 94.50 | 97.75 | 96.19 | 96.70 | 96.80 | 92.65 | 96.76 | 96.72 | 97.11 | 98.43 |
| Acyclic(N5), % | 71.06 | 93.57 | 90.33 | 92.98 | 96.07 | 93.91 | 88.20 | 100 | 100 | 74.27 |
| $\Sigma(N5)/\Sigma(N4)$, weight ratio | 0.12 | 0.24 | 0.12 | 0.34 | 0.35 | 0.57 | 0.13 | 0.19 | 0.21 | 0.12 |
| Acyclic(N4)/cyclic ($<=$N4), weight ratio | 5.42 | 6.93 | 6.10 | 6.18 | 6.23 | 3.86 | 7.36 | 6.81 | 6.91 | 7.21 |
| Example No. | 94 | 95 | 96 | 97 | 98 | 99 | 100 | 101 | 102 | 103 |
| Catalyst Type | H | H | H | H | H | H | H | H | H | H |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.9 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.31 | 5.47 | 5.77 | 6.00 | 6.06 | 6.55 | 5.78 | 5.50 | 5.21 | 5.66 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |

TABLE VIII-continued

| Crude product composition. wt. % | | | | | | | | | | |
|---|---|---|---|---|---|---|---|---|---|---|
| EDA | 0.745 | 0.944 | 0.594 | 0.847 | 1.030 | 1.615 | 0.327 | 0.590 | 0.591 | 0.329 |
| MEA | 30.660 | 27.781 | 30.325 | 25.425 | 24.014 | 17.349 | 31.104 | 27.787 | 28.697 | 31.814 |
| PIP | 0.148 | 0.317 | 0.168 | 0.346 | 0.455 | 0.912 | 0.099 | 0.228 | 0.218 | 0.088 |
| DETA | 56.688 | 54.036 | 55.722 | 53.130 | 52.088 | 48.017 | 59.117 | 56.024 | 55.945 | 58.205 |
| AEEA | 2.475 | 3.096 | 2.580 | 3.089 | 3.100 | 2.630 | 2.204 | 2.899 | 2.826 | 2.086 |
| AEP | 0.299 | 0.420 | 0.298 | 0.379 | 0.470 | 0.914 | 0.261 | 0.367 | 0.346 | 0.274 |
| HEP | 0.000 | 0.000 | 0.000 | 0.000 | 0.000 | 0.000 | 0.000 | 0.000 | 0.000 | 0.000 |
| TAEA | 0.588 | 0.879 | 0.588 | 0.969 | 1.022 | 1.530 | 0.489 | 0.798 | 0.714 | 0.410 |
| 1-TETA | 3.553 | 5.158 | 3.445 | 5.562 | 5.935 | 8.838 | 2.904 | 4.702 | 4.162 | 2.520 |
| DAEP | 0.105 | 0.125 | 0.051 | 0.095 | 0.114 | 0.319 | 0.031 | 0.066 | 0.065 | 0.018 |
| PEEDA | 0.026 | 0.043 | 0.060 | 0.030 | 0.042 | 0.332 | 0.042 | 0.036 | 0.027 | 0.022 |
| DPE | 0.055 | 0.072 | 0.073 | 0.088 | 0.099 | 0.211 | 0.040 | 0.071 | 0.055 | 0.000 |
| AE-TAEA | 0.066 | 0.361 | 0.137 | 0.513 | 0.679 | 1.746 | 0.102 | 0.299 | 0.261 | 0.078 |
| 1-TEPA | 0.144 | 0.806 | 0.322 | 1.126 | 1.742 | 3.970 | 0.183 | 0.650 | 0.621 | 0.101 |
| AE-DAEP | 0.068 | 0.000 | 0.000 | 0.030 | 0.037 | 0.180 | 0.000 | 0.000 | 0.000 | 0.000 |
| AE-PEEDA | 0.000 | 0.000 | 0.000 | 0.000 | 0.056 | 0.080 | 0.164 | 0.030 | 0.092 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.058 | 0.000 | 0.000 | 0.000 | 0.000 | 0.000 | 0.000 | 0.154 |
| BPEA | 0.000 | 0.000 | 0.000 | 0.000 | 0.056 | 0.046 | 0.093 | 0.000 | 0.000 | 0.000 |
| Others | 1.371 | 1.735 | 1.521 | 2.443 | 2.782 | 5.517 | 1.044 | 1.685 | 1.503 | 0.926 |
| MEA Conversion, % | 16.17 | 23.60 | 16.23 | 29.21 | 33.10 | 52.96 | 15.90 | 23.93 | 21.18 | 12.82 |
| DETA Conversion, % | 8.12 | 11.91 | 8.75 | 12.31 | 13.98 | 22.83 | 5.25 | 9.08 | 8.91 | 5.45 |
| Acyclic(N4), % | 95.65 | 96.13 | 95.62 | 96.81 | 96.43 | 92.31 | 96.73 | 96.92 | 97.05 | 98.63 |
| Acyclic(N5), % | 75.52 | 100.00 | 88.65 | 94.91 | 94.51 | 94.17 | 63.39 | 96.93 | 90.51 | 53.84 |
| $\Sigma(N5)/\Sigma(N4)$, weight ratio | 0.06 | 0.18 | 0.12 | 0.25 | 0.35 | 0.54 | 0.12 | 0.17 | 0.19 | 0.11 |
| Acyclic(N4)/cyclic ($\leq$ =N4), weight ratio | 6.50 | 6.15 | 6.19 | 6.93 | 5.88 | 3.85 | 7.13 | 7.13 | 6.83 | 7.26 |

TABLE IX

| Example No. | 104 | 105 | 106 | 107 | 108 | 109 | 110 | 111 | 112 |
|---|---|---|---|---|---|---|---|---|---|
| Catalyst Type | I | I | I | I | I | I | I | I | I |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 265.4 | 274.9 | 270.4 | 280.5 |
| Time on organics, hrs. | 49 | 69 | 73 | 92 | 117 | 141 | 145 | 164 | 168 |
| Duration of run, hrs. | 2 | 2 | 2 | 2 | 2 | 2 | 2 | 2 | 2 |
| MEA SV, gmol/hr/kgcat | 6.27 | 5.79 | 6.32 | 6.13 | 5.94 | 5.89 | 5.95 | 6.07 | 6.15 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.646 | 0.996 | 1.453 | 0.520 | 0.455 | 1.300 | 2.007 | 1.580 | 2.469 |
| MEA | 26.654 | 23.680 | 16.639 | 28.140 | 28.547 | 22.094 | 15.810 | 19.303 | 11.900 |
| PIP | 0.159 | 0.228 | 0.386 | 0.099 | 0.087 | 0.283 | 0.468 | 0.350 | 0.631 |
| DETA | 51.837 | 47.809 | 41.131 | 53.445 | 54.624 | 47.199 | 40.533 | 44.569 | 38.430 |
| AEEA | 2.147 | 2.219 | 2.091 | 1.899 | 1.991 | 2.285 | 1.858 | 2.050 | 1.358 |
| AEP | 0.366 | 0.391 | 0.584 | 0.286 | 0.291 | 0.441 | 0.652 | 0.586 | 1.003 |
| HEP | 0.000 | 0.000 | 0.000 | 0.000 | 0.000 | 0.000 | 0.000 | 0.000 | 0.000 |
| TAEA | 1.404 | 1.960 | 2.022 | 1.297 | 1.245 | 1.889 | 1.973 | 1.833 | 2.102 |
| 1-TETA | 9.038 | 10.383 | 12.919 | 7.486 | 7.272 | 11.110 | 12.264 | 11.044 | 12.373 |
| DAEP | 0.091 | 0.136 | 0.267 | 0.047 | 0.050 | 0.144 | 0.296 | 0.227 | 0.594 |
| PEEDA | 0.049 | 0.069 | 0.074 | 0.030 | 0.025 | 0.066 | 0.089 | 0.070 | 0.162 |
| DPE | 0.102 | 0.194 | 0.327 | 0.078 | 0.085 | 0.208 | 0.379 | 0.309 | 0.460 |
| AE-TAEA | 1.004 | 1.822 | 3.107 | 0.781 | 0.689 | 1.905 | 3.070 | 2.472 | 3.435 |
| 1-TEPA | 1.515 | 2.906 | 5.194 | 1.189 | 1.007 | 2.936 | 5.147 | 4.012 | 5.957 |
| AE-DAEP | 0.043 | 0.106 | 0.253 | 0.000 | 0.000 | 0.051 | 0.422 | 0.311 | 0.280 |
| AE-PEEDA | 0.000 | 0.000 | 0.112 | 0.000 | 0.000 | 0.000 | 0.118 | 0.082 | 0.131 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.240 | 0.000 | 0.000 | 0.000 | 0.343 | 0.373 | 0.088 |
| BPEA | 0.085 | 0.242 | 0.492 | 0.078 | 0.000 | 0.281 | 0.275 | 0.212 | 0.296 |
| Others | 1.551 | 4.275 | 6.422 | 1.397 | 1.017 | 3.348 | 7.308 | 5.745 | 11.413 |
| MEA Conversion, % | 27.88 | 35.83 | 54.96 | 23.58 | 22.81 | 40.26 | 56.94 | 48.09 | 67.96 |
| DETA Conversion, % | 16.85 | 23.20 | 34.01 | 13.96 | 12.53 | 24.35 | 34.55 | 28.95 | 38.66 |
| Acyclic(N4), % | 97.71 | 96.35 | 95.71 | 98.25 | 98.13 | 96.87 | 94.89 | 95.49 | 92.24 |
| Acyclic(N5), % | 95.12 | 93.12 | 88.30 | 96.16 | 100.00 | 93.55 | 87.63 | 86.86 | 92.18 |
| $\Sigma(N5)/\Sigma(N4)$, weight ratio | 0.24 | 0.46 | 0.60 | 0.22 | 0.19 | 0.38 | 0.62 | 0.55 | 0.64 |
| Acyclic(N4)/cyclic ($\leq$ =N4), weight ratio | 13.55 | 10.36 | 9.11 | 16.20 | 15.74 | 11.35 | 7.54 | 8.33 | 5.07 |

| Example No. | 113 | 114 | 115 | 116 | 117 | 118 |
|---|---|---|---|---|---|---|
| Catalyst Type | I | I | I | I | I | I |
| Catalyst weight, gm | 50 | 50 | 50 | 50 | 50 | 50 |
| Pressure, psig | 600 | 600 | 600 | 600 | 600 | 600 |
| Temperature, °C. | 250.3 | 255.6 | 260.5 | 270.5 | 250.4 | 260.4 |
| Time on organics, hrs. | 187 | 192 | 212 | 216 | 235 | 240 |
| Duration of run, hrs. | 2 | 2 | 2 | 2 | 2 | 2 |
| MEA SV, gmol/hr/kgcat | 5.94 | 6.33 | 5.99 | 6.27 | 5.90 | 6.53 |

TABLE IX-continued

| | | | | | | |
|---|---|---|---|---|---|---|
| DETA/MEA mole ratio | 0.99 | 0.99 | 0.99 | 0.99 | 0.99 | 0.99 |
| NH3/MEA mole ratio | 5.98 | 5.98 | 5.98 | 5.98 | 5.98 | 5.98 |
| Crude product composition, wt. % | | | | | | |
| EDA | 0.514 | 0.593 | 0.846 | 1.480 | 0.481 | 0.783 |
| MEA | 26.000 | 26.235 | 23.790 | 20.254 | 28.197 | 23.941 |
| PIP | 0.090 | 0.105 | 0.152 | 0.302 | 0.082 | 0.131 |
| DETA | 54.672 | 54.260 | 52.317 | 46.643 | 55.162 | 53.334 |
| AEEA | 1.820 | 1.991 | 2.249 | 2.223 | 1.878 | 2.190 |
| AEP | 0.502 | 0.388 | 0.389 | 0.514 | 0.325 | 0.363 |
| HEP | 0.000 | 0.000 | 0.000 | 0.000 | 0.000 | 0.000 |
| TAEA | 1.571 | 1.456 | 1.611 | 1.878 | 1.195 | 1.609 |
| l-TETA | 7.704 | 7.909 | 9.027 | 10.859 | 6.705 | 8.957 |
| DAEP | 0.245 | 0.133 | 0.114 | 0.191 | 0.060 | 0.105 |
| PEEDA | 0.053 | 0.083 | 0.108 | 0.084 | 0.049 | 0.099 |
| DPE | 0.106 | 0.143 | 0.171 | 0.268 | 0.122 | 0.180 |
| AE-TAEA | 0.748 | 0.777 | 1.110 | 2.057 | 0.628 | 1.062 |
| l-TEPA | 0.976 | 1.117 | 1.577 | 3.217 | 0.791 | 1.486 |
| AE-DAEP | 0.045 | 0.028 | 0.041 | 0.083 | 0.000 | 0.032 |
| AE-PEEDA | 0.151 | 0.102 | 0.121 | 0.043 | 0.195 | 0.055 |
| iAE-PEEDA | 0.000 | 0.000 | 0.000 | 0.000 | 0.000 | 0.000 |
| AE-DPE | 0.000 | 0.000 | 0.034 | 0.272 | 0.000 | 0.000 |
| BPEA | 0.000 | 0.000 | 0.052 | 0.156 | 0.000 | 0.047 |
| Others | 2.165 | 1.873 | 2.601 | 4.845 | 1.692 | 2.559 |
| MEA Conversion, % | 30.21 | 29.38 | 35.76 | 45.44 | 24.03 | 35.94 |
| DETA Conversion, % | 13.00 | 13.42 | 16.25 | 25.48 | 11.90 | 15.05 |
| Acyclic(N4), % | 95.80 | 96.29 | 96.42 | 95.89 | 97.14 | 96.48 |
| Acyclic(N5), % | 89.71 | 93.54 | 91.50 | 90.44 | 87.86 | 94.96 |
| Σ(N5)/Σ(N4), weight ratio | 0.19 | 0.20 | 0.26 | 0.43 | 0.19 | 0.24 |
| Acyclic(N4)/cyclic (<=N4), weight ratio | 9.28 | 10.96 | 11.35 | 9.35 | 12.35 | 12.00 |

TABLE X

| Example No. | 119 | 120 | 121 | 122 | 123 | 124 | 125 | 126 | 127 |
|---|---|---|---|---|---|---|---|---|---|
| Catalyst Type | J | J | J | J | J | J | J | J | J |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 285.4 | 274.9 | 270.4 | 280.5 |
| Time on organics, hrs. | 4 | 24 | 28 | 47 | 72 | 96 | 100 | 120 | 124 |
| Duration of run, hrs. | 2 | 2 | 2 | 2 | 2 | 2 | 2 | 2 | 2 |
| MEA SV, gmol/hr/kgcat | 6.18 | 2.34 | 5.82 | 5.84 | 5.69 | 5.51 | 5.75 | 5.84 | 5.73 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.917 | 1.897 | 2.108 | 0.590 | 0.434 | 1.245 | 2.140 | 1.671 | 2.735 |
| MEA | 25.662 | 20.472 | 16.778 | 28.012 | 27.367 | 22.431 | 16.450 | 20.118 | 12.411 |
| PIP | 0.380 | 0.881 | 1.077 | 0.268 | 0.212 | 0.674 | 1.189 | 0.858 | 1.490 |
| DETA | 50.521 | 43.321 | 39.423 | 52.720 | 54.768 | 47.275 | 40.189 | 45.395 | 37.922 |
| AEEA | 2.344 | 2.643 | 1.892 | 2.035 | 2.217 | 2.374 | 1.773 | 2.194 | 1.405 |
| AEP | 0.461 | 0.807 | 1.116 | 0.369 | 0.357 | 0.675 | 1.147 | 0.885 | 1.698 |
| HEP | 0.000 | 0.000 | 0.000 | 0.000 | 0.000 | 0.000 | 0.000 | 0.000 | 0.000 |
| TAEA | 1.220 | 1.437 | 1.468 | 1.065 | 1.114 | 1.421 | 1.395 | 1.422 | 1.542 |
| l-TETA | 9.448 | 11.215 | 12.082 | 7.243 | 7.568 | 10.105 | 11.100 | 10.492 | 11.616 |
| DAEP | 0.115 | 0.274 | 0.481 | 0.069 | 0.062 | 0.210 | 0.438 | 0.310 | 0.808 |
| PEEDA | 0.063 | 0.175 | 0.071 | 0.039 | 0.033 | 0.056 | 0.067 | 0.060 | 0.135 |
| DPE | 0.116 | 0.171 | 0.245 | 0.071 | 0.076 | 0.182 | 0.299 | 0.250 | 0.107 |
| AE-TAEA | 1.057 | 1.803 | 2.308 | 0.672 | 0.602 | 1.534 | 2.154 | 1.795 | 2.349 |
| l-TEPA | 2.317 | 4.207 | 5.775 | 1.422 | 1.227 | 3.460 | 5.412 | 4.306 | 6.191 |
| AE-DAEP | 0.039 | 0.195 | 0.407 | 0.000 | 0.029 | 0.142 | 0.610 | 0.314 | 0.399 |
| AE-PEEDA | 0.000 | 0.037 | 0.039 | 0.000 | 0.000 | 0.000 | 0.119 | 0.043 | 0.254 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.042 | 0.000 | 0.000 | 0.000 | 0.184 | 0.112 | 0.044 |
| BPEA | 0.141 | 0.281 | 0.355 | 0.082 | 0.065 | 0.187 | 0.205 | 0.132 | 0.238 |
| Others | 1.669 | 3.555 | 5.886 | 1.375 | 1.291 | 3.662 | 7.822 | 4.954 | 11.756 |
| MEA Conversion, % | 30.62 | 43.66 | 53.48 | 23.36 | 26.31 | 39.42 | 55.00 | 45.87 | 66.59 |
| DETA Conversion, % | 19.04 | 29.32 | 35.21 | 14.49 | 12.58 | 24.32 | 34.91 | 27.60 | 39.49 |
| Acyclic(N4), % | 97.30 | 95.31 | 94.43 | 97.87 | 98.05 | 96.24 | 93.94 | 95.04 | 92.59 |
| Acyclic(N5), % | 94.89 | 92.10 | 90.54 | 96.19 | 95.07 | 93.80 | 87.10 | 90.99 | 90.10 |
| Σ(N5)/Σ(N4), weight ratio | 0.32 | 0.49 | 0.62 | 0.25 | 0.21 | 0.44 | 0.65 | 0.53 | 0.66 |
| Acyclic(N4)/cyclic (<=N4), weight ratio | 9.37 | 5.47 | 4.52 | 10.14 | 11.70 | 6.40 | 3.97 | 5.03 | 3.10 |

| Example No. | 128 | 129 | 130 | 131 | 132 | 133 |
|---|---|---|---|---|---|---|
| Catalyst Type | J | J | J | J | J | J |
| Catalyst weight, gm | 50 | 50 | 50 | 50 | 50 | 50 |
| Pressure, psig | 600 | 600 | 600 | 600 | 600 | 600 |
| Temperature, °C. | 250.3 | 255.6 | 260.5 | 270.5 | 250.4 | 260.4 |
| Time on organics, hrs. | 143 | 148 | 168 | 172 | 191 | 196 |

TABLE X-continued

| | | | | | | |
|---|---|---|---|---|---|---|
| Duration of run, hrs. | 2 | 2 | 2 | 2 | 2 | 2 |
| MEA SV, gmol/hr/kgcat | 5.72 | 6.20 | 5.68 | 6.10 | 5.61 | 6.22 |
| DETA/MEA mole ratio | 0.99 | 0.99 | 0.99 | 0.99 | 0.99 | 0.99 |
| NH3/MEA mole ratio | 5.98 | 5.98 | 5.98 | 5.98 | 5.98 | 5.98 |
| Crude product composition, wt. % | | | | | | |
| EDA | 0.568 | 0.601 | 0.717 | 1.279 | 0.432 | 0.659 |
| MEA | 27.232 | 27.065 | 22.943 | 20.079 | 28.096 | 24.621 |
| PIP | 0.215 | 0.248 | 0.334 | 0.685 | 0.190 | 0.305 |
| DETA | 54.809 | 54.903 | 54.289 | 45.849 | 56.154 | 54.216 |
| AEEA | 1.865 | 2.067 | 2.397 | 2.218 | 1.939 | 2.262 |
| AEP | 0.495 | 0.410 | 0.506 | 0.739 | 0.377 | 0.454 |
| HEP | 0.000 | 0.000 | 0.000 | 0.000 | 0.000 | 0.000 |
| TAEA | 1.241 | 1.085 | 1.426 | 1.382 | 0.995 | 1.248 |
| 1-TETA | 7.018 | 6.914 | 8.559 | 9.775 | 6.269 | 7.933 |
| DAEP | 0.201 | 0.100 | 0.168 | 0.247 | 0.071 | 0.112 |
| PEEDA | 0.041 | 0.070 | 0.067 | 0.081 | 0.058 | 0.082 |
| DPE | 0.098 | 0.111 | 0.138 | 0.256 | 0.116 | 0.155 |
| AE-TAEA | 0.572 | 0.555 | 0.788 | 1.643 | 0.476 | 0.783 |
| 1-TEPA | 0.960 | 1.063 | 1.605 | 3.662 | 0.771 | 1.561 |
| AE-DAEP | 0.051 | 0.032 | 0.048 | 0.231 | 0.000 | 0.049 |
| AE-PEEDA | 0.060 | 0.172 | 0.043 | 0.121 | 0.267 | 0.041 |
| iAE-PEEDA | 0.000 | 0.000 | 0.000 | 0.000 | 0.000 | 0.000 |
| AE-DPE | 0.000 | 0.000 | 0.000 | 0.398 | 0.000 | 0.000 |
| BPEA | 0.000 | 0.000 | 0.093 | 0.146 | 0.000 | 0.100 |
| Others | 2.205 | 1.668 | 2.622 | 6.639 | 1.610 | 2.481 |
| MEA Conversion, % | 26.89 | 26.88 | 38.41 | 46.08 | 24.52 | 33.90 |
| DETA Conversion, % | 12.77 | 12.07 | 13.61 | 27.01 | 10.57 | 13.72 |
| Acyclic(N4), % | 96.03 | 96.59 | 96.39 | 95.01 | 96.71 | 96.32 |
| Acyclic(N5), % | 93.16 | 88.76 | 92.80 | 85.52 | 82.30 | 92.41 |
| Σ(N5)/Σ(N4), weight ratio | 0.19 | 0.22 | 0.24 | 0.52 | 0.20 | 0.26 |
| Acyclic(N4)/cyclic (<=N4), weight ratio | 7.85 | 8.50 | 8.21 | 5.55 | 8.91 | 8.26 |

TABLE XI

| Example No. | 134 | 135 | 136 | 137 | 138 | 139 | 140 | 141 | 142 |
|---|---|---|---|---|---|---|---|---|---|
| Catalyst Type | K | K | K | K | K | K | K | K | K |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 285.4 | 274.9 | 270.4 | 280.5 |
| Time on organics, hrs. | 4 | 24 | 28 | 47 | 72 | 96 | 100 | 120 | 124 |
| Duration of run, hrs. | 2 | 2 | 2 | 2 | 2 | 2 | 2 | 2 | 2 |
| MEA SV, gmol/hr/kgcat | 5.91 | 5.22 | 5.79 | 5.68 | 5.01 | 4.83 | 3.20 | 4.69 | 4.67 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition. wt. % | | | | | | | | | |
| EDA | 1.242 | 1.425 | 2.314 | 0.692 | 0.693 | 1.556 | 2.532 | 2.046 | 2.610 |
| MEA | 24.360 | 19.503 | 13.469 | 26.303 | 26.975 | 19.666 | 10.987 | 15.532 | 8.187 |
| PIP | 0.265 | 0.346 | 0.627 | 0.143 | 0.124 | 0.340 | 0.644 | 0.486 | 0.714 |
| DETA | 47.368 | 41.906 | 36.625 | 50.994 | 52.751 | 43.552 | 35.351 | 40.568 | 37.477 |
| AEEA | 2.338 | 2.228 | 1.775 | 2.093 | 2.109 | 2.236 | 1.595 | 2.030 | 1.250 |
| AEP | 0.444 | 0.513 | 0.933 | 0.336 | 0.320 | 0.511 | 0.884 | 0.729 | 1.333 |
| HEP | 0.000 | 0.000 | 0.000 | 0.000 | 0.000 | 0.000 | 0.000 | 0.000 | 0.000 |
| TAEA | 1.585 | 1.779 | 1.946 | 1.465 | 1.421 | 1.853 | 1.907 | 1.979 | 2.217 |
| 1-TETA | 10.818 | 11.971 | 13.853 | 8.981 | 8.541 | 11.616 | 12.837 | 13.039 | 13.746 |
| DAEP | 0.137 | 0.201 | 0.508 | 0.073 | 0.066 | 0.184 | 0.434 | 0.315 | 0.805 |
| PEEDA | 0.048 | 0.063 | 0.083 | 0.041 | 0.045 | 0.070 | 0.105 | 0.089 | 0.181 |
| DPE | 0.147 | 0.053 | 0.357 | 0.113 | 0.106 | 0.275 | 0.379 | 0.354 | 0.142 |
| AE-TAEA | 1.536 | 2.197 | 3.601 | 1.105 | 0.931 | 2.462 | 3.448 | 3.044 | 3.487 |
| 1-TEPA | 2.585 | 3.750 | 6.842 | 1.710 | 1.407 | 4.084 | 6.236 | 5.278 | 6.468 |
| AE-DAEP | 0.039 | 0.075 | 0.609 | 0.000 | 0.000 | 0.281 | 0.507 | 0.443 | 0.547 |
| AE-PEEDA | 0.000 | 0.041 | 0.143 | 0.000 | 0.040 | 0.099 | 0.122 | 0.116 | 0.102 |
| iAE-PEEDA | 0.000 | 0.000 | 0.000 | 0.000 | 0.000 | 0.000 | 0.000 | 0.000 | 0.000 |
| AE-DPE | 0.000 | 0.108 | 0.388 | 0.000 | 0.000 | 0.319 | 0.127 | 0.215 | 0.099 |
| BPEA | 0.201 | 0.347 | 0.305 | 0.127 | 0.079 | 0.340 | 0.272 | 0.259 | 0.272 |
| Others | 2.750 | 3.474 | 9.064 | 1.636 | 1.564 | 5.577 | 8.946 | 7.208 | 12.055 |
| MEA Conversion, % | 33.99 | 44.31 | 63.83 | 28.21 | 27.29 | 47.03 | 68.48 | 58.05 | 77.82 |
| DETA Conversion, % | 23.91 | 29.07 | 41.70 | 17.49 | 15.71 | 30.46 | 39.88 | 35.04 | 39.81 |
| Acyclic(N4), % | 97.38 | 97.73 | 94.33 | 97.86 | 97.84 | 96.20 | 94.12 | 95.18 | 93.39 |
| Acyclic(N5), % | 94.47 | 91.20 | 87.83 | 95.68 | 95.12 | 86.28 | 90.39 | 88.94 | 90.68 |
| Σ(N5)/Σ(N4), weight ratio | 0.34 | 0.46 | 0.70 | 0.27 | 0.24 | 0.54 | 0.68 | 0.59 | 0.64 |
| Acyclic(N4)/cyclic (<=N4), weight ratio | 11.89 | 11.66 | 6.29 | 14.74 | 15.00 | 9.73 | 6.02 | 7.59 | 5.02 |

| Example No. | 143 | 144 | 145 | 146 | 147 | 148 |
|---|---|---|---|---|---|---|
| Catalyst Type | K | K | K | K | K | K |
| Catalyst weight, gm | 50 | 50 | 50 | 50 | 50 | 50 |
| Pressure, psig | 600 | 600 | 600 | 600 | 600 | 600 |

TABLE XI-continued

| | | | | | | |
|---|---|---|---|---|---|---|
| Temperature, °C. | 250.3 | 255.6 | 260.5 | 270.5 | 250.4 | 260.4 |
| Time on organics, hrs. | 143 | 148 | 168 | 172 | 191 | 196 |
| Duration of run, hrs. | 2 | 2 | 2 | 2 | 2 | 2 |
| MEA SV, gmol/hr/kgcat | 4.55 | 4.85 | 5.47 | 5.78 | 5.58 | 5.91 |
| DETA/MEA mole ratio | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 |
| Crude product composition, wt. % | | | | | | |
| EDA | 0.781 | 0.770 | 0.851 | 1.497 | 0.588 | 1.026 |
| MEA | 25.538 | 22.350 | 20.873 | 16.503 | 25.282 | 24.673 |
| PIP | 0.126 | 0.140 | 0.170 | 0.328 | 0.089 | 0.177 |
| DETA | 52.133 | 52.645 | 51.089 | 44.349 | 55.299 | 51.223 |
| AEEA | 2.040 | 2.312 | 2.326 | 2.193 | 2.078 | 2.224 |
| AEP | 0.426 | 0.428 | 0.436 | 0.591 | 0.356 | 0.443 |
| HEP | 0.000 | 0.000 | 0.000 | 0.000 | 0.000 | 0.000 |
| TAEA | 1.593 | 1.735 | 1.861 | 1.981 | 1.469 | 1.571 |
| 1-TETA | 8.770 | 9.724 | 10.271 | 11.974 | 8.218 | 9.145 |
| DAEP | 0.153 | 0.159 | 0.161 | 0.253 | 0.106 | 0.115 |
| PEEDA | 0.049 | 0.112 | 0.117 | 0.133 | 0.097 | 0.112 |
| DPE | 0.140 | 0.171 | 0.192 | 0.320 | 0.142 | 0.165 |
| AE-TAEA | 1.025 | 1.128 | 1.380 | 2.468 | 0.743 | 1.139 |
| 1-TEPA | 1.452 | 1.623 | 2.028 | 4.244 | 0.949 | 1.722 |
| AE-DAEP | 0.053 | 0.044 | 0.047 | 0.312 | 0.000 | 0.000 |
| AE-PEEDA | 0.079 | 0.041 | 0.037 | 0.094 | 0.106 | 0.000 |
| iAE-PEEDA | 0.000 | 0.000 | 0.000 | 0.000 | 0.000 | 0.000 |
| AE-DPE | 0.000 | 0.000 | 0.000 | 0.050 | 0.000 | 0.000 |
| BPEA | 0.000 | 0.100 | 0.106 | 0.197 | 0.000 | 0.030 |
| Others | 2.433 | 2.776 | 3.266 | 6.788 | 1.812 | 2.887 |
| MEA Conversion, % | 31.14 | 39.18 | 43.37 | 55.46 | 32.14 | 33.50 |
| DETA Conversion, % | 16.67 | 15.95 | 17.84 | 29.04 | 12.01 | 18.16 |
| Acyclic(N4), % | 96.78 | 96.26 | 96.26 | 95.17 | 96.54 | 96.46 |
| Acyclic(N5), % | 94.89 | 93.64 | 94.69 | 91.17 | 94.09 | 98.95 |
| Σ(N5)/Σ(N4), weight ratio | 0.24 | 0.24 | 0.28 | 0.50 | 0.17 | 0.26 |
| Acyclic(N4)/cyclic (<=N4), weight ratio | 11.55 | 11.30 | 11.24 | 8.57 | 12.22 | 10.56 |

TABLE XII

| Example No. | 149 | 150 | 151 | 152 | 153 | 154 | 155 | 156 | 157 | 158 | 159 |
|---|---|---|---|---|---|---|---|---|---|---|---|
| Catalyst Type | L | L | L | L | L | L | L | L | L | L | L |
| Catalyst weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.3 | 259.6 | 270.3 | 264.7 | 274.8 | 280.3 | 285.1 | 260.4 | 270.3 | 250.7 | 250.8 |
| Time on organics, hrs. | 4 | 24 | 28 | 48 | 52 | 72 | 76 | 86 | 100 | 119.7 | 144.5 |
| Duration of run, hrs. | 2 | 2 | 2 | 2 | 2 | 2 | 2 | 2 | 2 | 2 | 2 |
| MEA SV, gmol/hr/kgcat | 6.40 | 6.33 | 6.28 | 5.72 | 6.02 | 5.58 | 5.65 | 6.24 | 6.17 | 6.94 | 5.93 |
| DETA/MEA mole ratio | 0.99 | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 0.770 | 0.980 | 1.583 | 1.111 | 1.832 | 2.142 | 3.301 | 0.774 | 1.198 | 0.345 | 0.350 |
| MEA | 25.827 | 23.440 | 17.219 | 22.571 | 16.310 | 16.564 | 10.045 | 27.643 | 21.820 | 30.552 | 30.853 |
| PIP | 0.276 | 0.393 | 0.662 | 0.422 | 0.751 | 0.950 | 1.442 | 0.265 | 0.454 | 0.111 | 0.096 |
| DETA | 51.636 | 48.836 | 42.304 | 48.278 | 40.898 | 42.099 | 35.503 | 52.572 | 47.132 | 55.797 | 55.617 |
| AEEA | 2.334 | 2.504 | 2.372 | 2.475 | 2.126 | 1.936 | 1.055 | 2.172 | 2.317 | 1.696 | 1.611 |
| AEP | 0.412 | 0.494 | 0.838 | 0.522 | 0.865 | 0.963 | 1.612 | 0.359 | 0.551 | 0.258 | 0.247 |
| HEP | 0.000 | 0.000 | 0.000 | 0.000 | 0.000 | 0.000 | 0.000 | 0.000 | 0.000 | 0.000 | 0.000 |
| TAEA | 1.110 | 1.332 | 1.599 | 1.416 | 1.525 | 1.379 | 1.308 | 1.011 | 1.348 | 0.717 | 0.639 |
| 1-TETA | 8.696 | 10.460 | 12.736 | 10.690 | 12.202 | 11.061 | 11.624 | 7.027 | 9.767 | 4.893 | 4.363 |
| DAEP | 0.101 | 0.165 | 0.378 | 0.173 | 0.369 | 0.370 | 0.792 | 0.081 | 0.178 | 0.044 | 0.039 |
| PEEDA | 0.489 | 0.055 | 0.252 | 0.693 | 0.263 | 0.286 | 0.651 | 0.025 | 0.122 | 0.023 | 0.032 |
| DPE | 0.112 | 0.134 | 0.073 | 0.039 | 0.086 | 0.085 | 0.110 | 0.079 | 0.180 | 0.004 | 0.052 |
| AE-TAEA | 0.841 | 1.303 | 2.375 | 1.359 | 2.466 | 2.153 | 2.771 | 0.689 | 1.489 | 0.308 | 0.099 |
| 1-TEPA | 1.854 | 3.003 | 5.582 | 3.165 | 5.909 | 5.377 | 7.397 | 1.584 | 3.350 | 0.591 | 0.239 |
| AE-DAEP | 0.000 | 0.051 | 0.359 | 0.070 | 0.646 | 0.658 | 0.827 | 0.000 | 0.171 | 0.000 | 0.342 |
| AE-PEEDA | 0.000 | 0.000 | 0.040 | 0.031 | 0.109 | 0.115 | 0.423 | 0.032 | 0.042 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.112 | 0.049 | 0.000 | 0.057 | 0.476 | 0.079 | 0.000 | 0.000 | 0.000 | 0.045 |
| BPEA | 0.093 | 0.263 | 0.619 | 0.150 | 0.427 | 0.359 | 0.296 | 0.036 | 0.063 | 0.000 | 0.000 |
| Others | 1.692 | 2.457 | 4.961 | 2.959 | 6.639 | 6.450 | 12.385 | 2.004 | 3.510 | 1.034 | 0.830 |
| MEA Conversion, % | 29.54 | 36.72 | 53.44 | 38.82 | 55.78 | 55.02 | 72.73 | 24.68 | 39.81 | 16.04 | 14.31 |
| DETA Conversion, % | 16.50 | 21.84 | 32.20 | 22.43 | 34.26 | 32.23 | 42.86 | 15.08 | 22.93 | 9.10 | 8.43 |
| Acyclic(N4), % | 97.38 | 97.07 | 95.31 | 97.77 | 95.01 | 94.37 | 89.26 | 97.73 | 95.84 | 98.71 | 97.58 |
| Acyclic(N5), % | 96.65 | 90.95 | 88.16 | 94.71 | 87.09 | 82.38 | 86.19 | 97.08 | 94.57 | 100.00 | 46.54 |
| Σ(N5)/Σ(N4), weight ratio | 0.27 | 0.38 | 0.60 | 0.38 | 0.66 | 0.69 | 0.81 | 0.28 | 0.44 | 0.15 | 0.14 |
| Acyclic(N4)/cyclic (<=N4), weight ratio | 10.30 | 9.49 | 6.49 | 9.91 | 5.87 | 4.68 | 2.80 | 9.90 | 7.47 | 12.67 | 10.70 |

TABLE XIII

| Example No. | 160 | 161 | 162 | 163 | 164 | 165 | 166 | 167 | 168 | 169 |
|---|---|---|---|---|---|---|---|---|---|---|
| Catalyst Type | M | M | M | M | M | M | M | M | M | M |
| Catalyst weight, gm | 50 | 50 | 50 | 50 | 50 | 50 | 50 | 50 | 50 | 50 |
| Pressure, psig | 600 | 600 | 600 | 400 | 600 | 600 | 600 | 600 | 600 | 600 |
| Temperature, °C. | 249.3 | 259.6 | 270.3 | 264.7 | 274.8 | 280.3 | 285.1 | 270.3 | 250.7 | 250.8 |
| Time on organics, hrs. | 4 | 24 | 28 | 48 | 52 | 72 | 76 | 100 | 119.7 | 144.5 |
| Duration of run, hrs. | 2 | 2 | 2 | 2 | 2 | 2 | 2 | 2 | 2 | 2 |
| MEA SV, gmol/hr/kgcat | 6.17 | 5.95 | 5.82 | 5.54 | 5.88 | 4.57 | 6.15 | 6.07 | 7.05 | 5.82 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.893 | 1.185 | 1.874 | 1.443 | 2.387 | 2.639 | 3.678 | 1.556 | 0.481 | 0.515 |
| MEA | 23.997 | 21.165 | 15.053 | 20.703 | 14.059 | 13.349 | 8.387 | 18.730 | 28.844 | 29.482 |
| PIP | 0.250 | 0.368 | 0.597 | 0.409 | 0.727 | 0.812 | 1.108 | 0.435 | 0.112 | 0.093 |
| DETA | 50.182 | 46.524 | 39.414 | 45.397 | 38.993 | 39.116 | 35.238 | 42.781 | 53.913 | 53.627 |
| AEEA | 2.411 | 2.498 | 2.085 | 2.340 | 1.699 | 1.499 | 0.681 | 2.101 | 1.876 | 1.810 |
| AEP | 0.422 | 0.510 | 0.810 | 0.527 | 0.904 | 1.012 | 1.488 | 0.535 | 0.274 | 0.244 |
| HEP | 0.000 | 0.000 | 0.000 | 0.000 | 0.000 | 0.000 | 0.000 | 0.000 | 0.000 | 0.000 |
| TAEA | 1.425 | 1.775 | 1.846 | 1.795 | 1.800 | 1.721 | 1.514 | 1.777 | 1.179 | 1.018 |
| 1-TETA | 10.191 | 11.986 | 13.100 | 11.628 | 12.524 | 12.091 | 11.574 | 10.990 | 6.600 | 5.769 |
| DAEP | 0.109 | 0.185 | 0.375 | 0.187 | 0.419 | 0.473 | 0.929 | 0.206 | 0.053 | 0.044 |
| PEEDA | 0.063 | 0.051 | 0.228 | 0.118 | 0.266 | 0.306 | 0.601 | 0.128 | 0.026 | 0.066 |
| DPE | 0.125 | 0.171 | 0.107 | 0.060 | 0.110 | 0.107 | 0.462 | 0.286 | 0.080 | 0.066 |
| AE-TAEA | 1.294 | 2.017 | 3.232 | 2.258 | 3.432 | 3.203 | 3.391 | 2.731 | 0.694 | 0.490 |
| 1-TEPA | 2.267 | 3.609 | 6.173 | 3.897 | 6.441 | 6.147 | 7.234 | 4.636 | 1.042 | 0.691 |
| AE-DAEP | 0.031 | 0.048 | 0.524 | 0.080 | 0.621 | 0.625 | 0.927 | 0.399 | 0.000 | 0.000 |
| AE-PEEDA | 0.000 | 0.033 | 0.108 | 0.047 | 0.094 | 0.111 | 0.467 | 0.157 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.236 | 0.000 | 0.224 | 0.275 | 0.049 | 0.299 | 0.000 | 0.000 |
| BPEA | 0.045 | 0.106 | 0.552 | 0.282 | 0.617 | 0.594 | 0.195 | 0.235 | 0.000 | 0.000 |
| Others | 1.906 | 3.042 | 6.857 | 3.249 | 7.904 | 8.181 | 13.108 | 5.468 | 1.100 | 0.978 |
| MEA Conversion, % | 34.77 | 42.76 | 59.22 | 43.57 | 62.03 | 63.61 | 77.16 | 48.81 | 21.06 | 17.89 |
| DETA Conversion, % | 19.07 | 25.41 | 36.70 | 26.65 | 37.57 | 36.79 | 43.13 | 30.69 | 12.53 | 11.46 |
| Acyclic(N4), % | 97.49 | 97.11 | 95.45 | 97.33 | 94.73 | 93.96 | 86.78 | 95.35 | 97.98 | 97.44 |
| Acyclic(N5), % | 97.89 | 96.76 | 86.87 | 93.75 | 86.37 | 85.33 | 86.62 | 87.08 | 100.00 | 100.00 |
| $\Sigma(N5)/\Sigma(N4)$, weight ratio | 0.30 | 0.41 | 0.69 | 0.47 | 0.75 | 0.74 | 0.81 | 0.63 | 0.21 | 0.16 |
| Acyclic(N4)/cyclic (<=N4), weight ratio | 11.96 | 10.68 | 7.04 | 10.28 | 5.89 | 5.09 | 2.85 | 8.01 | 14.23 | 13.14 |

TABLE XIV

| Comparative Example No. | 170 | 171 | 172 | 173 | 174 | 175 | 176 | 177 | 178 |
|---|---|---|---|---|---|---|---|---|---|
| Catalyst Type | N | N | N | N | N | N | N | N | N |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 251 | 250.5 | 260.7 | 265.6 | 270.4 | 275.8 | 280.5 | 255.8 | 245.6 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.47 | 3.80 | 3.91 | 3.78 | 4.01 | 3.87 | 4.12 | 3.34 | 3.15 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 2.846 | 1.526 | 2.032 | 1.886 | 2.080 | 2.055 | 2.349 | 0.725 | 0.430 |
| MEA | 20.117 | 22.677 | 18.757 | 16.307 | 13.974 | 13.175 | 11.612 | 25.948 | 29.403 |
| PIP | 0.388 | 0.256 | 0.499 | 0.640 | 0.773 | 0.847 | 0.969 | 0.218 | 0.102 |
| DETA | 38.752 | 46.030 | 41.118 | 41.094 | 35.948 | 37.509 | 34.665 | 52.792 | 56.722 |
| AEEA | 2.423 | 3.036 | 3.076 | 3.058 | 2.464 | 2.253 | 1.745 | 3.079 | 2.412 |
| AEP | 0.532 | 0.351 | 0.611 | 0.804 | 0.961 | 1.106 | 1.326 | 0.327 | 0.250 |
| HEP | 0.000 | 0.000 | 0.000 | 0.000 | 0.000 | 0.000 | 0.000 | 0.000 | 0.000 |
| TAEA | 0.913 | 0.960 | 1.193 | 1.429 | 1.379 | 1.405 | 1.366 | 0.793 | 0.480 |
| 1-TETA | 6.883 | 7.323 | 9.136 | 10.360 | 9.961 | 9.612 | 9.046 | 5.680 | 3.493 |
| DAEP | 0.130 | 0.038 | 0.254 | 0.343 | 0.479 | 0.517 | 0.769 | 0.100 | 0.049 |
| PEEDA | 0.188 | 0.076 | 0.217 | 0.124 | 0.154 | 0.084 | 0.662 | 0.074 | 0.036 |
| DPE | 0.150 | 0.132 | 0.325 | 0.319 | 0.397 | 0.361 | 0.120 | 0.153 | 0.089 |
| AE-TAEA | 0.216 | 0.137 | 1.821 | 0.185 | 0.244 | 0.207 | 2.472 | 0.625 | 0.349 |
| 1-TEPA | 0.297 | 2.808 | 4.728 | 6.414 | 7.260 | 6.994 | 7.086 | 2.162 | 0.887 |
| AE-DAEP | 0.731 | 0.413 | 0.156 | 0.157 | 0.197 | 0.176 | 1.016 | 0.226 | 0.078 |
| AE-PEEDA | 0.175 | 0.237 | 0.215 | 0.263 | 0.406 | 0.407 | 0.313 | 0.082 | 0.031 |
| iAE-PEEDA | 0.000 | 0.000 | 0.000 | 0.000 | 0.000 | 0.000 | 0.000 | 0.000 | 0.000 |
| AE-DPE | 0.291 | 0.147 | 0.259 | 0.254 | 0.453 | 0.383 | 0.175 | 0.036 | 0.138 |
| BPEA | 0.199 | 0.113 | 0.345 | 0.433 | 0.745 | 0.091 | 0.611 | 0.033 | 0.000 |
| Others | 16.400 | 7.123 | 10.349 | 11.322 | 15.766 | 15.360 | 16.327 | 3.878 | 2.051 |
| MEA Conversion, % | 43.51 | 37.03 | 49.65 | 56.66 | 62.55 | 64.22 | 68.78 | 30.04 | 19.95 |
| DETA Conversion, % | 35.49 | 24.23 | 34.57 | 35.26 | 42.89 | 39.62 | 44.75 | 15.62 | 8.46 |
| Acyclic(N4), % | 94.31 | 97.10 | 92.83 | 93.73 | 91.66 | 91.95 | 87.02 | 95.16 | 95.77 |
| Acyclic(N5), % | 26.85 | 76.39 | 87.03 | 85.62 | 80.62 | 87.19 | 81.87 | 88.03 | 83.29 |
| $\Sigma(N5)/\Sigma(N4)$, weight ratio | 0.23 | 0.45 | 0.67 | 0.61 | 0.75 | 0.68 | 0.97 | 0.46 | 0.35 |

TABLE XIV-continued

| Comparative Example No. | 170 | 171 | 172 | 173 | 174 | 175 | 176 | 177 | 178 |
|---|---|---|---|---|---|---|---|---|---|
| Acyclic(N4)/cyclic (<=N4), weight ratio | 5.60 | 9.69 | 5.41 | 5.27 | 4.09 | 3.77 | 2.70 | 7.39 | 7.51 |

TABLE XV

| Example No. | 179 | 180 | 181 | 182 | 183 | 184 | 185 | 186 | 187 | 188 |
|---|---|---|---|---|---|---|---|---|---|---|
| Catalyst Type | O | O | O | O | O | O | O | O | O | O |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 72 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.54 | 5.44 | 6.26 | 6.35 | 6.68 | 6.95 | 6.07 | 5.74 | 6.22 | 5.52 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.557 | 0.797 | 0.461 | 0.645 | 0.777 | 1.221 | 0.258 | 0.400 | 0.408 | 0.214 |
| MEA | 32.336 | 29.295 | 31.431 | 27.011 | 27.058 | 20.206 | 31.252 | 29.183 | 29.037 | 32.707 |
| PIP | 0.147 | 0.336 | 0.159 | 0.315 | 0.434 | 0.832 | 0.093 | 0.216 | 0.197 | 0.088 |
| DETA | 56.556 | 55.334 | 57.257 | 55.289 | 54.631 | 50.585 | 59.566 | 57.321 | 57.294 | 59.411 |
| AEEA | 2.101 | 2.829 | 2.340 | 2.851 | 2.944 | 2.743 | 2.003 | 2.673 | 2.620 | 1.871 |
| AEP | 0.307 | 0.366 | 0.271 | 0.435 | 0.440 | 0.778 | 0.285 | 0.332 | 0.318 | 0.272 |
| HEP | 0.000 | 0.000 | 0.000 | 0.000 | 0.000 | 0.000 | 0.000 | 0.000 | 0.000 | 0.000 |
| TAEA | 0.432 | 0.692 | 0.443 | 0.736 | 0.478 | 1.212 | 0.436 | 0.516 | 0.547 | 0.280 |
| l-TETA | 2.629 | 4.380 | 2.617 | 4.340 | 4.427 | 7.328 | 2.476 | 3.221 | 3.344 | 1.831 |
| DAEP | 0.162 | 0.122 | 0.053 | 0.087 | 0.088 | 0.243 | 0.039 | 0.054 | 0.055 | 0.074 |
| PEEDA | 0.052 | 0.024 | 0.046 | 0.028 | 0.021 | 0.247 | 0.029 | 0.027 | 0.030 | 0.025 |
| DPE | 0.000 | 0.064 | 0.078 | 0.068 | 0.075 | 0.145 | 0.031 | 0.045 | 0.039 | 0.000 |
| AE-TAEA | 0.082 | 0.270 | 0.095 | 0.335 | 0.461 | 1.255 | 0.092 | 0.152 | 0.245 | 0.060 |
| l-TEPA | 0.033 | 0.668 | 0.303 | 0.856 | 1.340 | 3.408 | 0.229 | 0.413 | 0.661 | 0.085 |
| AE-DAEP | 0.083 | 0.027 | 0.000 | 0.020 | 0.058 | 0.215 | 0.000 | 0.000 | 0.000 | 0.000 |
| AE-PEEDA | 0.055 | 0.000 | 0.000 | 0.000 | 0.000 | 0.025 | 0.075 | 0.161 | 0.184 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.106 | 0.000 | 0.000 | 0.000 | 0.000 | 0.087 | 0.000 | 0.000 | 0.000 | 0.118 |
| BPEA | 0.000 | 0.000 | 0.000 | 0.000 | 0.036 | 0.100 | 0.000 | 0.000 | 0.000 | 0.000 |
| Others | 1.554 | 1.558 | 1.509 | 1.685 | 2.059 | 3.632 | 1.368 | 1.728 | 1.572 | 0.679 |
| MEA Conversion, % | 11.54 | 20.03 | 14.00 | 24.93 | 25.58 | 44.77 | 15.58 | 20.02 | 20.56 | 10.86 |
| DETA Conversion, % | 8.29 | 10.46 | 7.13 | 8.91 | 10.93 | 18.03 | 4.61 | 6.87 | 7.07 | 4.01 |
| Acyclic(N4), % | 93.44 | 95.99 | 94.48 | 96.48 | 96.52 | 93.06 | 96.66 | 96.71 | 96.87 | 95.47 |
| Acyclic(N5), % | 32.06 | 97.13 | 100.00 | 98.26 | 94.89 | 91.56 | 80.95 | 77.80 | 83.06 | 55.28 |
| Σ(N5)/Σ(N4), weight ratio | 0.11 | 0.18 | 0.12 | 0.23 | 0.34 | 0.55 | 0.13 | 0.18 | 0.27 | 0.11 |
| Acyclic(N4)/cyclic (<=N4), weight ratio | 4.57 | 5.54 | 5.02 | 5.42 | 4.87 | 3.80 | 6.08 | 5.53 | 6.06 | 4.58 |

TABLE XVI

| Comparative Example No. | 189 | 190 | 191 | 192 | 193 | 194 | 195 | 196 | 197 |
|---|---|---|---|---|---|---|---|---|---|
| Catalyst Type | P | P | P | P | P | P | P | P | P |
| Catalyst weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.46 | 3.96 | 3.89 | 3.66 | 3.88 | 3.96 | 4.00 | 3.97 | 4.04 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.569 | 0.369 | 0.606 | 0.790 | 0.904 | 1.370 | 1.436 | 0.353 | 0.165 |
| MEA | 22.906 | 25.594 | 20.285 | 17.926 | 14.593 | 14.303 | 12.427 | 26.475 | 30.271 |
| PIP | 0.366 | 0.218 | 0.401 | 0.561 | 0.667 | 1.037 | 1.090 | 0.220 | 0.079 |
| DETA | 50.355 | 54.133 | 48.370 | 47.753 | 41.854 | 42.262 | 40.213 | 53.453 | 59.022 |
| AEEA | 2.955 | 3.393 | 3.649 | 3.648 | 2.988 | 2.426 | 1.989 | 2.794 | 2.193 |
| AEP | 0.473 | 0.305 | 0.456 | 0.607 | 0.722 | 1.086 | 1.211 | 0.306 | 0.236 |
| HEP | 0.000 | 0.000 | 0.000 | 0.000 | 0.000 | 0.000 | 0.000 | 0.000 | 0.000 |
| TAEA | 1.254 | 1.114 | 1.436 | 1.582 | 1.518 | 1.586 | 1.556 | 0.732 | 0.447 |
| l-TETA | 7.783 | 6.913 | 9.002 | 9.975 | 9.612 | 10.518 | 10.362 | 4.586 | 2.655 |
| DAEP | 0.122 | 0.065 | 0.137 | 0.196 | 0.312 | 0.449 | 0.543 | 0.081 | 0.040 |
| PEEDA | 0.065 | 0.039 | 0.117 | 0.171 | 0.130 | 0.064 | 0.515 | 0.067 | 0.029 |
| DPE | 0.063 | 0.049 | 0.181 | 0.170 | 0.302 | 0.281 | 0.115 | 0.161 | 0.062 |
| AE-TAEA | 0.161 | 0.112 | 1.712 | 1.846 | 2.488 | 0.152 | 2.426 | 0.607 | 0.179 |
| l-TEPA | 2.457 | 1.842 | 3.712 | 4.349 | 5.404 | 6.285 | 6.578 | 1.410 | 0.198 |
| AE-DAEP | 0.059 | 0.063 | 0.165 | 0.212 | 0.623 | 0.154 | 0.685 | 0.248 | 0.065 |
| AE-PEEDA | 0.059 | 0.025 | 0.138 | 0.103 | 0.359 | 0.325 | 0.207 | 0.152 | 0.036 |
| iAE-PEEDA | 0.000 | 0.000 | 0.000 | 0.000 | 0.000 | 0.000 | 0.000 | 0.000 | 0.000 |

TABLE XVI-continued

| Comparative Example No. | 189 | 190 | 191 | 192 | 193 | 194 | 195 | 196 | 197 |
|---|---|---|---|---|---|---|---|---|---|
| AE-DPE | 0.044 | 0.028 | 0.236 | 0.276 | 0.341 | 0.169 | 0.351 | 0.184 | 0.138 |
| BPEA | 0.025 | 0.049 | 0.166 | 0.271 | 0.792 | 0.439 | 0.423 | 0.121 | 0.000 |
| Others | 3.746 | 2.581 | 5.592 | 4.546 | 10.542 | 10.867 | 9.666 | 4.479 | 1.866 |
| MEA Conversion, % | 36.31 | 30.93 | 45.92 | 51.83 | 60.98 | 61.53 | 66.10 | 28.20 | 17.97 |
| DETA Conversion, % | 17.00 | 13.40 | 23.56 | 23.94 | 33.65 | 32.63 | 34.97 | 14.06 | 5.18 |
| Acyclic(N4), % | 97.29 | 98.10 | 95.97 | 95.54 | 93.72 | 93.83 | 91.02 | 94.48 | 95.88 |
| Acyclic(N5), % | 93.26 | 92.16 | 88.46 | 87.92 | 78.84 | 85.42 | 84.36 | 74.04 | 61.21 |
| Σ(N5)/Σ(N4), weight ratio | 0.30 | 0.25 | 0.56 | 0.59 | 0.84 | 0.58 | 0.81 | 0.48 | 0.19 |
| Acyclic(N4)/cyclic (<=N4), weight ratio | 8.28 | 11.82 | 8.06 | 6.76 | 5.21 | 4.14 | 3.42 | 6.35 | 6.89 |

TABLE XVII

| Comparative Example No. | 198 | 199 | 200 | 201 | 202 | 203 | 204 | 205 | 206 |
|---|---|---|---|---|---|---|---|---|---|
| Catalyst Type | Q | Q | Q | Q | Q | Q | Q | Q | Q |
| Catalyst weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 4.35 | 4.44 | 4.56 | 3.97 | 4.31 | 4.29 | 4.42 | 3.99 | 4.38 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.129 | 0.034 | 0.081 | 0.130 | 0.184 | 0.319 | 0.432 | 0.086 | 0.044 |
| MEA | 31.011 | 33.961 | 32.995 | 30.431 | 29.013 | 27.475 | 26.166 | 30.793 | 34.503 |
| PIP | 0.136 | 0.085 | 0.172 | 0.302 | 0.423 | 0.645 | 0.863 | 0.155 | 0.069 |
| DETA | 59.305 | 59.998 | 58.455 | 58.206 | 56.825 | 54.579 | 51.202 | 55.790 | 59.775 |
| AEEA | 1.084 | 1.095 | 1.515 | 1.846 | 1.989 | 2.043 | 1.872 | 1.338 | 0.780 |
| AEP | 0.308 | 0.219 | 0.266 | 0.335 | 0.419 | 0.580 | 0.708 | 0.282 | 0.209 |
| HEP | 0.000 | 0.000 | 0.000 | 0.000 | 0.000 | 0.000 | 0.000 | 0.000 | 0.000 |
| TAEA | 0.432 | 0.292 | 0.389 | 0.566 | 0.673 | 0.798 | 0.785 | 0.390 | 0.223 |
| l-TETA | 2.508 | 1.580 | 1.972 | 2.905 | 3.532 | 4.375 | 4.754 | 2.170 | 1.109 |
| DAEP | 0.065 | 0.025 | 0.043 | 0.060 | 0.080 | 0.127 | 0.290 | 0.149 | 0.046 |
| PEEDA | 0.047 | 0.029 | 0.037 | 0.051 | 0.085 | 0.146 | 0.239 | 0.084 | 0.027 |
| DPE | 0.022 | 0.038 | 0.057 | 0.072 | 0.080 | 0.101 | 0.100 | 0.221 | 0.018 |
| AE-TAEA | 0.305 | 0.284 | 0.525 | 0.127 | 0.137 | 1.094 | 0.823 | 0.664 | 0.107 |
| l-TEPA | 0.579 | 0.428 | 0.478 | 1.062 | 1.431 | 1.985 | 2.525 | 1.037 | 0.075 |
| AE-DAEP | 0.063 | 0.194 | 0.053 | 0.066 | 0.116 | 0.232 | 0.666 | 0.600 | 0.000 |
| AE-PEEDA | 0.000 | 0.000 | 0.050 | 0.039 | 0.034 | 0.106 | 0.169 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.053 | 0.078 | 0.027 | 0.063 | 0.028 | 0.045 | 0.037 | 0.417 | 0.201 |
| BPEA | 0.035 | 0.000 | 0.000 | 0.000 | 0.021 | 0.040 | 0.045 | 0.037 | 0.000 |
| Others | 1.348 | 0.783 | 1.767 | 2.309 | 2.800 | 3.375 | 4.038 | 3.468 | 0.757 |
| MEA Conversion, % | 15.65 | 8.73 | 11.34 | 18.47 | 22.00 | 26.74 | 28.82 | 16.92 | 5.92 |
| DETA Conversion, % | 4.38 | 4.41 | 6.89 | 7.56 | 9.44 | 13.72 | 17.43 | 10.77 | 3.38 |
| Acyclic(N4), % | 95.58 | 95.25 | 94.45 | 94.94 | 94.46 | 93.24 | 89.79 | 84.87 | 93.55 |
| Acyclic(N5), % | 85.28 | 72.27 | 88.43 | 86.18 | 87.68 | 87.70 | 78.48 | 61.69 | 47.75 |
| Σ(N5)/Σ(N4), weight ratio | 0.33 | 0.50 | 0.45 | 0.37 | 0.40 | 0.63 | 0.69 | 0.91 | 0.26 |
| Acyclic(N4)/cyclic (<=N4), weight ratio | 5.06 | 4.70 | 4.08 | 4.22 | 3.85 | 3.23 | 2.51 | 2.86 | 3.60 |

TABLE XVIII

| Example No. | 207 | 208 | 209 | 210 | 211 | 212 | 213 | 214 | 215 | 216 | 217 |
|---|---|---|---|---|---|---|---|---|---|---|---|
| Catalyst Type | R | R | R | R | R | R | R | R | R | R | R |
| Catalyst weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.4 | 250.2 | 260.0 | 264.8 | 274.3 | 269.7 | 279.7 | 254.6 | 265.5 | 250.0 | 250.0 |
| Time on organics, hrs. | 3.5 | 22.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 | 2 |
| MEA SV, gmol/hr/kgcat | 4.87 | 5.72 | 6.05 | 6.00 | 6.02 | 5.98 | 5.04 | 5.89 | 5.99 | 5.66 | 5.83 |
| DETA/MEA mole ratio | 0.99 | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 1.519 | 0.694 | 1.216 | 1.280 | 2.428 | 1.153 | 2.115 | 0.252 | 0.488 | 0.120 | -0.078 |
| MEA | 31.506 | 32.042 | 30.354 | 30.605 | 27.717 | 30.601 | 23.296 | 33.872 | 32.164 | 35.051 | 35.546 |
| PIP | 0.817 | 0.572 | 1.053 | 1.075 | 1.986 | 0.958 | 1.628 | 0.224 | 0.444 | 0.105 | 0.071 |
| DETA | 49.429 | 53.921 | 50.152 | 49.725 | 43.594 | 50.450 | 38.887 | 57.536 | 55.374 | 59.521 | 60.251 |
| AEEA | 0.896 | 0.966 | 1.015 | 0.991 | 0.957 | 1.013 | 0.855 | 0.774 | 1.009 | 0.339 | 0.338 |
| AEP | 0.642 | 0.422 | 0.770 | 0.803 | 1.591 | 0.760 | 1.481 | 0.293 | 0.430 | 0.243 | 0.206 |
| HEP | 0.000 | 0.000 | 0.000 | 0.000 | 0.000 | 0.000 | 0.000 | 0.000 | 0.000 | 0.000 | 0.000 |
| TAEA | 0.734 | 0.732 | 0.884 | 0.820 | 0.779 | 0.837 | 0.758 | 0.520 | 0.767 | 0.322 | 0.235 |

TABLE XVIII-continued

| Example No. | 207 | 208 | 209 | 210 | 211 | 212 | 213 | 214 | 215 | 216 | 217 |
|---|---|---|---|---|---|---|---|---|---|---|---|
| 1-TETA | 4.465 | 4.271 | 5.695 | 5.262 | 5.911 | 5.274 | 5.499 | 2.760 | 4.241 | 1.727 | 1.284 |
| DAEP | 0.173 | 0.090 | 0.194 | 0.193 | 0.476 | 0.176 | 0.452 | 0.039 | 0.095 | 0.000 | 0.000 |
| PEEDA | 0.153 | 0.064 | 0.187 | 0.199 | 0.589 | 0.178 | 0.544 | 0.025 | 0.099 | 0.000 | 0.000 |
| DPE | 0.059 | 0.026 | 0.052 | 0.062 | 0.131 | 0.056 | 0.168 | 0.000 | 0.044 | 0.000 | 0.000 |
| AE-TAEA | 0.538 | 0.468 | 0.781 | 0.769 | 0.931 | 0.682 | 0.987 | 0.185 | 0.411 | 0.000 | 0.000 |
| 1-TEPA | 1.798 | 1.534 | 2.851 | 2.784 | 3.990 | 2.531 | 3.812 | 0.440 | 1.232 | 0.000 | 0.000 |
| AE-DAEP | 0.111 | 0.079 | 0.177 | 0.165 | 0.389 | 0.088 | 0.463 | 0.000 | 0.000 | 0.000 | 0.000 |
| AE-PEEDA | 0.165 | 0.051 | 0.105 | 0.092 | 0.193 | 0.074 | 0.275 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.105 | 0.000 | 0.000 | 0.000 | 0.000 |
| BPEA | 0.000 | 0.000 | 0.090 | 0.098 | 0.188 | 0.085 | 0.308 | 0.000 | 0.000 | 0.000 | 0.000 |
| Others | 2.487 | 1.092 | 2.264 | 2.409 | 4.492 | 2.276 | 5.439 | 0.924 | 1.213 | 0.418 | 0.337 |
| MEA Conversion, % | 12.79 | 12.53 | 18.53 | 17.36 | 25.28 | 17.17 | 30.93 | 7.75 | 13.08 | 4.17 | 3.21 |
| DETA Conversion, % | 18.89 | 12.74 | 20.21 | 20.40 | 30.33 | 19.05 | 31.65 | 7.11 | 11.29 | 3.53 | 2.74 |
| Acyclic(N4), % | 93.08 | 96.49 | 93.79 | 93.03 | 84.81 | 93.68 | 84.30 | 98.06 | 95.42 | 100.00 | 100.00 |
| Acyclic(N5), % | 89.40 | 93.87 | 90.65 | 90.87 | 86.46 | 92.82 | 80.64 | 100.00 | 100.00 | 0.00 | 0.00 |
| Σ(N5)/Σ(N4), weight ratio | 0.46 | 0.41 | 0.57 | 0.59 | 0.72 | 0.53 | 0.80 | 0.18 | 0.31 | 0.00 | 0.00 |
| Acyclic(N4)/cyclic (<=N4), weight ratio | 2.81 | 4.25 | 2.91 | 2.60 | 1.40 | 2.86 | 1.46 | 5.63 | 4.49 | 5.88 | 5.47 |

TABLE XIX

| Example No. | 218 | 219 | 220 | 221 | 222 | 223 | 224 | 225 | 226 | 227 |
|---|---|---|---|---|---|---|---|---|---|---|
| Catalyst Type | S | S | S | S | S | S | S | S | S | S |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.4 | 260.0 | 264.8 | 274.3 | 269.7 | 279.6 | 250.0 | 265.5 | 250.0 | 250.0 |
| Time on organics, hrs. | 3.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 |
| MEA SV, gmol/hr/kgcat | 5.19 | 6.09 | 7.07 | 6.15 | 6.06 | 5.36 | 5.94 | 6.02 | 5.71 | 6.05 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 2.846 | 2.162 | 2.521 | 3.371 | 2.410 | 3.708 | 0.958 | 1.667 | 0.727 | 0.656 |
| MEA | 28.451 | 28.405 | 27.689 | 22.373 | 26.870 | 19.491 | 30.997 | 27.854 | 33.177 | 33.332 |
| PIP | 0.292 | 0.311 | 0.356 | 0.675 | 0.375 | 0.711 | 0.117 | 0.226 | 0.073 | 0.061 |
| DETA | 47.215 | 49.052 | 48.027 | 42.085 | 47.503 | 38.192 | 54.844 | 50.639 | 55.737 | 56.938 |
| AEEA | 1.527 | 1.477 | 1.552 | 1.306 | 1.542 | 1.289 | 1.199 | 1.503 | 0.934 | 0.936 |
| AEP | 0.394 | 0.489 | 0.563 | 0.836 | 0.604 | 0.971 | 0.390 | 0.530 | 0.340 | 0.348 |
| HEP | 0.000 | 0.000 | 0.000 | 0.000 | 0.000 | 0.000 | 0.000 | 0.000 | 0.000 | 0.000 |
| TAEA | 0.805 | 0.950 | 0.969 | 1.115 | 1.032 | 1.206 | 0.726 | 1.030 | 0.478 | 0.461 |
| 1-TETA | 6.223 | 6.861 | 7.071 | 8.458 | 7.313 | 8.977 | 4.883 | 6.759 | 3.252 | 3.068 |
| DAEP | 0.139 | 0.130 | 0.150 | 0.290 | 0.155 | 0.368 | 0.054 | 0.112 | 0.000 | 0.000 |
| PEEDA | 0.054 | 0.065 | 0.083 | 0.181 | 0.089 | 0.248 | 0.048 | 0.059 | 0.046 | 0.037 |
| DPE | 0.186 | 0.172 | 0.213 | 0.359 | 0.226 | 0.502 | 0.080 | 0.180 | 0.036 | 0.025 |
| AE-TAEA | 0.595 | 0.826 | 0.906 | 1.543 | 0.942 | 1.789 | 0.306 | 0.113 | 0.129 | 0.072 |
| 1-TEPA | 1.190 | 1.632 | 1.751 | 3.174 | 1.795 | 3.752 | 0.447 | 1.274 | 0.082 | 0.419 |
| AE-DAEP | 0.075 | 0.104 | 0.098 | 0.253 | 0.091 | 0.309 | 0.000 | 0.036 | 0.000 | 0.000 |
| AE-PEEDA | 0.356 | 0.187 | 0.182 | 0.431 | 0.151 | 0.490 | 0.000 | 0.085 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.079 | 0.083 | 0.070 | 0.063 | 0.065 | 0.158 | 0.101 | 0.121 | 0.309 | 0.000 |
| BPEA | 0.000 | 0.062 | 0.081 | 0.053 | 0.103 | 0.135 | 0.034 | 0.144 | 0.000 | 0.000 |
| Others | 4.635 | 4.013 | 4.427 | 8.254 | 4.444 | 10.424 | 2.167 | 4.231 | 1.493 | 1.571 |
| MEA Conversion, % | 21.20 | 23.10 | 24.95 | 39.09 | 26.53 | 46.19 | 15.71 | 24.30 | 8.77 | 9.35 |
| DETA Conversion, % | 22.48 | 21.28 | 22.83 | 32.08 | 23.00 | 37.50 | 11.59 | 18.42 | 9.14 | 8.20 |
| Acyclic(N4), % | 94.87 | 95.49 | 94.72 | 92.01 | 94.64 | 90.09 | 96.84 | 95.68 | 97.81 | 98.24 |
| Acyclic(N5), % | 77.74 | 84.86 | 85.97 | 85.46 | 86.94 | 83.49 | 84.65 | 78.19 | 40.69 | 100.00 |
| Σ(N5)/Σ(N4), weight ratio | 0.31 | 0.35 | 0.36 | 0.53 | 0.35 | 0.58 | 0.15 | 0.21 | 0.13 | 0.13 |
| Acyclic(N4)/cyclic (<=N4), weight ratio | 6.58 | 6.67 | 5.87 | 4.08 | 5.74 | 3.63 | 8.11 | 7.02 | 7.50 | 7.46 |

TABLE XX

| Example No. | 228 | 229 | 230 | 231 | 232 | 233 | 234 | 235 | 236 | 237 | 238 |
|---|---|---|---|---|---|---|---|---|---|---|---|
| Catalyst Type | T | T | T | T | T | T | T | T | T | T | T |
| Catalyst weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.4 | 250.2 | 260.0 | 264.8 | 274.3 | 269.7 | 279.6 | 254.9 | 265.5 | 250.0 | 250.0 |
| Time on organics, hrs. | 3.5 | 22.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 | 2 |
| MEA SV, gmol/hr/kgcat | 4.96 | 5.31 | 5.56 | 5.64 | 5.56 | 5.51 | 5.09 | 5.43 | 5.54 | 5.23 | 5.37 |
| DETA/MEA mole ratio | 0.99 | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 0.654 | 0.449 | 0.757 | 0.960 | 1.686 | 1.190 | 2.015 | 0.476 | 0.898 | 0.343 | 0.351 |

TABLE XX-continued

| Example No | 228 | 229 | 230 | 231 | 232 | 233 | 234 | 235 | 236 | 237 | 238 |
|---|---|---|---|---|---|---|---|---|---|---|---|
| MEA | 27.386 | 29.344 | 25.472 | 23.704 | 17.028 | 22.148 | 12.850 | 28.641 | 23.935 | 30.296 | 30.702 |
| PIP | 0.229 | 0.158 | 0.318 | 0.417 | 0.765 | 0.526 | 0.925 | 0.165 | 0.377 | 0.111 | 0.109 |
| DETA | 53.639 | 55.586 | 52.752 | 50.945 | 45.979 | 49.847 | 40.504 | 56.024 | 51.376 | 57.092 | 57.637 |
| AEEA | 2.419 | 2.339 | 2.764 | 2.728 | 2.360 | 2.672 | 1.772 | 2.377 | 2.731 | 2.066 | 2.049 |
| AEP | 0.319 | 0.268 | 0.391 | 0.468 | 0.851 | 0.568 | 1.059 | 0.297 | 0.452 | 0.262 | 0.268 |
| HEP | 0.000 | 0.000 | 0.000 | 0.000 | 0.000 | 0.000 | 0.000 | 0.000 | 0.000 | 0.000 | 0.000 |
| TAEA | 1.067 | 0.826 | 1.226 | 1.323 | 1.677 | 1.416 | 1.728 | 0.900 | 1.406 | 0.710 | 0.675 |
| 1-TETA | 6.467 | 4.920 | 7.114 | 7.589 | 9.995 | 8.115 | 10.503 | 4.990 | 7.814 | 3.954 | 3.695 |
| DAEP | 0.088 | 0.062 | 0.117 | 0.137 | 0.317 | 0.176 | 0.437 | 0.057 | 0.137 | 0.044 | 0.052 |
| PEEDA | 0.054 | 0.044 | 0.081 | 0.083 | 0.227 | 0.154 | 0.396 | 0.040 | 0.081 | 0.029 | 0.052 |
| DPE | 0.045 | 0.029 | 0.068 | 0.096 | 0.188 | 0.128 | 0.297 | 0.045 | 0.106 | 0.037 | 0.032 |
| AE-TAEA | 0.685 | 0.395 | 1.040 | 1.239 | 2.283 | 1.495 | 2.774 | 0.419 | 1.182 | 0.238 | 0.195 |
| 1-TEPA | 1.252 | 0.683 | 2.067 | 2.357 | 4.522 | 2.895 | 5.506 | 0.703 | 2.253 | 0.393 | 0.295 |
| AE-DAEP | 0.000 | 0.000 | 0.099 | 0.104 | 0.276 | 0.134 | 0.596 | 0.000 | 0.079 | 0.000 | 0.000 |
| AE-PEEDA | 0.031 | 0.000 | 0.000 | 0.034 | 0.087 | 0.038 | 0.220 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.089 | 0.000 | 0.165 | 0.000 | 0.000 | 0.525 | 0.202 |
| BPEA | 0.098 | 0.000 | 0.136 | 0.132 | 0.363 | 0.186 | 0.107 | 0.000 | 0.130 | 0.000 | 0.000 |
| Others | 1.308 | 1.020 | 1.910 | 2.415 | 4.738 | 3.325 | 7.889 | 1.257 | 2.793 | 1.201 | 1.290 |
| MEA Conversion, % | 24.85 | 19.33 | 30.93 | 34.91 | 53.54 | 39.67 | 63.95 | 21.61 | 34.98 | 17.69 | 16.70 |
| DETA Conversion, % | 12.74 | 9.41 | 15.20 | 17.07 | 25.63 | 19.50 | 32.65 | 9.10 | 17.26 | 8.05 | 7.29 |
| Acyclic(N4), % | 97.56 | 97.67 | 96.88 | 96.55 | 94.09 | 95.39 | 91.54 | 97.62 | 96.58 | 97.64 | 96.94 |
| Acyclic(N5), % | 93.71 | 100.00 | 92.95 | 92.97 | 89.29 | 92.45 | 88.36 | 100.00 | 94.22 | 54.59 | 70.75 |
| $\Sigma(N5)/\Sigma(N4)$, weight ratio | 0.26 | 0.18 | 0.38 | 0.41 | 0.61 | 0.47 | 0.70 | 0.18 | 0.38 | 0.24 | 0.15 |
| Acyclic(N4)/cyclic ($<=$N4), weight ratio | 10.21 | 10.19 | 8.53 | 7.40 | 4.96 | 6.13 | 3.92 | 9.70 | 7.96 | 9.58 | 8.47 |

TABLE XXI

| Example No. | 239 | 240 | 241 | 242 | 243 | 244 | 245 | 246 | 247 | 248 |
|---|---|---|---|---|---|---|---|---|---|---|
| Catalyst Type | U | U | U | U | U | U | U | U | U | U |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 250.7 | 260.9 | 265.9 | 275.6 | 270.7 | 280.7 | 255.9 | 266.0 | 250.0 | 250.0 |
| Time on organics, hrs. | 24 | 28 | 48 | 52 | 72 | 76 | 96 | 100 | 119 | 143 |
| Duration of run, hrs. | 2 | 2 | 2 | 2 | 2 | 2 | 2 | 2 | 2 | 2 |
| MEA SV, gmol/hr/kgcat | 5.63 | 5.74 | 3.32 | 5.65 | 5.42 | 5.49 | 5.53 | 5.57 | 5.89 | 5.93 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.903 | 1.402 | 1.768 | 2.544 | 1.835 | 3.073 | 0.888 | 1.294 | 0.515 | 0.506 |
| MEA | 25.752 | 20.894 | 16.605 | 12.576 | 17.830 | 10.281 | 26.167 | 20.923 | 27.453 | 29.003 |
| PIP | 0.219 | 0.362 | 0.507 | 0.711 | 0.498 | 0.901 | 0.187 | 0.353 | 0.106 | 0.103 |
| DETA | 50.036 | 46.155 | 42.553 | 38.126 | 43.798 | 37.053 | 51.456 | 47.042 | 54.880 | 54.395 |
| AEEA | 1.893 | 2.170 | 2.124 | 1.446 | 1.873 | 1.003 | 2.038 | 2.036 | 1.893 | 1.661 |
| AEP | 0.352 | 0.501 | 0.668 | 0.969 | 0.662 | 1.189 | 0.334 | 0.490 | 0.278 | 0.267 |
| HEP | 0.000 | 0.000 | 0.000 | 0.000 | 0.000 | 0.000 | 0.000 | 0.000 | 0.000 | 0.000 |
| TAEA | 1.345 | 1.686 | 1.782 | 1.715 | 1.776 | 1.699 | 1.361 | 1.719 | 1.214 | 1.039 |
| 1-TETA | 9.150 | 11.543 | 12.441 | 12.696 | 11.873 | 12.762 | 8.128 | 10.831 | 7.041 | 5.981 |
| DAEP | 0.123 | 0.212 | 0.297 | 0.536 | 0.298 | 0.703 | 0.088 | 0.187 | 0.057 | 0.051 |
| PEEDA | 0.063 | 0.115 | 0.173 | 0.315 | 0.175 | 0.078 | 0.051 | 0.100 | 0.035 | 0.035 |
| DPE | 0.076 | 0.135 | 0.211 | 0.313 | 0.079 | 0.133 | 0.082 | 0.072 | 0.048 | 0.060 |
| AE-TAEA | 1.447 | 2.123 | 2.635 | 3.323 | 2.723 | 3.556 | 1.164 | 2.237 | 0.691 | 0.565 |
| 1-TEPA | 2.439 | 3.738 | 4.737 | 6.407 | 4.814 | 6.968 | 1.786 | 3.880 | 0.956 | 0.711 |
| AE-DAEP | 0.033 | 0.115 | 0.343 | 0.446 | 0.192 | 0.758 | 0.000 | 0.081 | 0.000 | 0.000 |
| AE-PEEDA | 0.000 | 0.048 | 0.132 | 0.326 | 0.068 | 0.357 | 0.000 | 0.046 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.062 | 0.077 | 0.106 | 0.119 | 0.091 | 0.112 | 0.000 | 0.000 | 0.000 | 0.000 |
| BPEA | 0.198 | 0.376 | 0.163 | 0.712 | 0.593 | 0.257 | 0.112 | 0.102 | 0.000 | 0.000 |
| Others | 1.859 | 3.207 | 5.566 | 8.060 | 4.576 | 10.826 | 1.993 | 3.228 | 1.156 | 1.187 |
| MEA Conversion, % | 30.00 | 43.32 | 54.48 | 65.46 | 51.49 | 72.02 | 28.58 | 43.01 | 25.09 | 19.91 |
| DETA Conversion, % | 19.37 | 25.78 | 30.84 | 37.92 | 29.36 | 40.22 | 16.74 | 24.04 | 11.23 | 10.95 |
| Acyclic(N4), % | 97.54 | 96.61 | 95.41 | 92.51 | 96.10 | 94.03 | 97.71 | 97.19 | 98.32 | 97.94 |
| Acyclic(N5), % | 92.96 | 90.47 | 90.82 | 85.91 | 88.84 | 87.63 | 96.33 | 96.38 | 100.00 | 100.00 |
| $\Sigma(N5)/\Sigma(N4)$, weight ratio | 0.38 | 0.47 | 0.54 | 0.72 | 0.59 | 0.78 | 0.31 | 0.49 | 0.19 | 0.17 |
| Acyclic(N4)/cyclic ($<=$N4), weight ratio | 12.56 | 9.96 | 7.65 | 5.06 | 7.95 | 4.80 | 12.76 | 10.41 | 15.69 | 13.56 |

TABLE XXII

| Example No. | 249 | 250 | 251 | 252 | 253 | 254 | 255 | 256 | 257 | 258 |
|---|---|---|---|---|---|---|---|---|---|---|
| Catalyst Type | V | V | V | V | V | V | V | V | V | V |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 250.9 | 260.9 | 265.9 | 275.6 | 270.7 | 280.7 | 255.9 | 266.0 | 250.0 | 250.0 |
| Time on organics, hrs. | 24 | 28 | 48 | 52 | 72 | 76 | 96 | 100 | 119 | 143 |

TABLE XXII-continued

| Example No. | 249 | 250 | 251 | 252 | 253 | 254 | 255 | 256 | 257 | 258 |
|---|---|---|---|---|---|---|---|---|---|---|
| Duration of run, hrs. | 2 | 2 | 2 | 2 | 2 | 2 | 2 | 2 | 2 | 2 |
| MEA SV, gmol/hr/kgcat | 5.32 | 5.25 | 5.18 | 5.19 | 5.09 | 5.20 | 5.18 | 5.12 | 5.39 | 5.47 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.592 | 1.050 | 1.170 | 2.045 | 1.486 | 2.547 | 0.696 | 1.188 | 0.456 | 0.452 |
| MEA | 27.184 | 23.113 | 22.344 | 15.162 | 21.294 | 13.368 | 28.286 | 24.782 | 31.286 | 31.867 |
| PIP | 0.127 | 0.270 | 0.291 | 0.551 | 0.372 | 0.660 | 0.135 | 0.269 | 0.080 | 0.076 |
| DETA | 53.615 | 49.172 | 48.478 | 41.150 | 47.716 | 39.980 | 54.059 | 50.590 | 55.663 | 57.022 |
| AEEA | 2.106 | 2.326 | 2.191 | 1.866 | 2.144 | 1.559 | 1.968 | 2.123 | 1.530 | 1.495 |
| AEP | 0.280 | 0.388 | 0.415 | 0.715 | 0.489 | 0.840 | 0.283 | 0.381 | 0.235 | 0.239 |
| HEP | 0.000 | 0.000 | 0.000 | 0.000 | 0.000 | 0.000 | 0.000 | 0.000 | 0.000 | 0.000 |
| TAEA | 1.264 | 1.608 | 1.571 | 1.888 | 1.686 | 1.837 | 1.171 | 1.430 | 0.801 | 0.757 |
| 1-TETA | 7.794 | 10.144 | 9.823 | 12.185 | 10.176 | 11.968 | 6.606 | 8.234 | 4.501 | 4.245 |
| DAEP | 0.076 | 0.137 | 0.147 | 0.347 | 0.166 | 0.413 | 0.062 | 0.105 | 0.035 | 0.000 |
| PEEDA | 0.034 | 0.074 | 0.089 | 0.211 | 0.099 | 0.086 | 0.039 | 0.063 | 0.029 | 0.000 |
| DPE | 0.045 | 0.094 | 0.134 | 0.118 | 0.156 | 0.130 | 0.066 | 0.108 | 0.000 | 0.000 |
| AE-TAEA | 0.814 | 0.589 | 1.649 | 2.952 | 1.965 | 3.233 | 0.758 | 1.349 | 0.372 | 0.000 |
| 1-TEPA | 1.274 | 2.726 | 2.848 | 5.423 | 3.349 | 5.930 | 1.123 | 2.132 | 0.504 | 0.000 |
| AE-DAEP | 0.000 | 0.000 | 0.086 | 0.479 | 0.108 | 0.545 | 0.000 | 0.031 | 0.000 | 0.000 |
| AE-PEEDA | 0.000 | 0.000 | 0.029 | 0.188 | 0.035 | 0.201 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.073 | 0.100 | 0.119 | 0.079 | 0.126 | 0.000 | 0.070 | 0.000 | 0.000 |
| BPEA | 0.000 | 0.199 | 0.189 | 0.565 | 0.277 | 0.243 | 0.000 | 0.169 | 0.000 | 0.000 |
| Others | 1.237 | 2.368 | 2.867 | 7.018 | 3.114 | 8.624 | 1.140 | 2.109 | 1.021 | 1.114 |
| MEA Conversion, % | 26.02 | 37.12 | 38.74 | 58.74 | 41.99 | 63.48 | 22.75 | 32.08 | 14.00 | 12.93 |
| DETA Conversion, % | 13.50 | 20.70 | 21.21 | 33.62 | 22.94 | 35.25 | 12.48 | 17.80 | 9.30 | 7.64 |
| Acyclic(N4), % | 98.30 | 97.45 | 96.84 | 95.40 | 96.55 | 95.63 | 97.87 | 97.21 | 98.79 | 100.00 |
| Acyclic(N5), % | 100.00 | 94.05 | 91.70 | 86.09 | 91.37 | 89.13 | 100.00 | 92.76 | 100.00 | 0.000 |
| $\Sigma(N5)/\Sigma(N4)$, weight ratio | 0.22 | 0.38 | 0.41 | 0.65 | 0.47 | 0.71 | 0.23 | 0.37 | 0.16 | 0.000 |
| Acyclic(N4)/cyclic (<=N4), weight ratio | 16.04 | 12.16 | 10.56 | 7.23 | 9.23 | 6.47 | 13.23 | 10.42 | 13.92 | 15.87 |

TABLE XXIII

| Example No. | 259 | 260 | 261 | 262 | 263 | 264 | 265 | 266 | 267 | 268 |
|---|---|---|---|---|---|---|---|---|---|---|
| Catalyst Type | W | W | W | W | W | W | W | W | W | W |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.8 | 249.5 | 259.9 | 264.3 | 274.1 | 270.2 | 279.2 | 254.5 | 264.3 | 251.7 |
| Time on organics, hrs. | 4 | 24 | 28 | 48 | 52 | 72 | 72 | 96 | 100 | 120 |
| Duration of run, hrs. | 2 | 2 | 2 | 2 | 2 | 2 | 2 | 2 | 2 | 2 |
| MEA SV, gmol/hr/kgcat | 6.01 | 5.76 | 6.31 | 6.08 | 6.51 | 6.27 | 6.51 | 6.20 | 6.03 | 6.22 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.761 | 0.624 | 1.038 | 1.221 | 1.948 | 1.583 | 2.362 | 0.611 | 1.025 | 0.465 |
| MEA | 25.622 | 26.514 | 24.098 | 23.576 | 16.694 | 20.651 | 13.560 | 28.634 | 23.574 | 29.808 |
| PIP | 0.313 | 0.180 | 0.319 | 0.354 | 0.596 | 0.466 | 0.712 | 0.136 | 0.289 | 0.092 |
| DETA | 51.757 | 52.135 | 49.333 | 49.050 | 42.503 | 46.442 | 40.240 | 54.507 | 48.715 | 53.735 |
| AEEA | 2.271 | 2.049 | 2.327 | 2.321 | 1.938 | 2.152 | 1.499 | 1.953 | 2.175 | 1.635 |
| AEP | 0.469 | 0.304 | 0.391 | 0.428 | 0.713 | 0.549 | 0.914 | 0.271 | 0.386 | 0.235 |
| HEP | 0.000 | 0.000 | 0.000 | 0.000 | 0.000 | 0.000 | 0.000 | 0.000 | 0.000 | 0.000 |
| TAEA | 1.249 | 1.216 | 1.449 | 1.478 | 1.706 | 1.601 | 1.752 | 1.109 | 1.439 | 0.776 |
| 1-TETA | 8.948 | 8.159 | 9.767 | 9.512 | 11.779 | 10.430 | 12.550 | 6.599 | 9.395 | 4.640 |
| DAEP | 0.121 | 0.097 | 0.148 | 0.142 | 0.316 | 0.196 | 0.455 | 0.057 | 0.152 | 0.074 |
| PEEDA | 0.067 | 0.063 | 0.086 | 0.097 | 0.232 | 0.028 | 0.325 | 0.033 | 0.091 | 0.000 |
| DPE | 0.039 | 0.054 | 0.073 | 0.086 | 0.203 | 0.141 | 0.249 | 0.054 | 0.069 | 0.000 |
| AE-TAEA | 1.082 | 1.193 | 1.621 | 1.608 | 2.838 | 2.237 | 3.225 | 0.711 | 1.419 | 0.310 |
| 1-TEPA | 2.014 | 2.188 | 2.900 | 2.766 | 5.279 | 3.962 | 6.363 | 1.162 | 2.409 | 0.421 |
| AE-DAEP | 0.000 | 0.000 | 0.066 | 0.041 | 0.429 | 0.137 | 0.501 | 0.000 | 0.000 | 0.000 |
| AE-PEEDA | 0.000 | 0.000 | 0.000 | 0.000 | 0.162 | 0.052 | 0.290 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.083 | 0.071 | 0.078 | 0.546 | 0.099 | 0.570 | 0.264 | 0.111 | 0.000 |
| BPEA | 0.000 | 0.140 | 0.190 | 0.225 | 0.601 | 0.329 | 0.696 | 0.000 | 0.132 | 0.000 |
| Others | 1.401 | 1.373 | 1.963 | 2.198 | 5.197 | 3.367 | 6.347 | 1.172 | 1.892 | 0.943 |
| MEA Conversion, % | 30.38 | 28.05 | 34.69 | 35.69 | 54.79 | 43.71 | 63.20 | 22.55 | 34.28 | 15.16 |
| DETA Conversion, % | 16.63 | 16.13 | 20.74 | 20.69 | 31.77 | 24.95 | 35.27 | 12.60 | 19.49 | 9.33 |
| Acyclic(N4), % | 97.81 | 97.75 | 97.31 | 97.11 | 94.71 | 97.04 | 93.27 | 98.14 | 97.18 | 98.64 |
| Acyclic(N5), % | 100.00 | 93.80 | 93.22 | 92.68 | 82.34 | 90.92 | 82.32 | 87.61 | 93.99 | 100.00 |
| $\Sigma(N5)/\Sigma(N4)$, weight ratio | 0.29 | 0.37 | 0.42 | 0.41 | 0.69 | 0.54 | 0.75 | 0.27 | 0.36 | 0.13 |
| Acyclic(N4)/cyclic (<=N4), weight ratio | 10.08 | 13.38 | 10.99 | 9.89 | 6.53 | 8.70 | 5.38 | 13.91 | 10.95 | 13.46 |

TABLE XXIV

| Example No. | 269 | 270 | 271 | 272 |
|---|---|---|---|---|
| Catalyst Type | X | X | X | X |
| Catalyst weight, gm | 50 | 50 | 50 | 50 |
| Pressure, psig | 600 | 600 | 600 | 600 |
| Temperature, °C. | 249.8 | 264.3 | 274.1 | 270.2 |
| Time on organics, hrs. | 4 | 37 | 40 | 61 |
| Duration of run, hrs. | 2 | 2 | 2 | 2 |
| MEA SV, gmol/hr/kgcat | 5.86 | 5.73 | 5.94 | 5.40 |
| DETA/MEA mole ratio | 0.99 | 0.99 | 0.99 | 0.99 |
| $NH_3$/MEA mole ratio | 5.98 | 5.98 | 5.98 | 5.98 |
| Crude product composition, wt. % | | | | |
| EDA | 1.024 | 1.195 | 2.071 | 1.604 |
| MEA | 26.663 | 25.244 | 19.405 | 22.346 |
| PIP | 0.296 | 0.293 | 0.530 | 0.392 |
| DETA | 50.089 | 49.881 | 43.746 | 46.459 |
| AEEA | 1.810 | 1.985 | 1.764 | 1.910 |
| AEP | 0.383 | 0.382 | 0.629 | 0.466 |
| HEP | 0.000 | 0.000 | 0.000 | 0.000 |
| TAEA | 1.335 | 1.526 | 1.657 | 1.567 |
| 1-TETA | 7.810 | 8.794 | 10.168 | 9.213 |
| DAEP | 0.119 | 0.111 | 0.244 | 0.145 |
| PEEDA | 0.083 | 0.063 | 0.147 | 0.090 |
| DPE | 0.049 | 0.091 | 0.211 | 0.141 |
| AE-TAEA | 1.264 | 1.525 | 2.605 | 1.943 |
| 1-TEPA | 2.012 | 2.274 | 4.356 | 3.093 |
| AE-DAEP | 0.000 | 0.000 | 0.377 | 0.094 |
| AE-PEEDA | 0.057 | 0.000 | 0.155 | 0.035 |
| iAE-PEEDA | 0.000 | 0.000 | 0.000 | 0.000 |
| AE-DPE | 0.076 | 0.077 | 0.546 | 0.097 |
| BPEA | 0.038 | 0.166 | 0.533 | 0.257 |
| Others | 1.245 | 2.056 | 5.068 | 3.030 |
| MEA Conversion, % | 25.98 | 31.20 | 47.33 | 37.71 |
| DETA Conversion, % | 17.56 | 19.41 | 29.62 | 23.22 |
| Acyclic(N4), % | 97.31 | 97.48 | 95.14 | 96.61 |
| Acyclic(N5), % | 95.00 | 93.96 | 81.20 | 91.22 |
| Σ(N5)/Σ(N4), weight ratio | 0.36 | 0.38 | 0.68 | 0.49 |
| Acyclic(N4)/cyclic (<=N4), weight ratio | 9.81 | 10.94 | 6.70 | 8.72 |

TABLE XXV

| Example No. | 273 | 274 | 275 | 276 | 277 | 278 | 279 | 280 | 281 | 282 |
|---|---|---|---|---|---|---|---|---|---|---|
| Catalyst Type | Y | Y | Y | Y | Y | Y | Y | Y | Y | Y |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.8 | 249.5 | 259.9 | 264.3 | 274.1 | 270.2 | 279.2 | 254.5 | 264.3 | 251.7 |
| Time on organics, hrs. | 4 | 24 | 28 | 48 | 52 | 72 | 72 | 96 | 100 | 120 |
| Duration of run, hrs. | 2 | 2 | 2 | 2 | 2 | 2 | 2 | 2 | 2 | 2 |
| MEA SV, gmol/hr/kgcat | 5.10 | 4.90 | 5.23 | 5.17 | 5.39 | 5.13 | 5.44 | 5.16 | 5.11 | 5.35 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.960 | 0.781 | 1.286 | 1.404 | 2.490 | 1.935 | 2.792 | 0.714 | 1.281 | 0.493 |
| MEA | 25.276 | 26.501 | 22.272 | 21.316 | 14.838 | 19.716 | 11.330 | 27.403 | 22.785 | 27.477 |
| PIP | 0.268 | 0.204 | 0.383 | 0.358 | 0.742 | 0.540 | 0.837 | 0.168 | 0.348 | 0.103 |
| DETA | 50.594 | 51.409 | 47.463 | 45.857 | 40.344 | 44.583 | 37.401 | 53.232 | 47.558 | 54.912 |
| AEEA | 2.227 | 2.171 | 2.322 | 2.246 | 1.783 | 2.068 | 1.362 | 2.040 | 2.125 | .779 |
| AEP | 0.365 | 0.314 | 0.469 | 0.481 | 0.878 | 0.612 | 1.085 | 0.294 | 0.441 | 0.273 |
| HEP | 0.000 | 0.000 | 0.000 | 0.000 | 0.000 | 0.000 | 0.000 | 0.000 | 0.000 | 0.000 |
| TAEA | 1.233 | 1.224 | 1.587 | 1.506 | 1.615 | 1.578 | 1.689 | 1.266 | 1.424 | 1.095 |
| 1-TETA | 9.272 | 8.238 | 10.975 | 10.156 | 11.821 | 10.601 | 12.728 | 7.741 | 9.232 | 6.746 |
| DAEP | 0.116 | 0.088 | 0.175 | 0.175 | 0.394 | 0.229 | 0.599 | 0.075 | 0.153 | 0.071 |
| PEEDA | 0.072 | 0.059 | 0.117 | 0.170 | 0.031 | 0.173 | 0.376 | 0.041 | 0.100 | 0.028 |
| DPE | 0.061 | 0.053 | 0.092 | 0.124 | 0.233 | 0.160 | 0.305 | 0.047 | 0.090 | 0.000 |
| AE-TAEA | 1.263 | 1.061 | 1.872 | 2.256 | 3.087 | 2.494 | 3.494 | 0.922 | 1.714 | 0.435 |
| 1-TEPA | 2.381 | 1.850 | 3.306 | 4.088 | 5.984 | 4.457 | 6.930 | 1.552 | 2.925 | 0.540 |
| AE-DAEP | 0.000 | 0.000 | 0.049 | 0.183 | 0.533 | 0.160 | 0.701 | 0.000 | 0.039 | 0.000 |
| AE-PEEDA | 0.000 | 0.000 | 0.000 | 0.202 | 0.312 | 0.063 | 0.374 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.076 | 0.000 | 0.077 | 0.648 | 0.544 | 0.112 | 0.581 | 0.000 | 0.112 | 0.000 |
| BPEA | 0.118 | 0.075 | 0.262 | 0.540 | 0.639 | 0.399 | 0.995 | 0.049 | 0.240 | 0.000 |
| Others | 1.481 | 1.265 | 2.484 | 2.761 | 6.684 | 3.550 | 7.622 | 1.247 | 2.245 | 1.490 |
| MEA Conversion, % | 31.15 | 27.16 | 39.53 | 42.00 | 59.71 | 45.84 | 69.02 | 25.71 | 36.32 | 24.24 |
| DETA Conversion, % | 18.31 | 16.23 | 23.60 | 26.03 | 35.07 | 27.41 | 39.37 | 14.45 | 21.21 | 10.25 |
| Acyclic(N4), % | 97.67 | 97.91 | 97.01 | 96.12 | 95.31 | 95.57 | 91.83 | 98.20 | 96.87 | 98.74 |
| Acyclic(N5), % | 94.93 | 97.48 | 93.01 | 80.11 | 81.72 | 90.42 | 79.71 | 98.02 | 92.20 | 100.00 |
| Σ(N5)/Σ(N4), weight ratio | 0.35 | 0.30 | 0.43 | 0.65 | 0.78 | 0.60 | 0.83 | 0.27 | 0.45 | 0.12 |
| Acyclic(N4)/cyclic (<=N4), weight ratio | 11.88 | 13.13 | 10.13 | 8.90 | 5.89 | 7.09 | 4.49 | 14.33 | 9.39 | 16.44 |

TABLE XXVI

| Example No. | 283 | 284 | 285 | 286 | 287 | 288 | 289 | 290 |
|---|---|---|---|---|---|---|---|---|
| Catalyst Type | Z | Z | Z | Z | Z | Z | Z | Z |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 5.47 | 5.89 | 6.03 | 6.26 | 6.37 | 6.13 | 6.30 | 5.74 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.720 | 0.471 | 0.905 | 1.039 | 1.480 | 1.147 | 1.920 | 2.426 |
| MEA | 22.009 | 25.260 | 20.953 | 20.030 | 12.865 | 18.327 | 11.062 | 10.395 |

TABLE XXVI-continued

| Example No. | 283 | 284 | 285 | 286 | 287 | 288 | 289 | 290 |
|---|---|---|---|---|---|---|---|---|
| PIP | 0.236 | 0.148 | 0.320 | 0.360 | 0.596 | 0.411 | 0.716 | 0.888 |
| DETA | 49.471 | 53.904 | 50.021 | 50.155 | 43.606 | 48.889 | 42.722 | 43.690 |
| AEEA | 2.596 | 2.713 | 2.960 | 3.007 | 2.400 | 2.930 | 1.997 | 1.666 |
| AEP | 0.369 | 0.293 | 0.450 | 0.511 | 0.832 | 0.592 | 1.018 | 1.209 |
| HEP | 0.000 | 0.000 | 0.000 | 0.000 | 0.000 | 0.000 | 0.000 | 0.000 |
| TAEA | 1.431 | 1.225 | 1.593 | 1.658 | 1.845 | 1.669 | 1.892 | 1.745 |
| 1-TETA | 9.494 | 7.564 | 9.777 | 9.875 | 11.583 | 9.862 | 11.226 | 10.431 |
| DAEP | 0.148 | 0.096 | 0.184 | 0.198 | 0.402 | 0.207 | 0.439 | 0.480 |
| PEEDA | 0.122 | 0.090 | 0.106 | 0.123 | 0.320 | 0.113 | 0.034 | 0.294 |
| DPE | 0.066 | 0.055 | 0.069 | 0.086 | 0.155 | 0.046 | 0.133 | 0.167 |
| AE-TAEA | 1.452 | 0.810 | 1.783 | 1.741 | 3.025 | 1.768 | 3.034 | 2.823 |
| 1-TEPA | 2.655 | 1.402 | 3.149 | 3.152 | 5.660 | 3.141 | 5.502 | 5.191 |
| AE-DAEP | 0.000 | 0.000 | 0.000 | 0.048 | 0.304 | 0.056 | 0.503 | 0.535 |
| AE-PEEDA | 0.000 | 0.000 | 0.000 | 0.000 | 0.217 | 0.036 | 0.192 | 0.219 |
| iAE-PEEDA | 0.000 | 0.000 | 0.000 | 0.000 | 0.000 | 0.000 | 0.000 | 0.000 |
| AE-DPE | 0.085 | 0.000 | 0.106 | 0.088 | 0.532 | 0.055 | 0.161 | 0.144 |
| BPEA | 0.089 | 0.000 | 0.224 | 0.200 | 0.722 | 0.287 | 0.763 | 0.720 |
| Others | 1.049 | 1.041 | 2.233 | 2.823 | 5.516 | 3.315 | 7.516 | 7.487 |
| MEA Conversion, % | 37.93 | 30.47 | 42.95 | 45.73 | 64.84 | 49.30 | 69.45 | 71.21 |
| DETA Conversion, % | 17.29 | 12.04 | 19.27 | 19.45 | 29.37 | 19.83 | 30.06 | 28.28 |
| Acyclic(N4), % | 97.00 | 97.30 | 96.93 | 96.58 | 93.85 | 96.91 | 95.57 | 92.81 |
| Acyclic(N5), % | 95.91 | 100.00 | 93.70 | 93.55 | 83.01 | 91.86 | 84.03 | 83.18 |
| $\Sigma(N5)/\Sigma(N4)$, weight ratio | 0.38 | 0.24 | 0.44 | 0.43 | 0.73 | 0.44 | 0.74 | 0.73 |
| Acyclic(N4)/cyclic ($<=$N4), weight ratio | 11.57 | 12.82 | 10.05 | 9.01 | 5.82 | 8.40 | 5.59 | 4.00 |

TABLE XXVII

| Example No. | 291 | 292 | 293 | 294 | 295 | 296 | 297 | 298 |
|---|---|---|---|---|---|---|---|---|
| Catalyst Type | AA | AA | AA | AA | AA | AA | AA | AA |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 6.04 | 5.42 | 5.91 | 6.40 | 6.54 | 6.13 | 6.74 | 5.98 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.243 | 0.400 | 0.619 | 0.453 | 0.613 | 0.354 | 0.525 | 0.580 |
| MEA | 29.356 | 33.017 | 31.776 | 32.605 | 30.780 | 32.217 | 30.493 | 31.003 |
| PIP | 0.484 | 0.185 | 0.304 | 0.266 | 0.441 | 0.244 | 0.428 | 0.540 |
| DETA | 54.083 | 59.592 | 58.373 | 59.235 | 57.284 | 58.765 | 57.084 | 56.943 |
| AEEA | 1.249 | 0.742 | 1.272 | 1.184 | 1.363 | 1.159 | 1.500 | 1.300 |
| AEP | 0.395 | 0.262 | 0.352 | 0.330 | 0.422 | 0.301 | 0.428 | 0.482 |
| HEP | 0.000 | 0.000 | 0.000 | 0.000 | 0.000 | 0.000 | 0.000 | 0.000 |
| TAEA | 0.704 | 0.276 | 0.427 | 0.390 | 0.510 | 0.276 | 0.503 | 0.480 |
| 1-TETA | 3.680 | 1.530 | 2.245 | 1.887 | 2.609 | 1.462 | 2.595 | 2.425 |
| DAEP | 0.102 | 0.032 | 0.065 | 0.120 | 0.082 | 0.000 | 0.088 | 0.070 |
| PEEDA | 0.057 | 0.000 | 0.034 | 0.066 | 0.054 | 0.000 | 0.087 | 0.097 |
| DPE | 0.044 | 0.000 | 0.026 | 0.000 | 0.026 | 0.000 | 0.035 | 0.000 |
| AE-TAEA | 0.259 | 0.000 | 0.096 | 0.057 | 0.153 | 0.000 | 0.230 | 0.182 |
| 1-TEPA | 0.507 | 0.000 | 0.236 | 0.106 | 0.469 | 0.000 | 0.673 | 0.501 |
| AE-DAEP | 0.000 | 0.000 | 0.000 | 0.000 | 0.000 | 0.000 | 0.000 | 0.000 |
| AE-PEEDA | 0.133 | 0.000 | 0.000 | 0.000 | 0.000 | 0.000 | 0.067 | 0.000 |
| iAE-PEEDA | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.299 | 0.000 |
| BPEA | 0.000 | 0.000 | 0.000 | 0.000 | 0.000 | 0.000 | 0.000 | 0.000 |
| Others | 2.796 | 1.200 | 1.868 | 1.546 | 1.758 | 1.067 | 1.606 | 1.461 |
| MEA Conversion, % | 18.40 | 9.46 | 13.61 | 11.72 | 15.52 | 8.49 | 16.54 | 14.42 |
| DETA Conversion, % | 10.89 | 3.12 | 5.92 | 4.92 | 6.79 | 4.03 | 7.37 | 6.82 |
| Acyclic(N4), % | 95.54 | 98.24 | 95.49 | 92.41 | 95.03 | 100.00 | 93.59 | 94.56 |
| Acyclic(N5), % | 85.20 | 0.00 | 100.00 | 100.00 | 100.00 | 0.00 | 71.12 | 100.00 |
| $\Sigma(N5)/\Sigma(N4)$, weight ratio | 0.19 | 0.00 | 0.11 | 0.06 | 0.18 | 0.00 | 0.38 | 0.22 |
| Acyclic(N4)/cyclic ($<=$N4), weight ratio | 4.04 | 3.76 | 3.41 | 2.90 | 3.03 | 3.18 | 2.89 | 2.44 |

TABLE XXVIII

| Example No. | 299 | 300 | 301 | 302 | 303 | 304 | 305 | 306 |
|---|---|---|---|---|---|---|---|---|
| Catalyst Type | BB | BB | BB | BB | BB | BB | BB | BB |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |

TABLE XXVIII-continued

| Example No. | 299 | 300 | 301 | 302 | 303 | 304 | 305 | 306 |
|---|---|---|---|---|---|---|---|---|
| MEA SV, gmol/hr/kgcat | 4.89 | 4.52 | 5.00 | 4.97 | 5.03 | 4.67 | 5.18 | 4.59 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.361 | 0.219 | 0.411 | 0.545 | 0.946 | 0.691 | 1.268 | 1.591 |
| MEA | 30.065 | 31.539 | 30.198 | 28.886 | 25.101 | 27.183 | 22.856 | 21.265 |
| PIP | 0.191 | 0.101 | 0.235 | 0.344 | 0.686 | 0.468 | 0.951 | 1.183 |
| DETA | 57.915 | 60.816 | 59.141 | 58.453 | 55.105 | 56.245 | 52.509 | 52.661 |
| AEEA | 1.844 | 1.669 | 2.173 | 2.351 | 2.319 | 2.307 | 2.115 | 1.849 |
| AEP | 0.299 | 0.245 | 0.312 | 0.391 | 0.627 | 0.461 | 0.842 | 1.032 |
| HEP | 0.000 | 0.000 | 0.000 | 0.000 | 0.000 | 0.000 | 0.000 | 0.000 |
| TAEA | 0.476 | 0.214 | 0.406 | 0.515 | 0.745 | 0.564 | 0.870 | 0.894 |
| l-TETA | 2.817 | 1.483 | 2.555 | 3.157 | 4.703 | 3.517 | 5.428 | 5.629 |
| DAEP | 0.066 | 0.000 | 0.066 | 0.077 | 0.144 | 0.104 | 0.191 | 0.220 |
| PEEDA | 0.077 | 0.000 | 0.030 | 0.063 | 0.138 | 0.033 | 0.212 | 0.248 |
| DPE | 0.000 | 0.000 | 0.000 | 0.033 | 0.039 | 0.000 | 0.060 | 0.066 |
| AE-TAEA | 0.102 | 0.000 | 0.108 | 0.157 | 0.411 | 0.199 | 0.708 | 0.582 |
| l-TEPA | 0.142 | 0.000 | 0.113 | 0.379 | 1.210 | 0.590 | 2.108 | 1.711 |
| AE-DAEP | 0.000 | 0.000 | 0.000 | 0.000 | 0.041 | 0.000 | 0.126 | 0.089 |
| AE-PEEDA | 0.000 | 0.000 | 0.000 | 0.000 | 0.037 | 0.000 | 0.098 | 0.085 |
| iAE-PEEDA | 0.000 | 0.000 | 0.000 | 0.000 | 0.000 | 0.000 | 0.000 | 0.000 |
| AE-DPE | 0.000 | 0.000 | 0.311 | 0.284 | 0.170 | 0.250 | 0.050 | 0.078 |
| BPEA | 0.000 | 0.000 | 0.000 | 0.000 | 0.000 | 0.000 | 0.101 | 0.096 |
| Others | 0.939 | 0.839 | 1.295 | 1.748 | 2.458 | 1.973 | 3.578 | 3.552 |
| MEA Conversion, % | 16.32 | 13.59 | 17.86 | 21.73 | 30.80 | 24.34 | 36.90 | 40.66 |
| DETA Conversion, % | 4.44 | 1.22 | 4.64 | 6.11 | 9.94 | 7.19 | 14.06 | 12.88 |
| Acyclic(N4), % | 95.83 | 100.00 | 96.82 | 95.45 | 94.40 | 96.74 | 93.13 | 92.40 |
| Acyclic(N5), % | 100.00 | 0.00 | 41.61 | 65.36 | 86.70 | 75.90 | 88.18 | 86.75 |
| $\Sigma$(N5)/$\Sigma$(N4), weight ratio | 0.07 | 0.00 | 0.17 | 0.21 | 0.32 | 0.24 | 0.47 | 0.37 |
| Acyclic(N4)/cyclic (<=N4), weight ratio | 5.19 | 4.88 | 4.59 | 4.03 | 3.32 | 3.82 | 2.78 | 2.37 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process of making polyalkylene polyamines which comprises condensing, in the absence of hydrogen as a reactant,
   (i) an alkanolamine with an alkyleneamine, or
   (ii) an alkanolamine with itself or another alkanolamine optionally in the presence of ammonia, under condensation conditions including the presence of a condensation catalyst consisting essentially of a metatungstate and a Group IVB metal oxide.

2. The process of claim 1 wherein the Group IVB metal oxide comprises a high surface area titanium oxide or zirconium oxide.

3. The process of claim 1 wherein the catalyst has a surface area greater than about 70 m²/gm.

4. The process of claim 2 wherein the titanium oxide comprises titanium dioxide and the zirconium oxide comprises zirconium dioxide.

5. The process of claim 2 wherein the catalyst has a surface area greater than about 140 m²/gm.

6. The process of claim 1 wherein the Group IVB metal oxide comprises a mixed oxide of a Group IVB metal oxide and one or more other metal oxides.

7. The process of claim 6 wherein the metal oxide comprises one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, other Group IVB metal oxides or mixtures thereof.

8. The process of claim 6 wherein the metal oxide comprises one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

9. The process of claim 1 wherein the Group IVB metal oxide comprises from about 25 weight percent to about 90 weight percent of the weight of the catalyst.

10. The process of claim 1 wherein the Group IVB metal oxide comprises from about 50 weight percent to about 90 weight percent of the weight of the catalyst.

11. The process of claim 1 wherein the Group IVB metal oxide comprises from about 75 weight percent to about 90 weight percent of the weight of the catalyst.

12. The process of claim 1 wherein the amines product has a TETA+TAEA to PIP+AEP+PEEDA+DAEP+DPE weight ratio of greater than about 0.5 and a TETA to TAEA weight ratio of greater than about 4.0.

13. The process of claim 1 in which the amines product comprises, based on 100 percent of the weight of the product and exclusive of any water and/or ammonia present,
   a) greater than about 3.0 weight percent of the combination of TETA and TEPA,
   b) greater than about 0.1 weight percent of TEPA,
   c) greater than about 3.0 weight percent of TETA,
   d) less than about 90.0 weight percent of DETA and/or EDA,
   e) less than about 90.0 weight percent of MEA and/or AEEA,
   f) less than about 12.5 weight percent of the combination of PIP and AEP, g) less than about 15.0 weight percent of other polyalkylene polyamines, h) a TETA+TAEA to PIP+AEP+PEEDA+DAEP+DPE weight ratio of greater than about 0.5, i) a TEPA+AETAEA to PIP+AEP+PEEDA+DAEP+DPE+AEPEEDA+iAEPEEDA+AEDAEP+AEDPE+BPEA weight ratio of greater than about 0.5, j) a TETA to TAEA weight ratio of greater than about 4.0, and k) a TEPA to AETAEA weight ratio of greater than about 1.0.

14. The process of claim 1 which is effected in the liquid phase, vapor phase, supercritical liquid phase or mixtures thereof.

15. A process of making alkylamines which comprises condensing, in the absence of hydrogen as a reactant, an alcohol and at least one of a primary amine, a secondary amine or a tertiary amine in the presence of a condensation catalyst consisting essentially of a metatungstate and a Group IVB metal oxide.

16. The process of claim 1 wherein the condensation reaction is of said alkanolamine and alkyleneamine reactants (i).

17. The process of claim 16 wherein the alkanolamine is monoethanolamine.

18. The process of claim 16 wherein the alkanolamine is aminoethylethanolamine.

19. The process of claim 16 wherein the alkyleneamine is ethylenediamine.

20. The process of claim 16 wherein the alkyleneamine is diethylenetriamine.

21. The process of claim 16 wherein the alkanolamine is monoethanolamine and the alkyleneamine is ethylenediamine.

22. The process of claim 21 wherein the process is effected in the presence of ammonia.

23. The process of claim 16 wherein the alkanolamine is monoethanolamine and the alkyleneamine is diethylenetriamine.

24. The process of claim 23 wherein the process is effected in the presence of ammonia.

25. The process of claim 16 wherein the alkanolamine is aminoethylethanolamine and the alkyleneamine is ethylenediamine.

26. The process of claim 25 wherein the process is effected in the presence of ammonia.

27. The process of claim 16 wherein the alkanolamine is aminoethylethanolamine and the alkyleneamine is diethylenetriamine.

28. The process of claim 27 wherein the process is effected in the presence of ammonia.

29. The process of claim 16 wherein the alkanolamine is diethanolamine and the alkyleneamine is ethylenediamine or diethylenetriamine.

30. The process of claim 16 wherein the alkanolamine is dihydroxyethylethylenediamine and the alkyleneamine is ethylenediamine or diethylenetriamine.

31. The process of claim 16 wherein the alkanolamine is hydroxyethyldiethylenetriamine and the alkyleneamine is ethylenediamine or diethylenetriamine.

32. The process of claim 16 wherein the alkanolamine is hydroxyethyltriethylenetetramine and the alkyleneamine is ethylenediamine or diethylenetriamine.

33. The process of claim 1 wherein the condensation reaction is of said alkanolamine reactant (ii) with itself.

34. The process of claim 33 wherein said alkanolamine is monoethanolamine.

35. The process of claim 15 further comprising ammonia as a reactant.

* * * * *